United States Patent
Hochrein et al.

(10) Patent No.: US 11,273,211 B2
(45) Date of Patent: Mar. 15, 2022

(54) COMBINATION THERAPY FOR TREATING CANCER WITH AN INTRAVENOUS ADMINISTRATION OF A RECOMBINANT MVA AND AN ANTIBODY

(71) Applicant: Bavarian Nordic A/S, Kvistgaard (DK)

(72) Inventors: Hubertus Hochrein, Munich (DE); Henning Lauterbach, Eching (DE); José Medina Echeverz, Munich (DE); Matthias Habjan, Gauting (DE)

(73) Assignee: Bavarian Nordic A/S, Hellerup (DK)

( * ) Notice: Subject to any disclaimer, the term of this patent is extended or adjusted under 35 U.S.C. 154(b) by 0 days.

(21) Appl. No.: 16/641,236

(22) PCT Filed: Aug. 23, 2018

(86) PCT No.: PCT/EP2018/072789
§ 371 (c)(1),
(2) Date: Feb. 22, 2020

(87) PCT Pub. No.: WO2019/038388
PCT Pub. Date: Feb. 28, 2019

(65) Prior Publication Data
US 2020/0306352 A1 Oct. 1, 2020

(30) Foreign Application Priority Data
Aug. 24, 2017 (EP) .................................... 17187824

(51) Int. Cl.
*A61K 39/00* (2006.01)
*A61K 39/285* (2006.01)

(52) U.S. Cl.
CPC ............... *A61K 39/001106* (2018.08); *A61K 39/001152* (2018.08); *A61K 39/285* (2013.01); *A61K 2039/505* (2013.01); *A61K 2039/5256* (2013.01); *A61K 2039/53* (2013.01); *A61K 2039/54* (2013.01); *A61K 2039/55516* (2013.01); *A61K 2039/57* (2013.01); *A61K 2039/6075* (2013.01); *A61K 2039/70* (2013.01)

(58) Field of Classification Search
CPC .............. A61K 2300/00; A61K 39/395; A61K 38/177; A61K 2039/5256; A61K 39/0011; A61K 39/285; C12N 2799/021; C12N 15/64; C12N 2770/20022; C12N 2770/20034; C12N 15/1034; C12N 2710/10034; C12N 2710/12034; C12N 2710/16634; C12N 2760/14134; C12N 2760/16034; C12N 2770/24222; C12N 2770/24234; C12N 2800/204; C12N 2800/50; C07K 2317/55
See application file for complete search history.

(56) References Cited

FOREIGN PATENT DOCUMENTS

| WO | 2005012527 A1 | 2/2005 |
|----|---------------|--------|
| WO | 2014037124 A1 | 3/2014 |
| WO | 2014043518 A1 | 3/2014 |
| WO | 2014043535 A1 | 3/2014 |
| WO | 2015069571 A1 | 5/2015 |
| WO | 2016007499 A1 | 1/2016 |

OTHER PUBLICATIONS

Foy et al., "Poxvirus-based active immunotherapy synergizes with CTLA-4 blockade to increase survival in a murine tumor model . . . ," Cancer Immunol. Immunother., 2016, pp. 537-549, vol. 65.
Hamilton et al., "Development of Cancer Vaccines Targeting Brachyury . . . ," Cells Tissues Organs, 2017, pp. 128-138, vol. 203.

*Primary Examiner* — Bao Q Li

(57) ABSTRACT

The invention relates to a pharmaceutical combination and related methods for reducing tumor volume and/or increasing the survival of a cancer patient. The combination comprises an intravenous administration of a recombinant MVA encoding a tumor-associated antigen and an administration of an antibody to a cancer patient.

9 Claims, 33 Drawing Sheets
Specification includes a Sequence Listing.

A

B

A

B

C

COMBINATION THERAPY FOR TREATING CANCER WITH AN INTRAVENOUS ADMINISTRATION OF A RECOMBINANT MVA AND AN ANTIBODY

This application is a National Phase application under 35 U.S.C. § 371 of International Application No. PCT/EP2018/072789, filed Aug. 23, 2018, and claims the benefit under 35 U.S.C. § 365 of European Application 17187824.2, filed Aug. 24, 2017, the disclosures of which are incorporated by reference herein in their entirety.

FIELD OF THE INVENTION

The present invention relates to a combination therapy for the treatment of cancers, the combination including an intravenously administered recombinant modified vaccinia Ankara (MVA) virus comprising a nucleic acid encoding a heterologous tumor-associated antigen (TAA) and an antibody.

BACKGROUND OF THE INVENTION

Recombinant poxviruses have been used as immunotherapy vaccines against infectious organisms and, more recently, against tumors (see Mastrangelo et al. (2000) *J Clin Invest.* 105(8): 1031-1034).

One poxviral strain that has proven useful as an immunotherapy vaccine against infectious disease and cancer is the Modified Vaccinia Ankara (MVA) virus. MVA was generated by 516 serial passages on chicken embryo fibroblasts of the Ankara strain of vaccinia virus (CVA) (for review see Mayr et al. (1975) *Infection* 3: 6-14). As a consequence of these long-term passages, the genome of the resulting MVA virus had about 31 kilobases of its genomic sequence deleted and, therefore, was described as highly host cell restricted for replication to avian cells (Meyer et al. (1991) *J. Gen. Virol.* 72: 1031-1038). It was shown in a variety of animal models that the resulting MVA was significantly avirulent (Mayr & Danner (1978) *Dev. Biol. Stand.* 41: 225-34). Strains of MVA having enhanced safety profiles for the development of safer products, such as vaccines or pharmaceuticals, have been described (See International PCT publication WO2002042480; see also, e.g., U.S. Pat. Nos. 6,761,893 and 6,913,752, all of which are incorporated by reference herein). Such variants are capable of reproductive replication in non-human cells and cell lines, especially in chicken embryo fibroblasts (CEF), but are replication incompetent in human cell lines, in particular including HeLa, HaCat and 143B cell lines. Such strains are also not capable of reproductive replication in vivo, for example, in certain mouse strains, such as the transgenic mouse model AGR 129, which is severely immune-compromised and highly susceptible to a replicating virus (see U.S. Pat. No. 6,761,893). Such MVA variants and its derivatives, including recombinants, referred to as "MVA-BN," have been described (see International PCT publication WO2002042480; see also, e.g., U.S. Pat. Nos. 6,761,893 and 6,913,752).

The use of poxviral vectors that encode tumor-associated antigens (TAAs) have been shown to successfully reduce tumor size as well as increase overall survival rate of cancer patients (see, e.g., WO 2014/062778). It has been demonstrated that when a cancer patient is administered a poxviral vector encoding a TAA, such as HER2, CEA, MUC1, and/or Brachyury, a robust and specific T-cell response is generated by the patient to fight the cancer (Id; see also, Guardino et al. (2009) *Cancer Res.* 69: Abstract 5089, Heery et al. (2015) *JAMA Oncol.* 1: 1087-95).

HER2 is one such TAA that has been shown to be effective when encoded as part of a poxviral vector (Id.). HER2 is a tumor-associated antigen that is over-expressed in certain types of tumor cells in some patients having different types of cancer, such as breast, colorectal, lung, ovarian, cervical, bladder, gastric, and urothelial cancers. Immunization with various HER2 polypeptides has been used to generate an immune response against tumor cells expressing this antigen, as has vaccination with recombinant modified vaccinia virus Ankara ("MVA") vectors expressing a modified form of the HER2 protein (i.e., MVA-BN-HER2). (See, e.g., Renard et al. (2003) *J. Immunol.* 171:1588-1595; Mittendorf et al. (2006) *Cancer* 106: 2309-2317; Mandl et al. (2012) *Cancer Immunol. Immunother.* 61(1):19-29).

Previous work with MVA-BN-HER2 showed that it induced a TH1-biased immune response having both antibody and cellular components (see, e.g., Mandl et al. (2012)). Some workers have shown that a balanced immune response including both humoral and cell-mediated components is important for protection from and clearance of a variety of pathogens in the context of infectious disease (see, e.g., Hutchings et al. (2005) *J. Immunol.* 175: 599-606).

In addition to their effectiveness with TAAs, poxviruses, such as MVA have been shown to have enhanced efficacy when combined with a CD40 agonist such as CD40 Ligand (CD40L) (see WO 2014/037124). CD40/CD40L is a member of the tumor necrosis factor receptor/tumor necrosis factor ("TNFR/TNF") superfamily. While CD40 is constitutively expressed on many cell types, including B-cells, macrophages and DCs, its ligand CD40L is predominantly expressed on activated CD4+ T-cells (Lee et al. (2002) *J Immunol.* 171(11): 5707-5717; Ma and Clark (2009) *Semin. Immunol.* 21(5):265-272). The cognate interaction between DCs and CD4+ T-cells early after infection or immunization 'licenses' DCs to prime CD8+ T-cell responses (Ridge et al. (1998) *Nature* 393(6684): 474-478). DC licensing results in the upregulation of co-stimulatory molecules, increased survival and better cross-presenting capabilities of DCs. This process is mainly mediated via CD40/CD40L interaction (Bennet et al. (1998) *Nature* 393(6684): 478-480; Schoenberger et al. (1998) *Nature* 393(6684): 480-483), but CD40/CD40L-independent mechanisms also exist (CD70, LT.beta.R). Interestingly, a direct interaction between CD40L expressed on DCs and CD40 expressed on CD8+ T-cells has also been suggested, providing a possible explanation for the generation of helper-independent CTL responses (Johnson et al. (2009) *Immunity* 30(2): 218-227).

Several studies indicate that agonistic anti-CD40 antibodies may be useful as a vaccine adjuvant. In addition, recombinant AdV (Kato et al. (1998) *J. Clin. Invest.* 101(5): 1133-1141) and VV (Bereta et al. (2004) *Cancer Gen. Ther.* 11(12): 808-818) encoding CD40L have been created that showed superior immunogenicity in vitro and in vivo compared to non-adjuvanted viruses.

CD40L, when encoded as part of an MVA, was shown to be able to induce and enhance the overall T-cell response for a disease associated antigen (WO 2014/037124). In WO 2014/037124 it was shown that a recombinant MVA encoding CD40L and a heterologous antigen was able to enhance DC activation in vivo, increase T-cell responses specific to the heterologous antigen and enhance the quality and quantity of CD8 T-cells (Id.).

The use of antibodies for cancer therapy has also seen considerable success in the past decade (see, e.g., Scott et al.

(2012) *Nature Reviews Cancer* 12: 278-287). There are several antibody therapies that have received FDA approval and kill tumor cells in a variety of ways. For example, antibody therapies can kill tumor cells through direct action of the antibody, such as an antibody binding to a tumor antigen on the cell surface (Id.; see also Brodowicz et al. (2001) *Br. J. Cancer* 85: 1764-70). This can lead to apoptosis and death of the tumor cell as well as inhibition of tumor receptor activity. Preventing receptor activity can include: preventing dimerization of the tumor receptor, preventing kinase activation, blocking of extracellular receptor cleavage, induction of receptor internalization and down-stream signaling. The inhibition of tumor receptor activity by antibody therapies can prevent tumor proliferation. Id.

Antibody therapies can additionally kill tumor cells, by improving a cancer patient's own immune system to attack the tumor cell, termed immune-mediated tumor cell killing (Id) Immune-mediated tumor cell killing can include phagocytosis, complement activation, antibody-dependent cellular cytotoxicity (ADCC), genetically modified T-cells being targeted to the tumor by antibody, and inhibition of T cell inhibitor receptors, such as CTLA-4 (Id).

ADCC is one of the most important ways by which antibody therapies attack and destroy tumor cells. ADCC is triggered through interaction between a target-bound antibody on a tumor cell membrane and effector cells from a patient's immune system (Wang et al. (2015) *Front. Immunol.* 6: 368). The anti-tumor efficacy of many antibody therapies has been shown to be Natural Killer (NK) cell dependent (Id.). Human NK cells can express proteins that bind to the Fc portion of the antibodies. Once bound and activated, the NK cells mediate tumor killing through several pathways, including exocytosis of cytotoxic granules, TNF family death receptor signaling, and pro-inflammatory cytokine release, such as IFNγ (Id).

While there are successful poxviral cancer treatments, chemo- and radiotherapies, and antibody therapies available to cancer patients, there are many mechanisms that tumor cells employ to escape and/or diminish these treatments. For example, in order to escape a patient's specific immune system, many tumor cells utilize immune checkpoint molecules and/or lower specific Major Histocompatibility Complex (MHC) expression so as to suppress and/or evade detection by the specific CD8 T cells of the immune system (Scott et al. (2012)). Tumor cells have additionally been shown to evade a patient's innate immune response by modifying or decreasing tumor antigen expression on the tumor cell surface which can decrease both antibody binding, and tumor killing by the NK cells (Id).

More recently it has been discovered that tumor cells can evade the immune system and cancer therapies by entering an equilibrium phase with a cancer patient's immune system (see Bhatia et al. (2011) *Cancer Microenvironment* 4: 209-217). In at least one aspect of the equilibrium phase, tumor cells can remain in the body below the threshold of conventional morphologic recognition or cytogenetic recognition (Id). For example, expression of tumor antigen receptors on tumor cells will fluctuate and, in many cases, decrease to a point that is below the threshold at which the immune system can recognize the tumor cell (Id).

Given the ability of cancers and tumor cells to actively evade cancer therapies and a patient's immune system, there exists a substantial need for developing cancer treatments that effectively target and kill those tumor cells that actively evade the immune system. Additionally, there exists a need for cancer treatments that can attack and kill tumors and tumor cells that utilize an equilibrium phase to evade therapies and immune systems. At least in one aspect, the various embodiments of the present invention successfully overcome difficulties involving treating tumor cells that actively evade the immune system.

BRIEF SUMMARY OF THE INVENTION

It was determined in the various embodiments of the present invention that a recombinant MVA when administered intravenously to a patient in combination with antibody against a tumor surface antigen enhances treatment of the cancer patient, more particularly increases reduction in tumor volume and/or increases survival of the cancer patient.

Accordingly, in one embodiment, the present invention includes a pharmaceutical combination for use in reducing tumor size and/or increasing survival in a cancer patient, the pharmaceutical combination comprising: a) a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced T cell response in the cancer patient as compared to a NK cell and T cell response induced by a non-intravenous administration of a recombinant MVA comprising a nucleic acid encoding a heterologous tumor-associated antigen; and b) an antibody, wherein the antibody comprises an Fc domain and is specific to an antigen that is expressed on the cell membrane of a tumor cell; wherein administration of a) and b) to the cancer patient reduces tumor size and/or increases the survival rate of the cancer patient as compared to a non-intravenous administration of either a) or b) alone. In additional embodiments, the recombinant MVA further comprises a second nucleic acid encoding a second heterologous TAA.

In one or more preferred embodiments, the pharmaceutical combination further comprises CD40L. In a most preferred embodiment, the CD40L is encoded by the recombinant MVA.

In various embodiments, the antibody is approved for the treatment of a cancer patient. In one or more particular embodiments, the antibody is selected from the group consisting of: anti-CD20 (e.g., rituximab, ofatumumab, tositumomab); Anti-CD52 (e.g., alemtuzumab, Campath® antibody); anti-EGFR (e.g., cetuximab (Erbitux® antibody), panitumumab); anti-CD2 (e.g., siplizumab); anti-CD37 (e.g., BI836826); anti-CD123 (e.g., JNJ-56022473); anti-CD30 (e.g., XmAb2513); anti-CD38 (e.g., daratumumab (Darzalex® antibody)); anti-PDL1 (e.g., avelumab, atezolilzumab, durvalumab); anti-CTLA-4 (e.g., ipilumumab); anti-GD2 (e.g., 3F8, ch14.18, KW-2871, dinutuximab); anti-CEA; anti-MUC1; anti-FLT3; anti-CD19; anti-CD40; anti-SLAMF7; anti-CCR4; anti-B7-H3; anti-ICAM1; anti-CSF1R; anti-CA125 (e.g., oregovomab), anti-FRα (e.g., MOv18-IgG1, mirvetuximab soravtansine (IMGN853), MORAb-202); anti-mesothelin (e.g., MORAb-009); and anti-HER2. In a more preferred embodiment, the antibody is an anti-HER2 antibody. In a most preferred embodiment, the antibody is an anti-HER2 antibody selected from pertuzumab, trastuzumab, Herzuma® antibody, ABP 980, and ado-trastuzumab emtansine.

In various additional embodiments, the first and/or second TAA comprises one or more mutations to prevent the first and/or second TAA from binding and/or interacting with the antibody of the combination therapy. In one or more preferred embodiments, the first TAA is a HER2 antigen. In a more preferred embodiment the HER2 antigen comprises one or more mutations to prevent the binding of the first TAA to the anti-HER2 antibody. In additional preferred embodiments, the second TAA is a Brachyury antigen. In a more preferred embodiment, the Brachyury antigen comprises one or more mutations to the nuclear localization signaling (NLS) domain.

In one or more preferred embodiments, the recombinant MVA is MVA-BN or a derivative thereof.

In various embodiments, the present invention is directed to one or more methods of reducing tumor size and/or increasing survival of a cancer patient. In one embodiment, there is a method comprising: (a) intravenously administering to the cancer patient a recombinant MVA comprising a first nucleic acid encoding a first heterologous tumor-associated antigen (TAA) that when administered intravenously induces both an enhanced Natural Killer (NK) cell response and an enhanced T cell response in the cancer patient as compared to an NK cell response and a T cell response induced by a non-intravenous administration of a recombinant MVA virus comprising a nucleic acid encoding a heterologous tumor-associated antigen; and (b) administering to the cancer patient an antibody, wherein the antibody comprises an Fc domain and is specific to an antigen that is expressed on the cell membrane of a tumor cell; wherein administration of (a) and (b) to the cancer patient reduces tumor size in the cancer patient and/or increases the survival rate of the cancer patient as compared to a non-intravenous administration of either (a) or (b) alone.

In one or more preferred embodiments, the method comprises intravenously administering CD40L to the cancer patient. In a more preferred embodiment the CD40L is encoded by the recombinant MVA.

In another embodiment, the recombinant MVA of present invention is administered at the same time or after administration of the antibody. In a more preferred embodiment, the recombinant MVA is administered after the antibody.

In yet another embodiment, the present invention includes a method for enhancing antibody therapy in a cancer patient, the method comprising administering the pharmaceutical combination of the present invention to a cancer patient, wherein administering the pharmaceutical combination enhances antibody dependent cell-mediated cytotoxicity (ADCC) induced by the antibody therapy, as compared to administering the antibody therapy alone.

In still another embodiment, there is a method for inducing both an enhanced innate and an enhanced adaptive immune response in a cancer patient comprising administering a pharmaceutical combination of the present disclosure, wherein administering the pharmaceutical combination enhances both the innate and adaptive immune responses of the cancer patient as compared to a non-intravenous administration of the pharmaceutical combination or elements of the combination by themselves.

In still various additional embodiments, the present invention is directed to one or more synthetic peptides and nucleic acids encoding the synthetic peptides. In more specific embodiments, there is a synthetic HER2 peptide and nucleic acid. In more preferred embodiments, the synthetic HER2 peptide includes one or more mutations that prevent the HER2 peptide from binding a HER2 antibody, preferably an antibody selected from pertuzumab, trastuzumab, Herzuma® antibody, ABP 980, and ado-trastuzumab emtansine. In additional preferred embodiments, the synthetic HER2 peptide includes one or more mutations that prevent extracellular dimerization, tyrosine kinase activity, and/or phosphorylation of the HER2 antigen.

In another more specific embodiment, there are one or more synthetic Brachyury peptides and nucleic acids. In more preferred embodiments, the synthetic Brachyury polypeptides and nucleic acids include one or more mutations in the nuclear localization signaling (NLS) domain.

Additional objects and advantages of the invention will be set forth in part in the description which follows, and in part will be obvious from the description or may be learned by practice of the invention. The objects and advantages of the invention will be realized and attained by means of the elements and combinations particularly pointed out in the appended claims.

The accompanying drawings, which are incorporated in and constitute a part of this specification, illustrate one or more embodiments of the invention and together with the description, serve to explain the principles of the invention.

BRIEF DESCRIPTION OF THE DRAWINGS

FIG. 1A: NKp46$^+$CD3$^-$ cells; FIG. 1B: CD69; FIG. 1C: NKG2D; FIG. 1D: FasL; FIG. 1E: Bcl-X$_L$; FIG. 1F: CD70; and FIG. 1G: IFN-γ.

FIG. 2A: NKp46$^+$CD3$^-$ cells; FIG. 2B: CD69; FIG. 2C: NKG2D; FIG. 2D: FasL; FIG. 2E: Bcl-X$_L$; FIG. 2F: CD70; and FIG. 2G: IFN-γ.

FIG. 3A: NKp46$^+$CD3$^-$ cells; FIG. 3B: CD69; FIG. 3C: NKG2D; FIG. 3D: FasL; FIG. 3E: Bcl-X$_L$; FIG. 3F: CD70; and FIG. 3G: IFN-γ.

FIG. 4A: NKp46$^+$CD3$^-$ cells; FIG. 4B: CD69; FIG. 4C: FasL; FIG. 4D: Bcl-X$_L$; FIG. 4E: CD70; and FIG. 4F: IFN-γ.

FIG. 5A: NKp46$^+$CD3$^-$ cells; FIG. 5B: CD69; FIG. 5C: FasL; FIG. 5D: Bcl-X$_L$; FIG. 5E: CD70; and FIG. 5F: IFN-γ.

FIG. 6A: NKp46$^+$CD3$^-$ cells; FIG. 6B: CD69; FIG. 6C: FasL; FIG. 6D: Bcl-X$_L$; FIG. 6E: CD70; and FIG. 6F: IFN-γ.

FIG. 7A: The concentration of IFN-γ was higher after rMVA-CD40L as compared to MVA-OVA (rMVA) immunization. FIG. 7B: The NK cell activating cytokine IL-12p70 was only detectable after MVA-CD40L immunization. High serum levels of IFN-γ are in line with higher frequencies of IFN-γ$^+$ NK cells (see FIG. 1G) and CD69$^+$ granzyme B$^+$ NK cells in the spleen (FIG. 7C) after rMVA-CD40L immunization. Similar responses were seen in NHPs (*Macaca fascicularis*) after IV (intravenous) injection of MVA-MARV-GP-huCD40L (rMVA-CD40L), namely higher serum concentrations of IFN-γ (FIG. 7D) and IL-12p40/70 (FIG. 7E) as well as more proliferating (Ki67$^+$) NK cells (FIG. 7F) as compared to MVA-MARV-GP (rMVA).

FIG. 8A: CD3$^-$CD19$^-$NKp46$^+$; FIG. 8B: NK cell proliferation marker Ki67; and FIG. 8C: CD69 expression (shown as Geometric Mean Fluorescence Intensity (GMFI)).

FIG. 10A: C57BL/6 mice were treated IV either with 25 μg anti-CD4, rMVA+5 μg rat IgG2b, 1 μg anti-CD4 or MVA-OVA (rMVA)+1 μg anti-CD4. CD4 T cell (CD3$^+$CD4$^+$) depletion in the liver was analyzed and is shown as percent specific killing. To assess ex vivo ADCC activity of NK cells, (FIG. 10B) C57BL/6 or (FIG. 10C) Balb/c mice were immunized IV either with PBS, MVA-OVA (rMVA) or MVA-OVA-CD40L (rMVA-CD40L). FIG. 10E: Balb/c mice were immunized IV either with PBS or MVA-HER2-Twist-CD40L. Splenic NK cells were purified and used as effectors in antibody-dependent killing assays. B16.F10 cells were coated with mouse anti-human/mouse Trp1 mAb (clone TA99, FIG. 10B) and (FIG. 10C) CT26-HER2 cells were coated with mouse anti-human HER2 mAb (clone 7.16.4). Purified NK cells were added to the antibody-coated target cells at a 5:1 and 4:1 ratio, respectively. FIG. 10D: CT26-HER2 cells incubated with different concentrations of anti-human HER2 were also more efficiently killed by rMVA-CD40L activated NK cells as compared to rMVA activated NK cells. FIG. 10E: CT26-HER2 cells were coated with various concentrations of mouse anti-human HER2 mAb (clone 7.16.4). Purified NK cells were added to the antibody-coated target cells at a 5:1 ratio.

FIG. 13A Shows GMFI CD69 and FIG. 13B shows frequency of Ki67$^+$ NK cells.

FIG. 14B: CXCL10; FIG. 14C: IFN-α; FIG. 14D: IL-22; FIG. 14E: IFN-γ; FIG. 14F: CXCL1; FIG. 14G: CCL4; FIG. 14H: CCL7; FIG. 14I: CCL2; FIG. 14J: CCL5; FIG. 14K: TNF-α; FIG. 14L: IL-12p70; and FIG. 14M: IL-18.

FIG. 15A: CD8 T cell frequencies were assessed; FIG. 15B: B8 specific CD8 T cell responses were assessed, FIG. 15C: Transgene-specific (OVA) responses were assessed; and FIG. 15D: Ratios of OVA/B8-specific CD8 T cells were assessed.

FIG. 16A: CD44$^+$CD62L$^-$CD8 T cells; and FIG. 16B: CD4 T cells in the blood were monitored.

FIG. 19A: CD8 T cell responses were measured. FIG. 19B: OVA-specific CD8 T cell responses were measured. FIG. 19C represents overall survival.

(FIG. 20B) mean volume. FIG. 20C: Overall survival is shown.

FIG. 21A: Frequency of CD8$^+$ T cells among CD45$^+$ leukocytes in spleen, tumor-draining lymph nodes (TDLN) and tumor tissues; FIG. 21B: distribution of OVA$_{257-264}$-specific CD8$^+$ T cells in different organs upon immunization; FIG. 21C: GMFI of PD-1 and Lag3 on tumor-infiltrating OVA$_{257-264}$-specific CD8$^+$ T cells; FIG. 21D: representative dot plots of tumor-infiltrating CD8$^+$ T cells showing Ki67 and PD-1 expression; FIG. 21E: frequency of tumor-infiltrating Ki67$^+$ CD8$^+$ T cells and GMFI of PD-1; FIG. 21F: frequency of tumor-infiltrating regulatory T cells (Treg) among CD45$^+$ leukocytes; and FIG. 21G: frequency of PD-1$^{high}$- and PD-1$^{neg}$-tumor-infiltrating Treg.

FIG. 23A: Frequency of Foxp3$^+$CD4$^+$ Treg among CD4$^+$ T cells in tumor tissues; FIG. 23B: Ratio of CD8$^+$CD44$^+$ effector T cells (Teff) to Foxp3$^+$CD4$^+$ Tregs.

(FIG. 29B) CD86; and (FIG. 29C) MHC class II was measured by flow cytometry. FIG. 29D: The concentration of IL-12p70 was quantified.

DETAILED DESCRIPTION OF THE INVENTION

Figure 1:
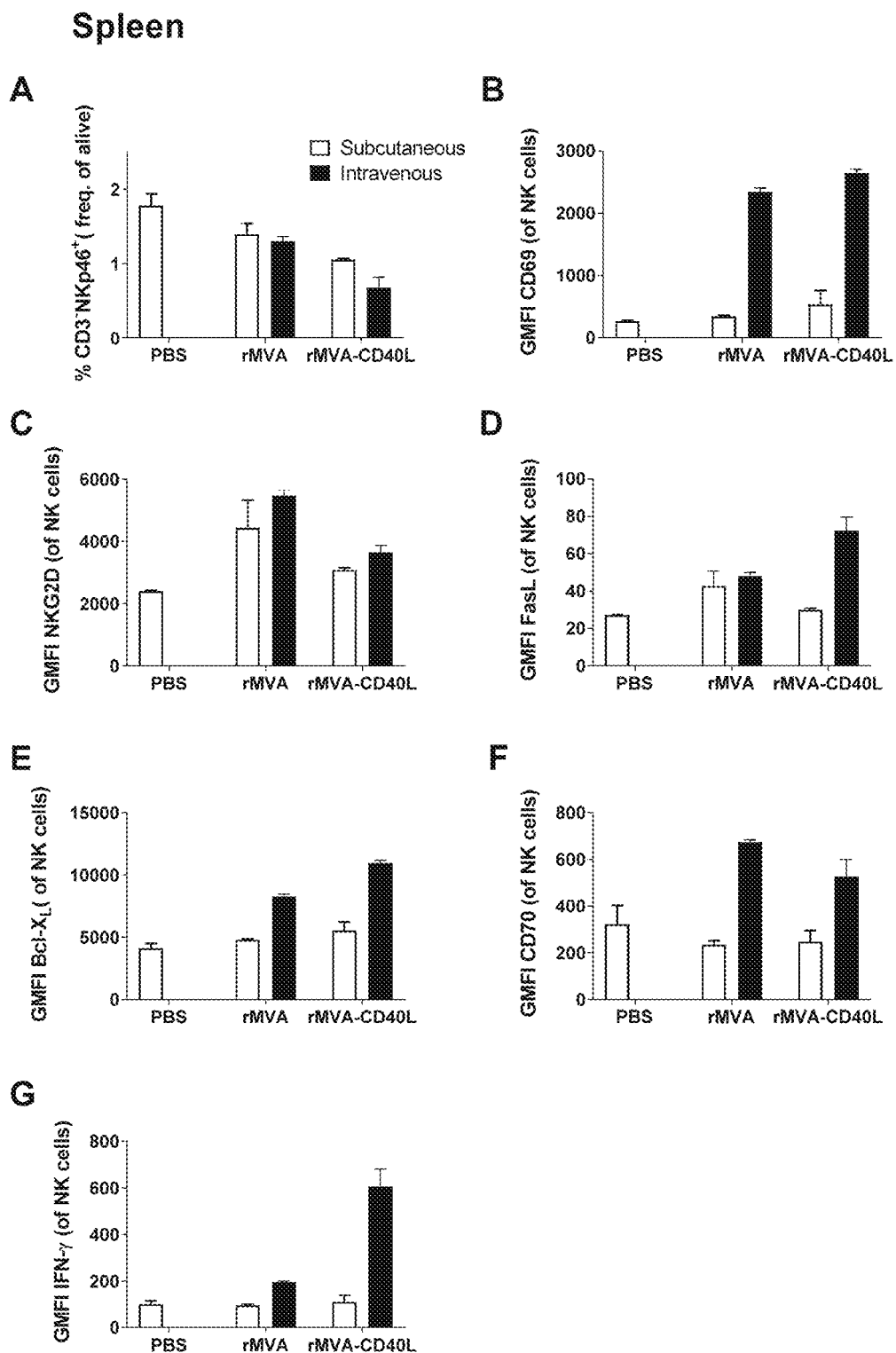
FIGS. 1A-1G show that intravenous (IV) administration of MVA-OVA (rMVA) leads to a stronger systemic activation of NK cells as compared to subcutaneous (SC) administration. NK cell activation is further enhanced when the MVA encodes CD40L (rMVA-CD40L). Shown are the results of Example 1, wherein staining to assess NK cell frequencies and expression (shown as Geometric Mean Fluorescence Intensity (GMFI)) of the named protein markers in NKp46$^+$CD3$^-$ cells was assessed in the spleen.
Figure 2:
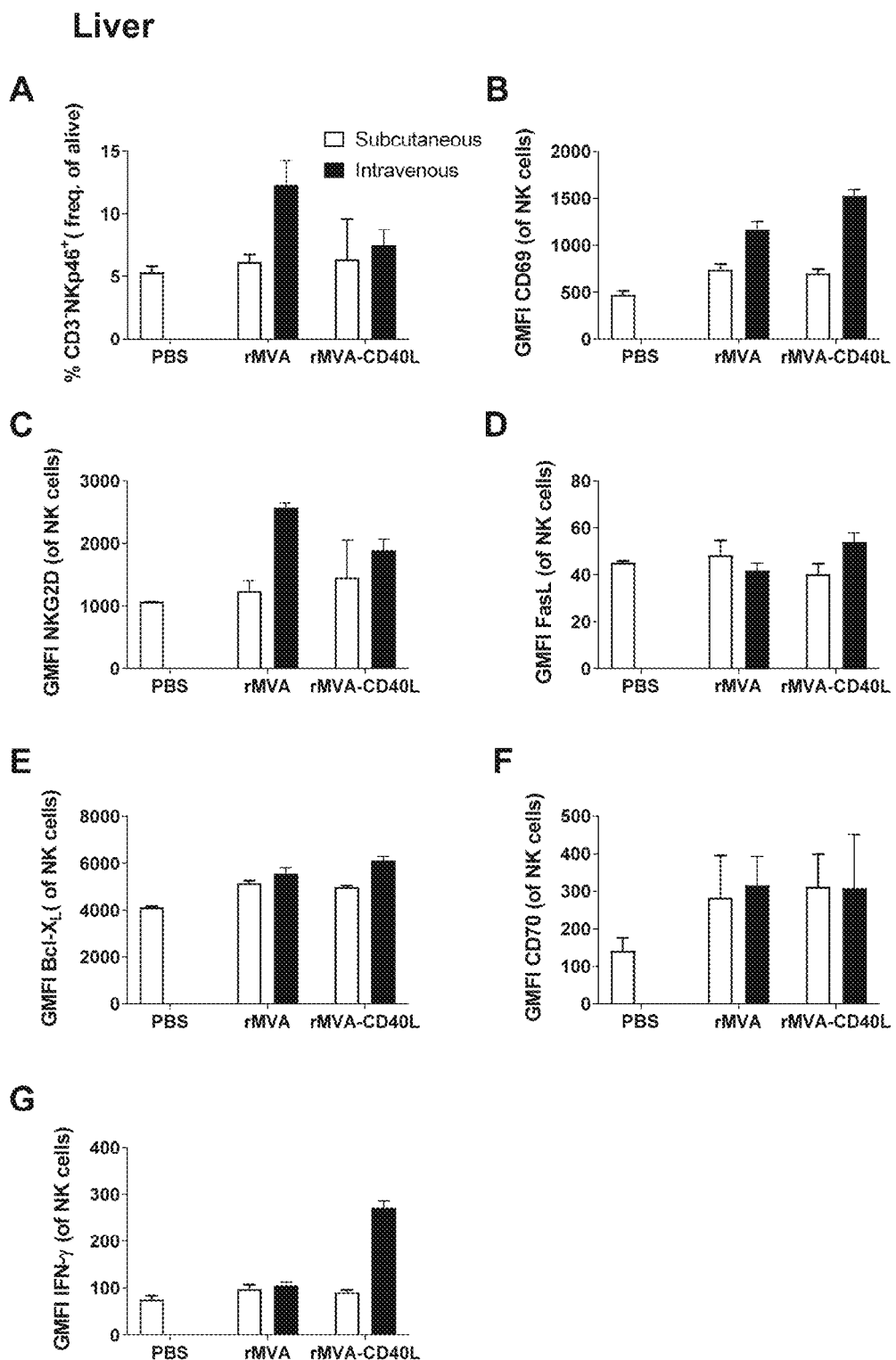
FIGS. 2A-2G show that IV administration of MVA-OVA (rMVA) leads to a stronger systemic activation of NK cells as compared to SC administration. NK cell activation is further enhanced when the MVA encodes CD40L (rMVA-CD40L). Shown are the results of Example 1, wherein staining to assess NK cell frequencies and expression (shown as Geometric Mean Fluorescence Intensity (GMFI)) of the named protein markers in NKp46$^+$CD3$^-$ cells was assessed in the liver.
Figure 3:
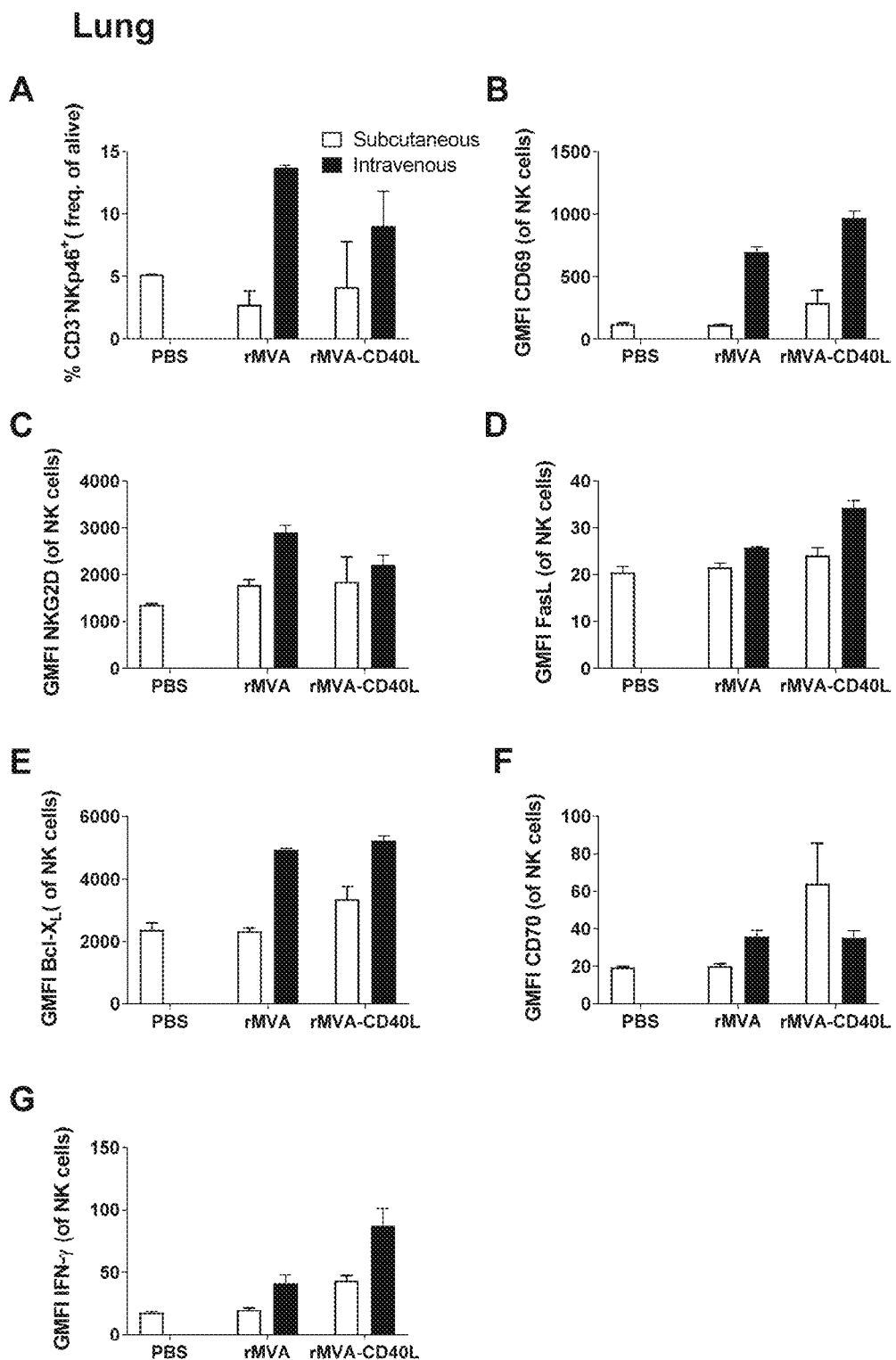
FIGS. 3A-3G show that IV administration of MVA-OVA (rMVA) leads to a stronger systemic activation of NK cells as compared to SC administration. NK cell activation is further enhanced when the MVA encodes CD40L (rMVA-CD40L). Shown are the results of Example 1, wherein staining to assess NK cell frequencies and expression (shown as Geometric Mean Fluorescence Intensity (GMFI)) of the named protein markers in NKp46$^+$CD3$^-$ cells was assessed in the lung.
Figure 4:
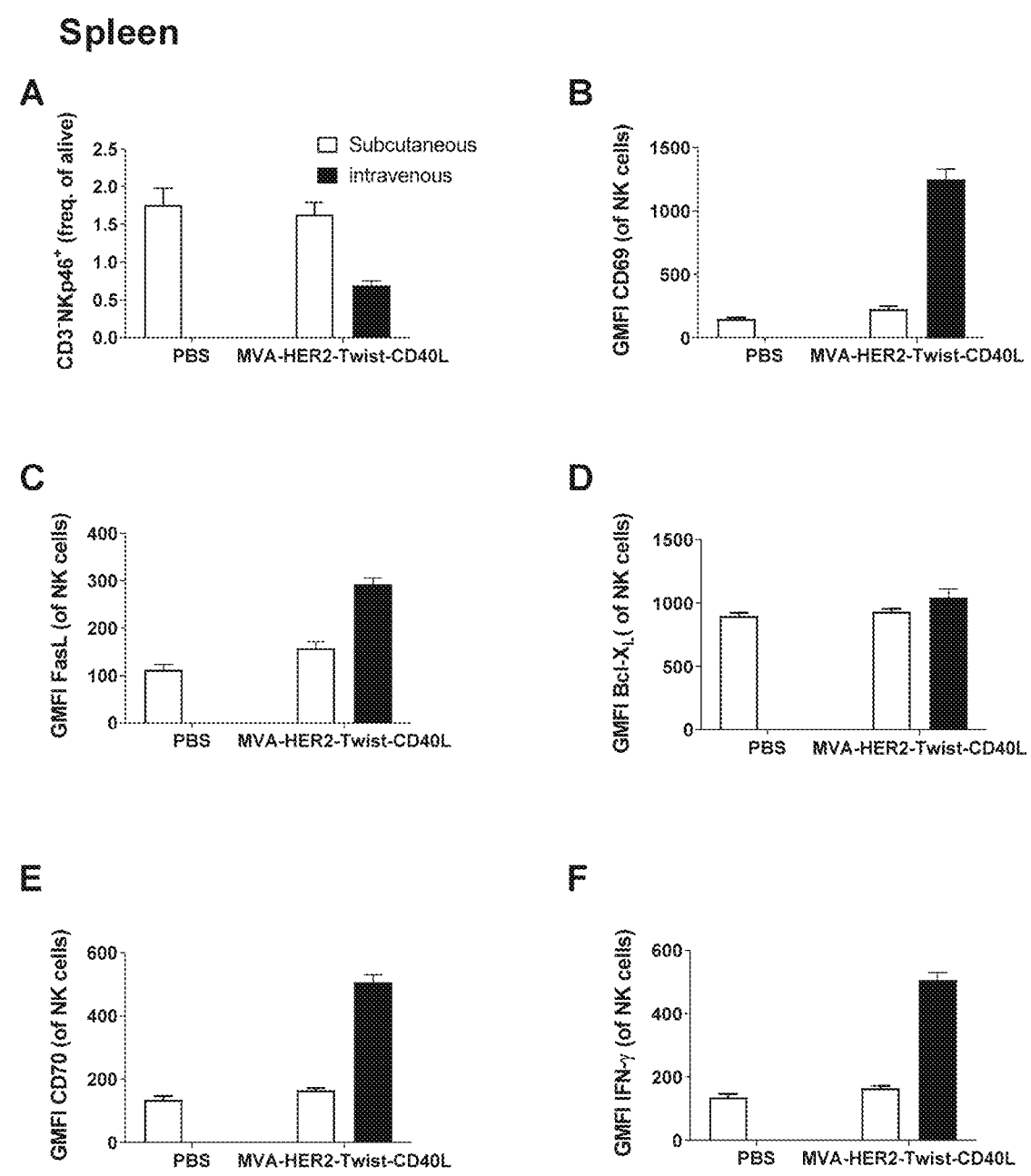
FIGS. 4A-4F show that intravenous (IV) administration of MVA-HER2-Twist-CD40L leads to a stronger systemic activation of NK cells as compared to subcutaneous (SC) administration. Shown are the results of Example 1, wherein staining to assess NK cell frequencies and expression (shown as Geometric Mean Fluorescence Intensity (GMFI)) of the named protein markers in NKp46$^+$CD3$^-$ cells was assessed in the spleen.

It is to be understood that both the foregoing Summary and the following Detailed Description are exemplary and explanatory only and are not restrictive of the invention, as claimed.

Antibody-dependent cellular cytotoxicity (ADCC) is a mechanism of cell-mediated immune defense that enables the immune system to actively lyse and kill target cells that express an antigen or receptor that has been bound by specific antibodies (see Hashimoto et al. (1983) *J. Inf. Dis.* 148: 785-794). ADCC utilizes Natural Killer (NK) cells that interact with antibodies to lyse and kill the target cell (Id). With this in mind, over the past decade therapeutic monoclonal antibodies have been developed which target tumor-associated antigens and function to enhance ADCC and thus the ability to kill tumor cells (see, e.g., Scott et al. (2012) *Cancer Immun.* 12: 14 and Kohrt et al. (2012) *Immunother.* 4: 511-27). While antibody therapies have shown efficacy in enhancing killing of tumor cells through ADCC, it has been shown that tumor cells can evade ADCC and the immune system through a variety of mechanisms such as heterogeneity of tumor antigen expression (e.g., downregulation of tumor antigen expression on the tumor cell surface), antibody stability, low antibody to receptor concentration, receptor saturation, immune suppression for example through regulatory T cells, immune escape and NK cell dysfunction (Scott et al. (2012) *Cancer Immun.* 12: 14). Some aspects of tumor cell evasion have been characterized as the tumor cells entering an "equilibrium phase" with a patient's immune system, whereby tumor cells can remain in the body below the threshold of conventional morphologic, cytogenetic or immune cell recognition (Bhatia et al. (2011) *Cancer Microenvironment* 4: 209-217).

To induce synergistic anti-tumor responses, the various pharmaceutical combinations of the present invention were developed. In several aspects, the various pharmaceutical combinations induce both highly effective tumor specific killer T cells and natural killer (NK) cells that are able to kill tumor cells coated with antibody against tumor expressed receptors through ADCC. In preferred aspects, as described herein, intravenously injecting recombinant MVA encoding CD40L induces an enhanced NK cell activation and drastically increased the kill of antibody-coated tumor cells. This enhanced NK cell activation when combined with the enhanced killer T cell response also induced by the MVA, is shown to act synergistically in therapeutic tumor vaccination.

In various additional aspects, the embodiments of the present invention induce an immune response that has enhanced and/or increased ability to target and kill those tumor and cancer cells that evade a patient's immune system. In further aspects, the embodiments of the present invention induce an immune response that enhances and/or increases the efficacy of both a patient's innate and adaptive immune responses. Being able to enhance and/or increase both the innate and adaptive immune responses is particularly advantageous as the present invention can target and kill those tumor cells that evade and/or suppress a patient's adaptive immune response as well as those tumor cells that evade and/or suppress a patient's innate immune response.

In one embodiment, the present invention is a combination therapy comprising: a) an intravenous (IV) administration of a recombinant MVA that comprises a nucleic acid encoding one or more heterologous tumor associated antigens (TAA), and b) an antibody, wherein the antibody comprises an Fc domain and is specific for an antigen expressed on a tumor cell. In another embodiment, the combination therapy further comprises an IV administration of CD40L. In a preferred embodiment, the CD40L is encoded by the recombinant MVA.

Described and illustrated in the present application, the pharmaceutical combination and/or combination therapy of the present invention enhances multiple aspects of a cancer patient's immune response. In at least one aspect, the pharmaceutical combination synergistically enhances both the innate and adaptive immune responses to reduce tumor volume and increase survival of a cancer patient. One or more of the enhanced effects of the pharmaceutical combination and/or therapy are summarized as follows.

IV administration of recombinant MVA enhances NK cell response. In one aspect, the present invention includes a recombinant MVA administered intravenously to a subject, wherein the IV administration induces an enhanced innate immune response, more particularly an enhanced NK cell response in the subject as compared to a NK cell response induced by a non-IV administration of a recombinant MVA to the subject. Shown in FIGS. 1A-9 and 13, IV administration of recombinant MVA induced a robust systemic NK cell response in several compartments in both a single IV administration and when administered intravenously as a homologous prime-boost, as compared to a non-IV administration.

Illustrated in FIGS. 1A-6F, the quality of the NK cell response was enhanced as compared to a non-IV administration. The activation marker CD69 is increased in all organs analyzed (spleen, liver and lung). The anti-apoptotic Bcl-family member Bcl-$X_L$, that enhances NK cell survival, co-stimulatory CD70 and the effector cytokine IFN-γ were increased both in spleen and lung. Expression of the activating Natural Killer Group 2D (NKG2D) receptor was especially enhanced in liver and lung after IV compared to SC injection. NKG2D binds to ligands on tumor cells promoting their elimination (Garcia-Cuesta et al. (2015) *Front. Immunol.* 6: 284, reviewed in Spear et al. (2013) *Cancer Immun.* 13: 8).

Figure 5:
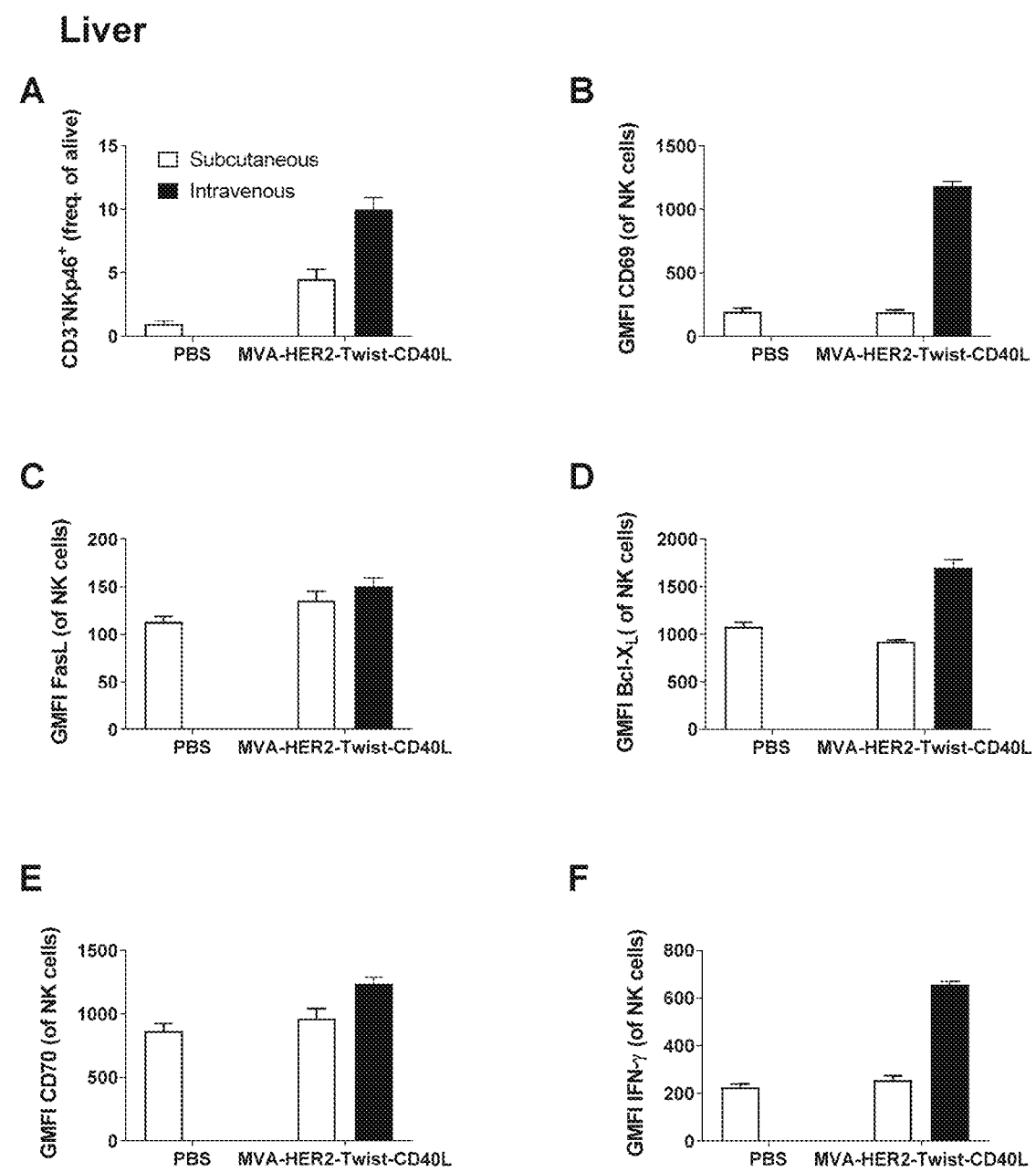
FIGS. 5A-5F show that IV administration of MVA-HER2-Twist-CD40L leads to a stronger systemic activation of NK cells as compared to SC administration. Shown are the results of Example 1, wherein staining to assess NK cell frequencies and expression (shown as Geometric Mean Fluorescence Intensity (GMFI)) of the named protein markers in NKp46$^+$CD3$^-$ cells was assessed in the liver.
Figure 6:
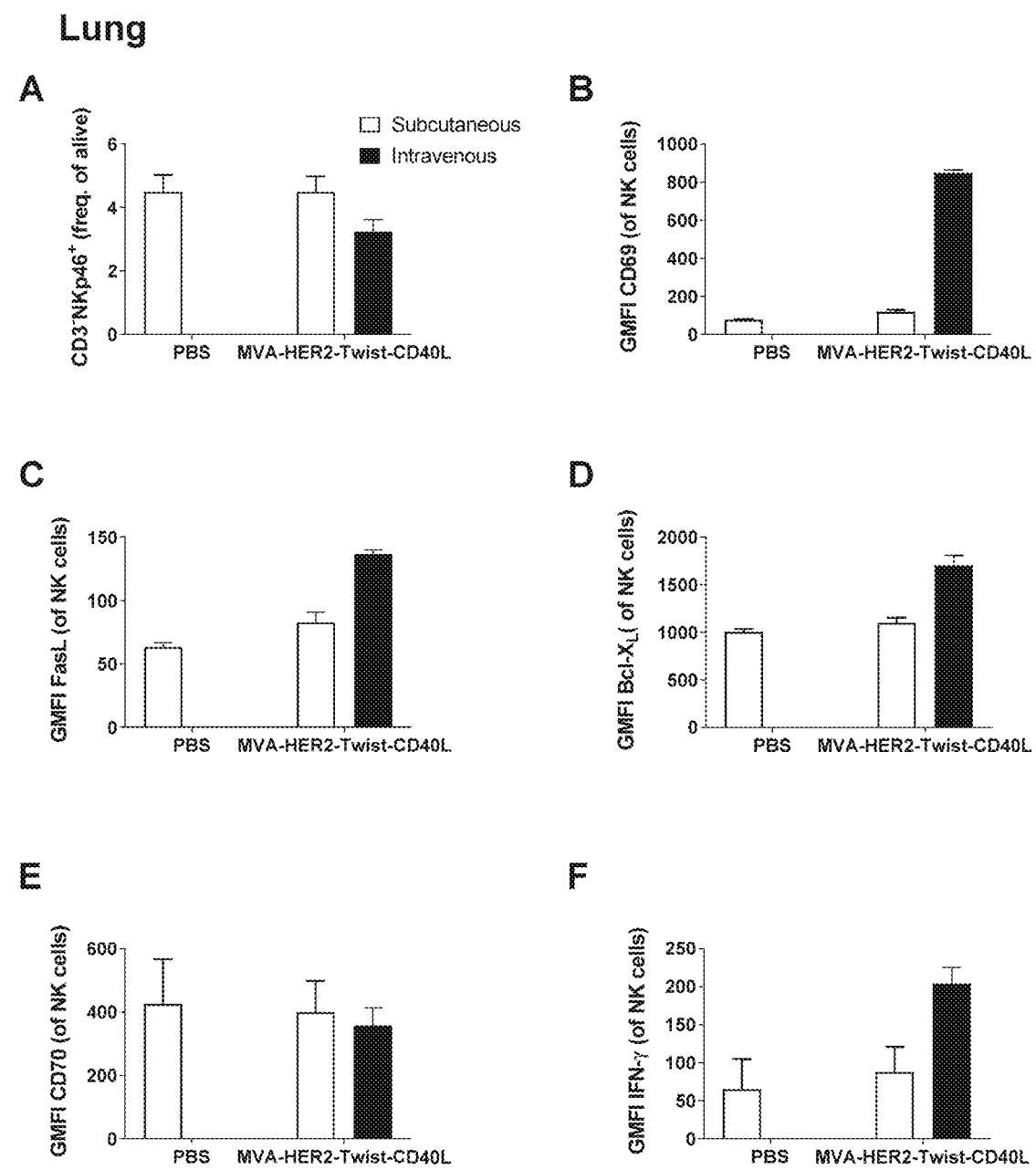
FIGS. 6A-6F show that IV administration of MVA-HER2-Twist-CD40L leads to a stronger systemic activation of NK cells as compared to SC administration. Shown are the results of Example 1, wherein staining to assess NK cell frequencies and expression (shown as Geometric Mean Fluorescence Intensity (GMFI)) of the named protein markers in NKp46$^+$CD3$^-$ cells) was assessed in the lung.
Figure 7:
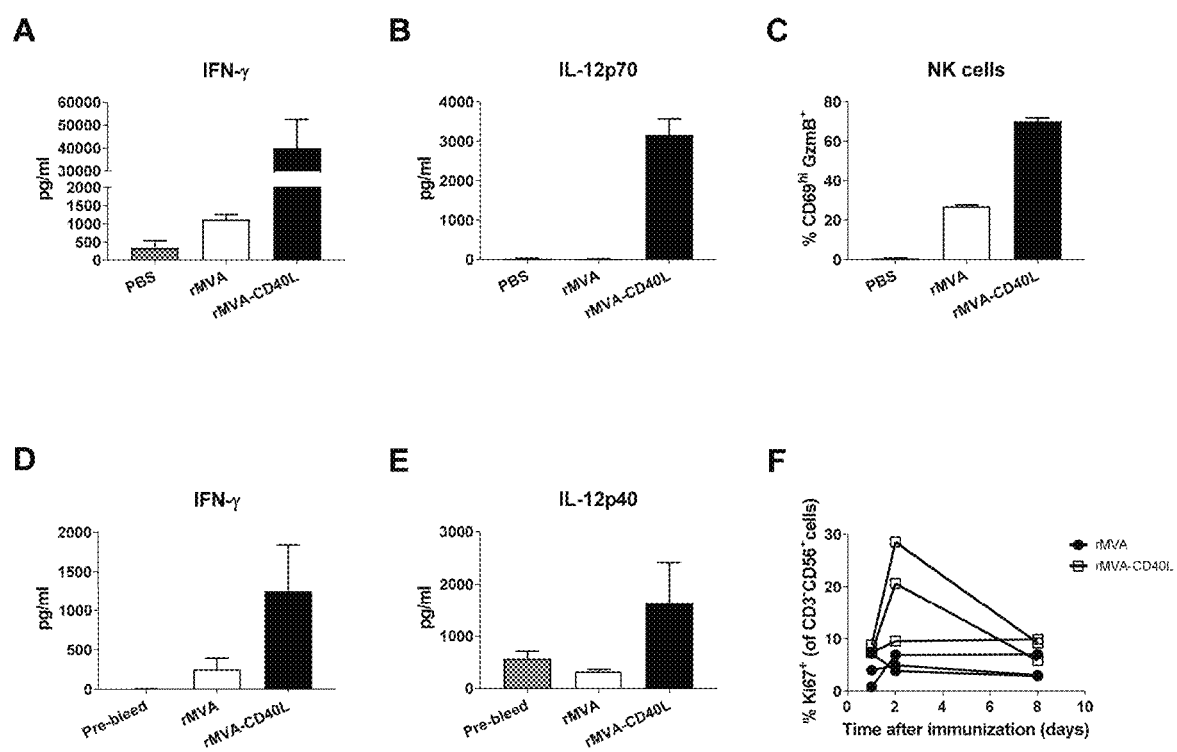
FIGS. 7A-7F show that IV administration of MVA-OVA-CD40L (rMVA-CD40L) leads to enhanced levels of IL-12p70 and IFN-γ. Shown are the results of Example 2.
Figure 8:
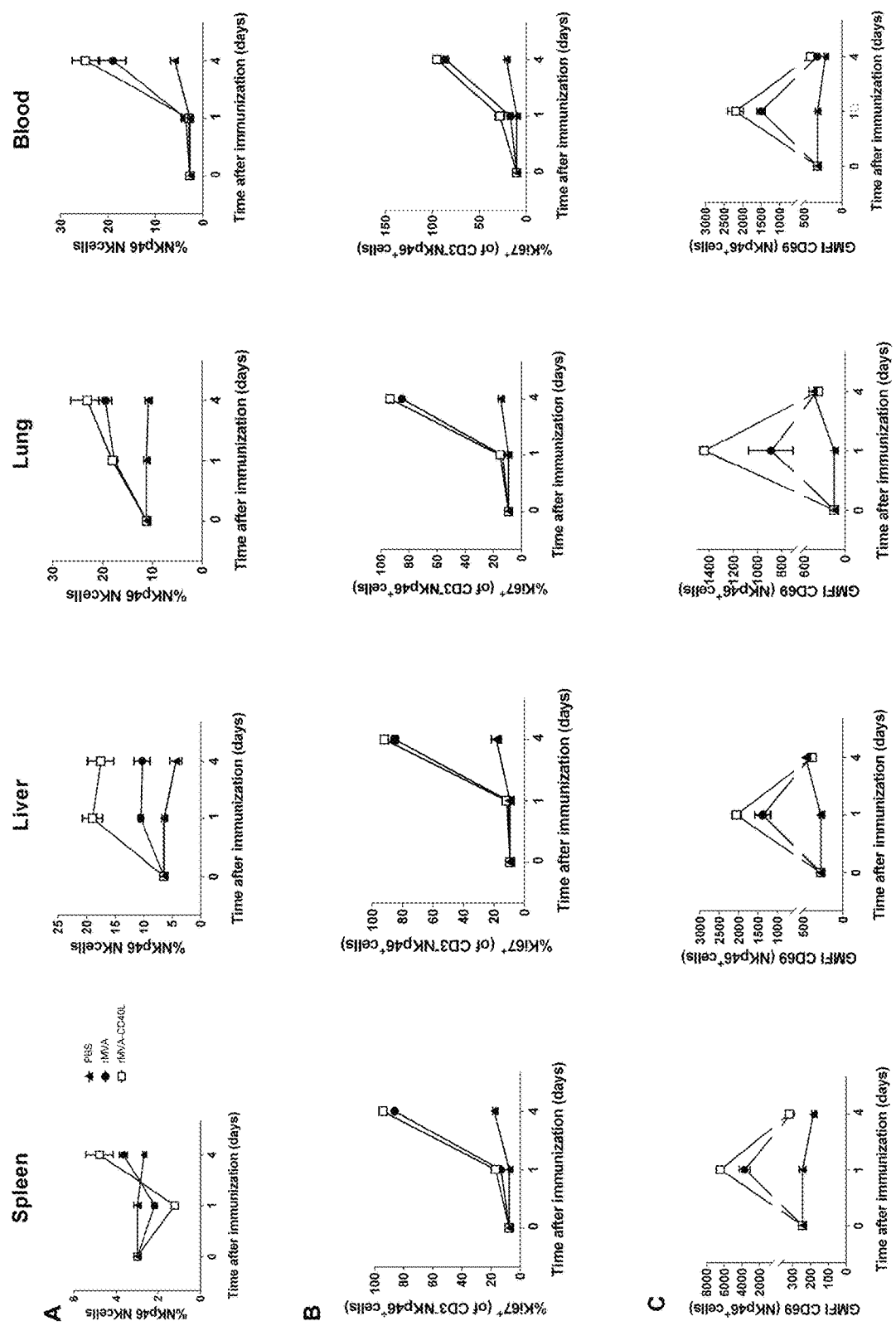
FIGS. 8A-8C show a time course of NK cell activation and proliferation. Shown are the results of Example 3, wherein staining to assess NK cell frequencies and expression of the named protein markers in NKp46$^+$CD3$^-$ cells was assessed in the spleen, liver, lung and blood.
Figure 9:
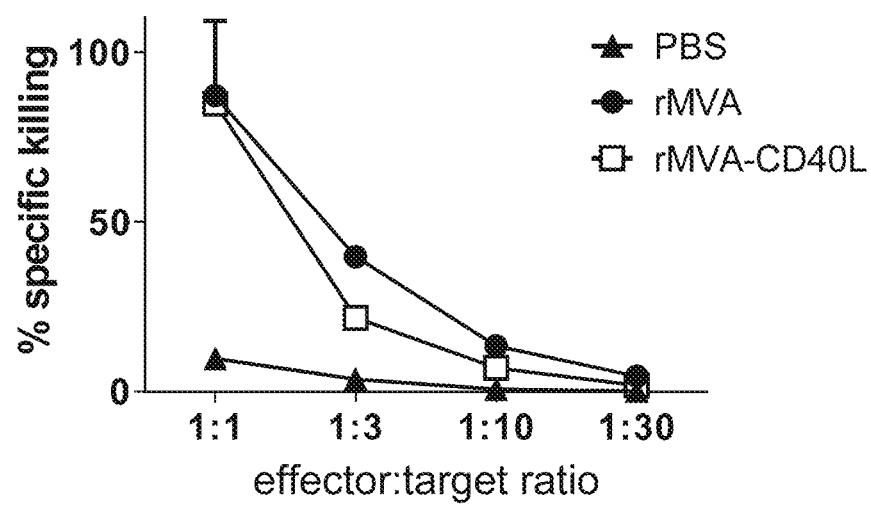
FIG. 9 shows enhanced NK cell mediated toxicity ex vivo upon systemic MVA-OVA (rMVA) and MVA-CD40L (rMVA-CD40L) immunization. Splenic NK cells were purified and used as effectors in a target killing assay as described in Example 4. NK cells were cultured with CFSE-labelled MHC class I-deficient YAC-1 cells at the indicated ratios overnight. Specific killing was assessed by quantifying unviable CFSE$^+$ YAC-1 cells by flow cytometry.
Figure 10:
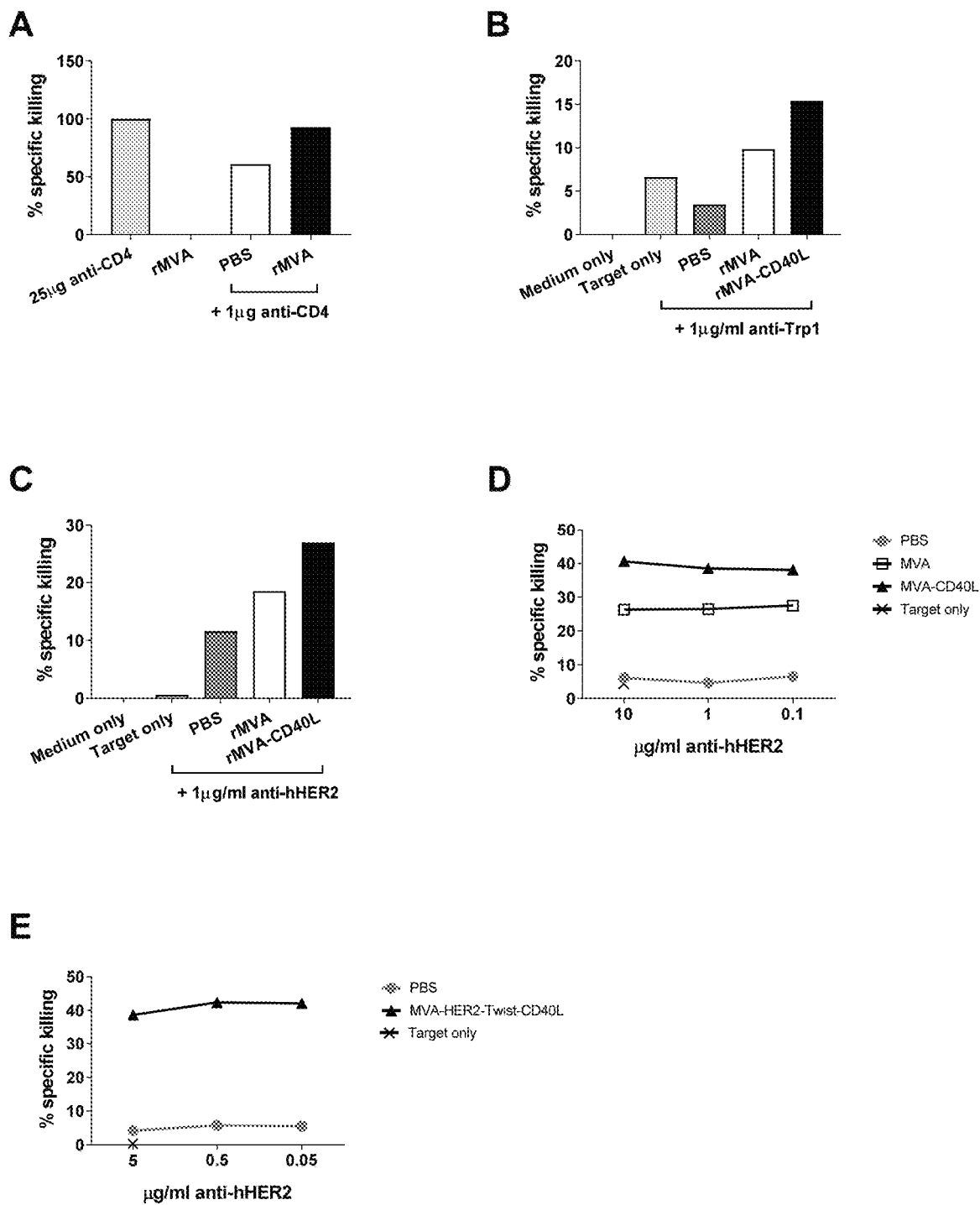
FIGS. 10A-10E show enhanced antibody-dependent cellular cytotoxicity (ADCC) in vivo and ex vivo upon systemic MVA-OVA (rMVA), MVA-CD40L (rMVA-CD40L), and MVA-HER2-Twist-CD40L immunization as described in Example 5.

IV administration of recombinant MVA encoding CD40L further enhances NK cell response. In another aspect of the present invention it was determined that an IV administration of the CD40L antigen in addition to the recombinant MVA further enhanced the NK cell response as compared to an IV administration of recombinant MVA alone. As illustrated in FIGS. 1A-9 and 13A-13B, a recombinant MVA encoding a CD40L antigen induced a stronger NK cell response as compared to a recombinant MVA without CD40L in both a single administration and when administered as a homologous prime boost. Further, the quality of the NK cell response was enhanced as compared to the IV administration of the recombinant MVA alone. Increased expression by NK cells of the effector cytokine IFN-γ was observed in all organs analyzed (FIGS. 1A-6F, spleen, liver, lung), as well as expression of CD69 by NK cells in all organs analyzed (FIG. 5C). Moreover, FIG. 7A-7F shows increased serum levels 6 hours after IV immunization with rMVA-CD40L compared to recombinant MVA of IFN-γ and, more importantly, the NK activating cytokine IL-12p70, both in mice and NHPs. In addition, enhanced proliferation of NK cells, demonstrated by the expression of Ki67, was observed not only systemically in mice (FIG. 7B) but also in NHP peripheral blood (FIG. 6F). These results show that IV immunization of rMVA-CD40L compared to rMVA improves NK cell quality in several animal research models.

While recombinant MVA viruses have been previously administered intravenously (see, e.g., WO2002/42480 and WO2014/037124), it was previously understood that recombinant MVA administration and treatment was associated with enhancement of an adaptive immune response, such as CD8 T cell responses. For example, in WO2002/42480, CTL responses were measured after immunizations using MVA were done either by IV administration of $10^7$ pfu MVA-BN per mouse, or by subcutaneous administration of $10^7$ pfu or $10^8$ pfu MVA-BN per mouse. In WO2014/037124, mice were intravenously inoculated with recombinant MVA and recombinant MVA encoding CD40L (see WO2014/037124). CTL responses were enhanced and it was determined that an increased immunogenicity of the recombinant MVA-CD40L was independent of $CD4^+$ T cells but dependent upon CD40 in the host.

In at least one aspect, the enhanced NK cell response seen by the present invention is unexpected as it was understood in the art that MVA-induced NK cell activation was shown to be dependent on lymph node-resident CD169-positive subcapsular sinus (SCS) macrophages after subcutaneous immunization (Garcia et al. (2012) *Blood* 120: 4744-50).

IV administration of recombinant MVA enhances ADCC of tumor cells. In a further aspect, the present invention includes a recombinant MVA comprising a nucleic acid encoding one or more heterologous antigens, wherein an IV administration to a subject enhances an ADCC response in the subject as compared to an ADCC response from a non-IV administration of a recombinant MVA to the subject. In a more specific aspect, the enhancement of the ADCC response resulting from an IV administration of recombinant MVA is characterized by an increase in NK cells' ability to target and kill antibody-coated tumor cells. Illustrated in FIGS. 10A-10D, cell lysis of tumor cells presenting a mouse anti-human HER2 mAb or a mouse anti-human/mouse Trp1 mAb was increased for NK cells activated by an IV rMVA administration. Cell lysis of tumor cells was even further increased for NK cells activated by a recombinant MVA together with CD40L as compared to rMVA without CD40L.

Illustrated in FIGS. 10D and 10E, the enhancement of an ADCC response in the subject is additionally characterized as increasing the efficacy of the NK cell response such that the NK cells are able to target and kill tumor cells whose antibody bound to tumor antigen (antibody-tumor antigen) concentration is lower. Being able to target and kill tumor cells with decreased concentrations of antibody-coated tumor antigen is particularly advantageous, as one of the mechanisms by which tumor cells have been shown to evade the immune system is through downregulation of tumor antigen expression (see Scott et al. (2012) *Cancer Immun.* 12: 14); which decreases the concentration of antibody-tumor antigen on tumor cells.

IV administration of recombinant MVA enhances NK cell killing of tumor cells having low MHC levels. In a further aspect, illustrated in FIG. 9, the enhanced NK cell activation and NK cell response results in an enhanced killing of tumor cells having low levels of MHC. This aspect is particularly advantageous as NK cell killing of low MHC tumor cells occurs independently of ADCC, thereby adding an additional pathway to attack the tumor cells. This is additionally advantageous as many tumors and/or cancers lower MHC expression levels in attempting to evade a patient's immune responses.

IV administration of recombinant MVA boosts NK cell activation and proliferation. In another aspect of the present invention, a recombinant MVA is administered in multiple boosts and results in increased NK cell activation and proliferation demonstrated in FIG. 10A by means of enhanced CD69 expression. FIG. 13B shows increased proliferative capacity of blood NK cells by means of Ki67 expression 24 hours after boost IV immunizations compared to no IV immunization. This effect was observed when a recombinant MVA prime immunization was boosted with recombinant MVA, when a recombinant MVA-CD40L was boosted with rMVA-CD40L, or when rMVA prime immunization was boosted with rMVA-CD40L.

Figure 14:
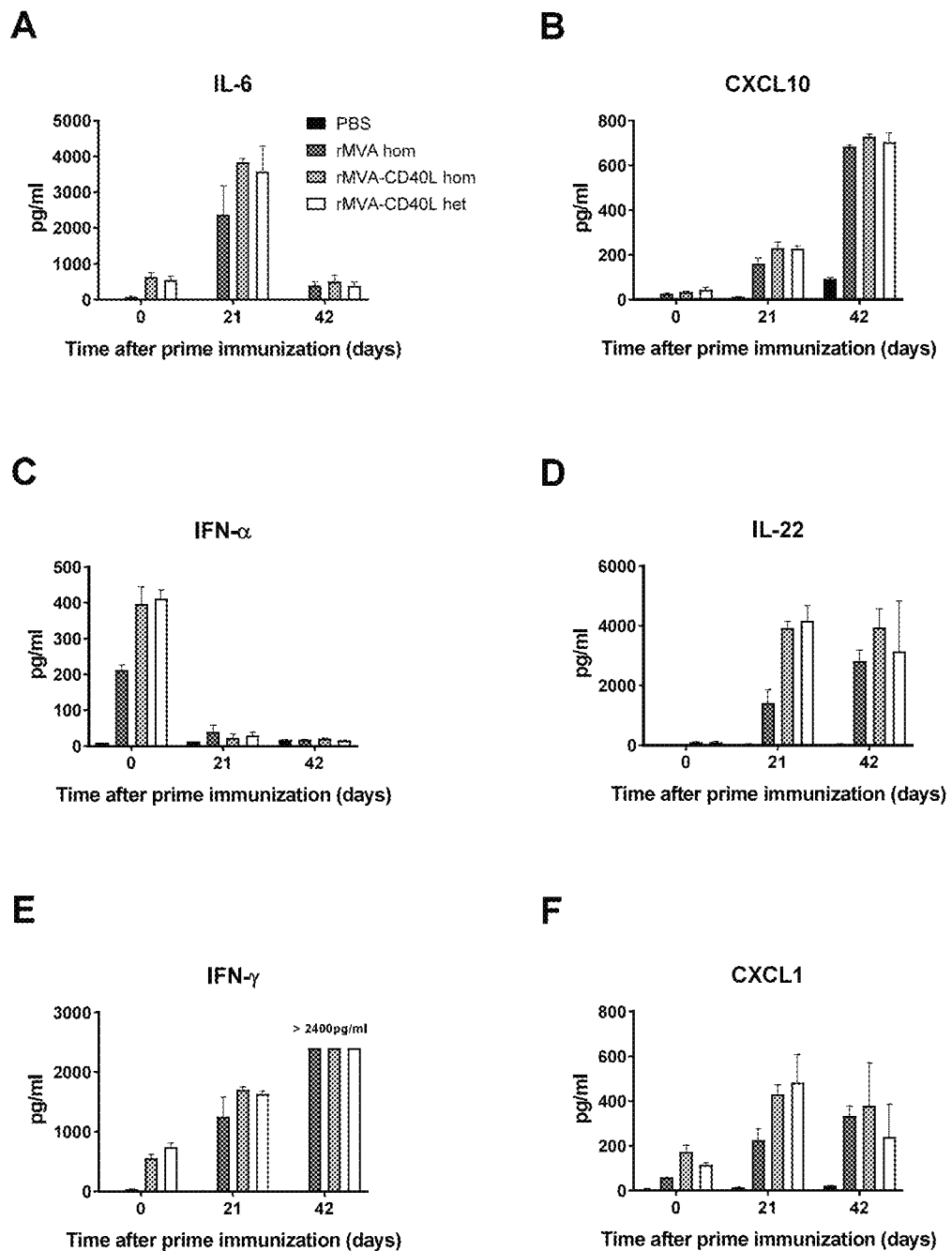
FIGS. 14A-14M show systemic cytokine responses after prime/boost immunization. Described in Example 9, C57BL/6 mice were immunized IV (intravenously) either with PBS, MVA-OVA (rMVA), or MVA-OVA-CD40L (rMVA-CD40L) as shown in Table 1. Serum cytokine levels were measured at 6 hours post immunization. Shown are the results, in FIG. 14A: IL-6.
Figure 14:
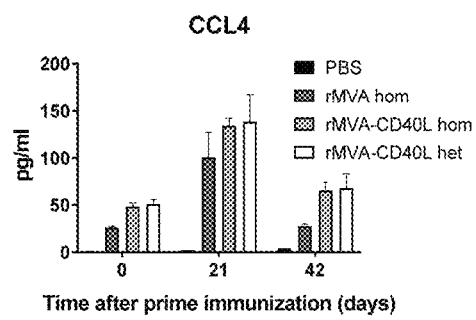
Figure 14:
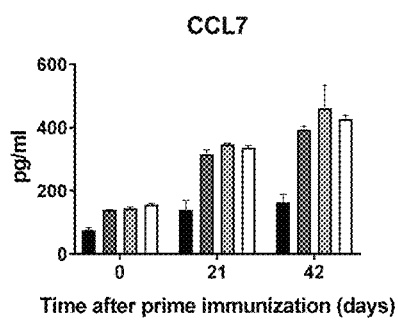
Figure 14:
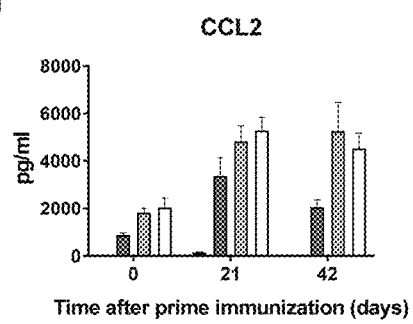
Figure 14:
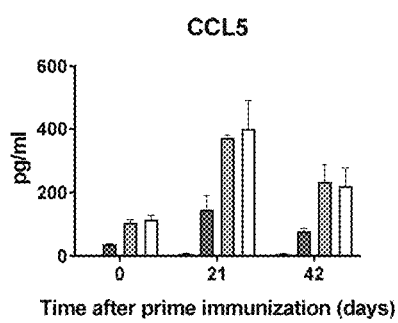
Figure 14:
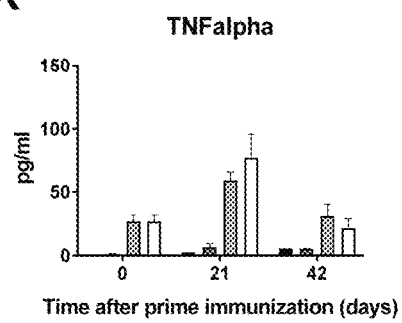
Figure 14:
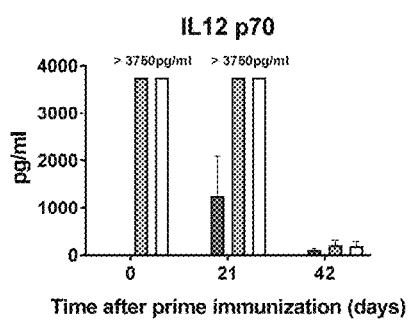
Figure 14:
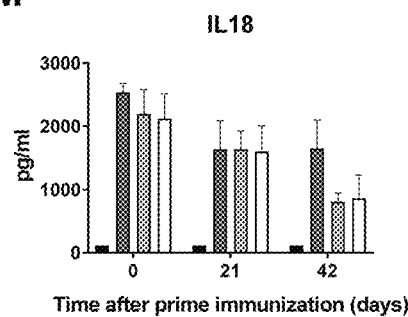

In at least one aspect of the present invention, the enhanced NK cell responses resulting from the repeated recombinant MVA IV administration and the recombinant MVA-CD40L were unexpected. It was unexpected to observe increased NK cell activation and proliferation 24 hours after boost IV immunizations in the absence of an IFN-α increase. Indeed, it was understood that NK cell activation and priming in secondary infections and cancer is largely driven by IFN-α (see, e.g., Stackaruk et al. (2013) *Expert Rev. Vaccines* 12(8): 875-84; and Muller et al. (2017) *Front. Immunol.* 8: 304). Unexpectedly, no increase in IFN-α serum levels were observed 6 hours after rMVA hom, rMVA-CD40L hom or rMVA-CD40L het IV boost immunizations (FIG. 14C). Altogether, repeated homologous or heterologous IV immunizations with rMVA comprising a nucleic acid encoding one or more heterologous antigens resulted in unexpected NK cell activation and proliferation independent of IFN-α.

Figure 11:
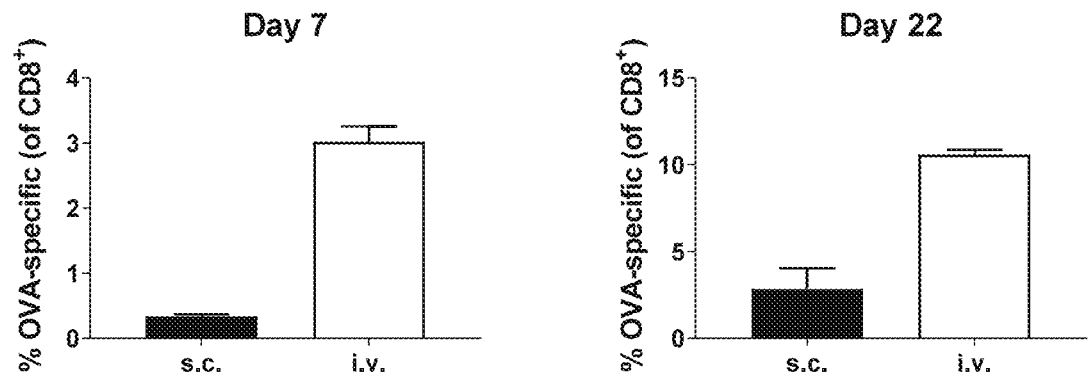
FIG. 11 shows that IV immunization induces stronger CD8 T cell responses than SC immunization. Described in Example 6, C57BL/6 mice were immunized either SC or IV with MVA-OVA on days 0 and 15. OVA-specific CD8 T cell responses in the blood were assessed after staining with H-2K$^b$/OVA$_{257-264}$ dextramers.
Figure 12:
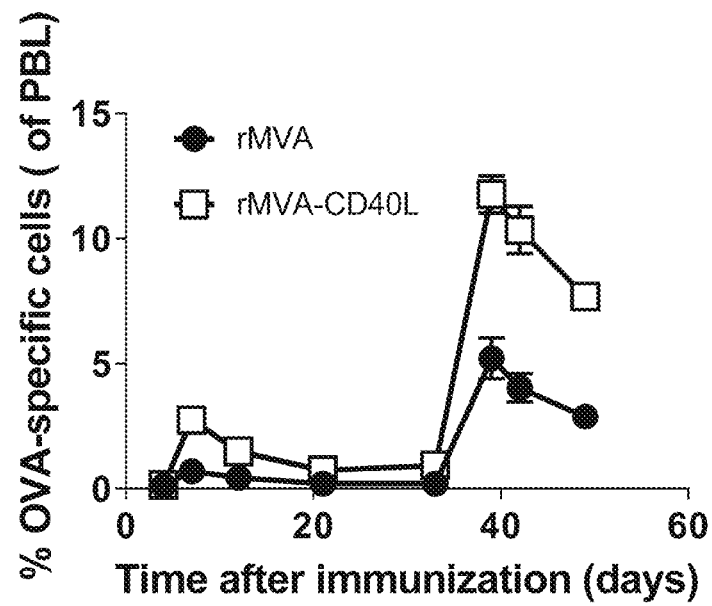
FIG. 12 shows that CD8 T cell responses can be further enhanced by MVA-CD40L. Described in Example 7, C57BL/6 mice were immunized IV with MVA-OVA (rMVA) or MVA-OVA-CD40L (rMVA-CD40L) on days 0 and 35. OVA-specific CD8 T cell responses in the blood were assessed after staining with H-2K$^b$/OVA$_{257-264}$ dextramers.
Figure 13:
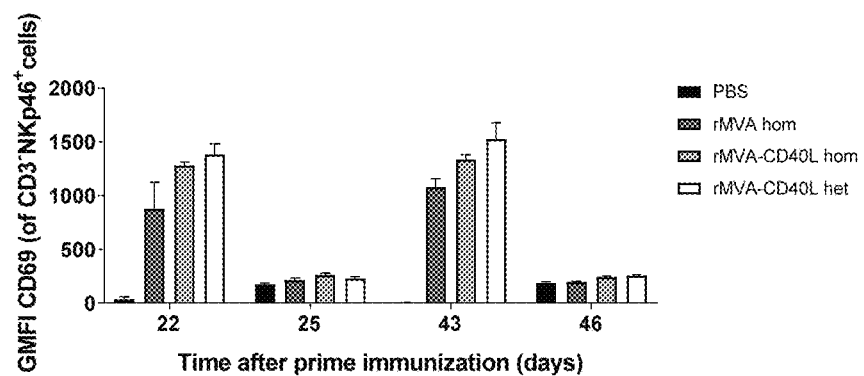
FIGS. 13A-13B shows repeated NK cell activation and proliferation after prime/boost immunization. Described in Example 8, C57BL/6 mice were immunized IV either with PBS, MVA-OVA (rMVA) or MVA-OVA-CD40L (rMVA-CD40L) as shown in Table 1. NK cells (NKp46$^+$CD3$^-$) were analyzed in the blood by flow cytometry one and four days after second and third immunization.
Figure 13:
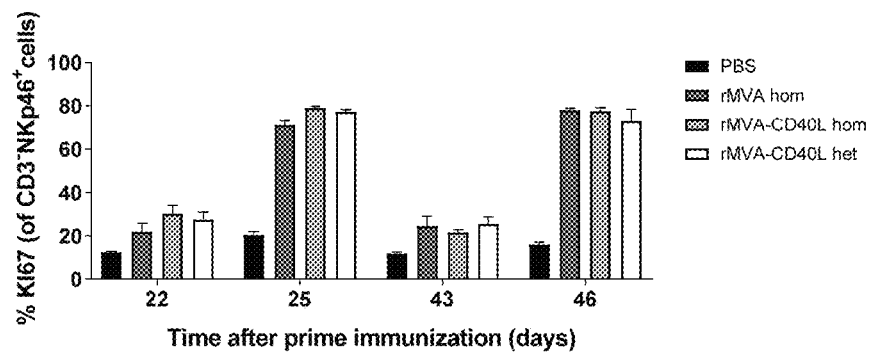

IV administration of recombinant MVA encoding a heterologous antigen enhances a cancer patient's adaptive immune response. In another aspect of the present invention, there is a recombinant MVA comprising a nucleic acid encoding one or more heterologous antigens, wherein an IV administration to the subject enhances the subject's adaptive immune response to the one or more heterologous antigens. In a preferred aspect, the recombinant MVA further encodes CD40L. Illustrated in FIGS. 11-12, an IV administration of the recombinant MVA expressing a heterologous antigen produced a stronger CTL response as compared to a subcutaneous (SC) administration. Also, illustrated in the Figures, when CD40L is included as part of the recombinant MVA, an IV administration of the recombinant MVA antigen produced a stronger CTL response as compared to an IV administration of a recombinant MVA without CD40L.

Figure 15:
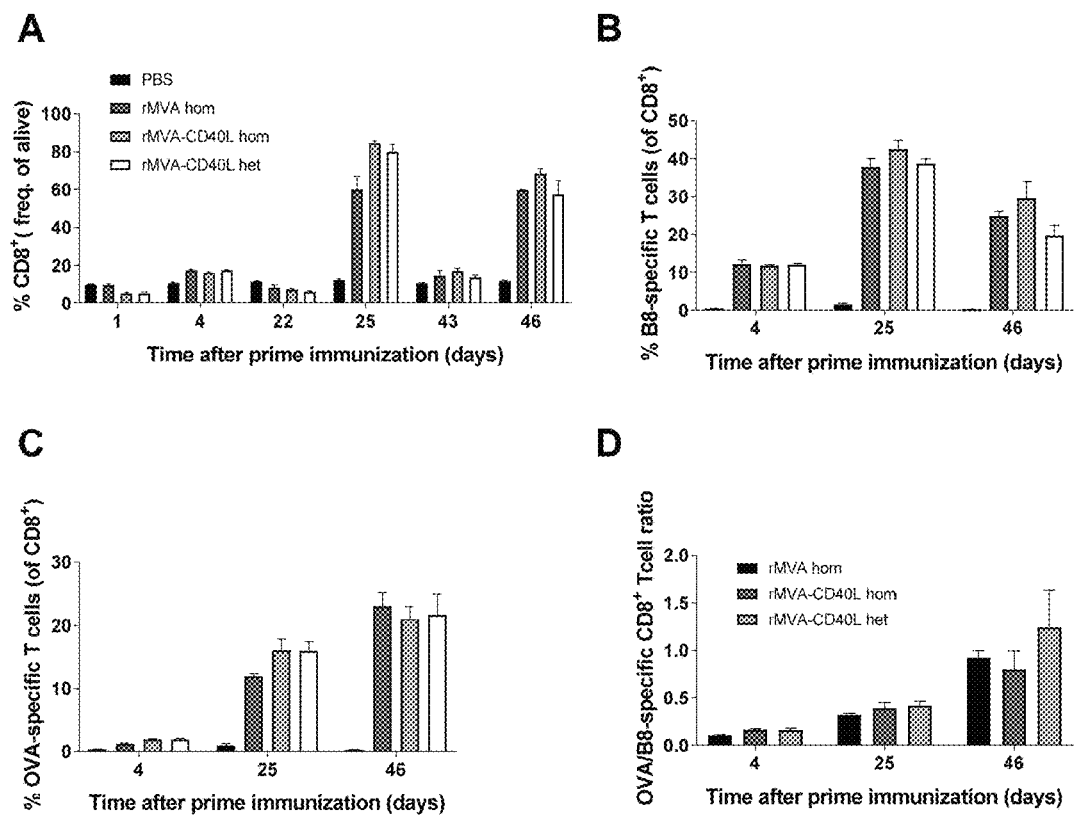
FIGS. 15A-15D show strong antigen-specific CD8 T cell responses after MVA and MVA-CD40L prime/boost immunization. Described in Example 10, C57BL/6 mice were immunized IV either with PBS, MVA-OVA (rMVA) or MVA-OVA-CD40L (rMVA-CD40L) as shown in Table 1. Induction of antigen-specific CD8 T cell responses after repetitive immunization was assessed.
Figure 16:
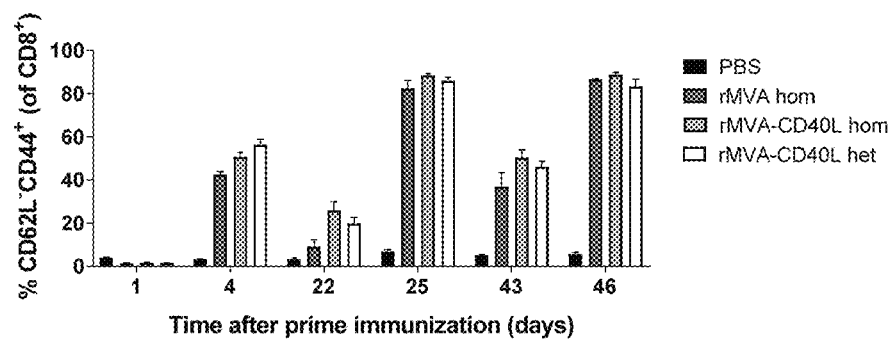
FIGS. 16A-16B show CD8 and CD4 effector T cell induction after MVA and MVA-CD40L prime/boost immunization. Described in Example 11, C57BL/6 mice were immunized IV either with PBS, MVA-OVA (rMVA) or MVA-OVA-CD40L (rMVA-CD40L) as shown in Table 1. Phenotypically, effector T cells were identified by the expression of CD44 and the lack of surface CD62L.
Figure 16:
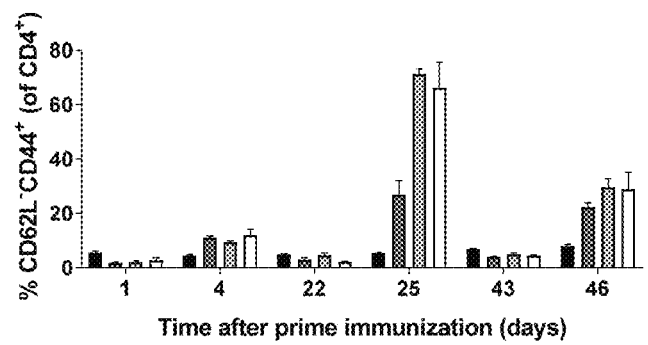

Further, illustrated in FIGS. 14A-16B, when recombinant MVA encoding a heterologous antigen and a CD40L were administered intravenously the quality of the T-cell response was enhanced after IV boost immunizations. FIG. 15 shows increased MVA antigen, B8(FIG. 15B) and heterologous antigen, OVA (FIG. 15C) specific CD8 T cell expansion enhanced with boost IV immunizations. This effect is linked to the cytokine and chemokine expression pattern observed in FIG. 14, where the T cell activating cytokines CXCL10, IFN-γ, CXCL1, CCL4, CCL7, CCL2, CCL5, TNF-α, IL-12p70, and IL-18 are quantified in the serum after IV boosts. In line with this, FIGS. 16A and 16B show the expansion of memory T cells, a key feature of vaccines, after boost IV immunizations. The ratio of CD8 T cells specific for the heterologous antigen to MVA antigen-specific CD8 T cells increased with each immunization (FIG. 15D).

Prior to the present invention, it was understood that CD40L encoded by recombinant MVA can substitute for CD4 T cell help (Lauterbach et al. (2013) *Front. Immunol.* 4: 251). Further, no effect of recombinant MVA-encoded CD40L on CD4 T cells was known. Unexpectedly, we saw expansion of memory CD4$^+$ T cells 25 days after prime immunization (FIG. 16B), which corresponds with 4 days after boost IV immunization with rMVA-CD40L (rMVA-CD40L horn and rMVA-CD40L het) (Day 21, see Table 1). This fact is supported by the increased IL-22 production, an important cytokine indicative of T helper cell responses, quantified 6 hours after boost IV immunization in MVA-CD40L horn and MVA-CD40L het groups (FIG. 14D). This unexpected observation is relevant for the maintenance of memory responses by rMVA-CD40L. Furthermore, CD4 T cells can support tumor-specific CD8 T cells at the tumor site, avoid activation-induced cell death and also become cytotoxic themselves (reviewed in Kennedy and Celis (2008) *Immunol. Rev.* 222: 129-44; Knutson and Disis (2005) *Curr. Drug Targets Immune Endocr. Metabol. Disord.* 5: 365-71). These results are unexpected because other viral vectors, such as Adenovirus and Herpes Simplex Virus, induce vector-specific immunity that impede the induction of immune responses to the vaccine-encoded antigens upon boost immunization (Lauterbach et al. (2005) *J. Gen. Virol.* 86: 2401-10; Pine et al. (2011) *PLoS One* 6: e18526).

IV Administration of recombinant MVA at the same as or after administration of an antibody increases effectiveness of tumor cell killing. In still further aspects, the present disclosure provides for one or more regimens for administration of the pharmaceutical combination of the present invention to a subject. In at least one aspect, the regimens of the present invention increase the effectiveness of the pharmaceutical combination and/or therapy to enhance ADCC-mediated killing of the tumor cells. In one embodiment, a regimen of administration of the pharmaceutical combination comprises a) administering an antibody as described herein, and b) at the same time or after the antibody administration, intravenously administering a recombinant MVA of the present invention to the subject.

In one advantageous aspect of the present invention, administering the recombinant MVA at the same time or after the antibody enables administered antibody to bind tumor cells at the same time or prior to enhancement of the NK cell response that results from administering the recombinant MVA. Accordingly, in an exemplary first step, an antibody is administered resulting in the antibody binding to the tumor or disease infected cells. In an exemplary second step, recombinant MVA is intravenously administered which, as described herein, enhances and increases the subject's NK cell response. The enhanced NK cell response then aggressively targets and kills tumor cells having the bound antibody.

In other aspects, the pharmaceutical combination of the present invention is administered as part of a homologous and/or heterologous prime-boost regimen. Illustrated in FIGS. 11-16B, a homologous and/or heterologous prime boost regimen prolongs and reactivates enhanced NK cell responses as well as increases a subject's specific CD8 and CD4 T cell responses.

IV administration of recombinant MVA enhances anti-tumor effects. In another aspect of the present invention, there is a recombinant MVA comprising a nucleic acid encoding one or more heterologous antigens, wherein an IV administration to the subject results in an increase in the survival rate of the subject as well as a reduction in the overall tumor volume, as compared to a non-IV administration. In a preferred aspect, the recombinant MVA further encodes CD40L. Illustrated in FIGS. 17A-17B and 18, an IV administration of the recombinant MVA resulted in a greater overall survival rate and a greater reduction in tumor volume or a longer control of tumor growth as compared to a SC administration. Also illustrated, CD40L included as part of the recombinant MVA produced an improved overall survival and tumor reduction as compared to an IV administration of a recombinant MVA without CD40L. Illustrated in FIG. 19A-19C, CD40L included as part of the recombinant MVA increased total CD8 and antigen (OVA)-specific T cell accumulation in peripheral blood of tumor bearers compared to an IV administration of a recombinant MVA without CD40L. In addition, CD8 T cells are critical mediators of rMVA-CD40L anti-tumor effect, since antibody-mediated depletion of CD8 cells results in lack of prolonged overall survival.

IV administration of MVA encoding for two heterologous antigens increases anti-tumor efficacy. In another aspect of the present invention illustrated in FIG. 20A-20C, IV immunization utilizing MVA encoding for two heterologous antigens (OVA and TRP2) induces prolonged tumor growth control and increases overall survival. CD40L included as part of the recombinant MVA encoding for two heterologous antigens enhances the anti-tumor response compared to an IV administration of a recombinant MVA with CD40L and only one heterologous antigen. Since cancers utilize diverse mechanisms of immune escape as downregulation of tumor antigens (Jensen et al. (2012) *Cancer* 118: 2476-85), encoding two or more tumor antigens in the vaccine limits the development of escape mechanisms to the anti-tumor immune response.

Figure 21:
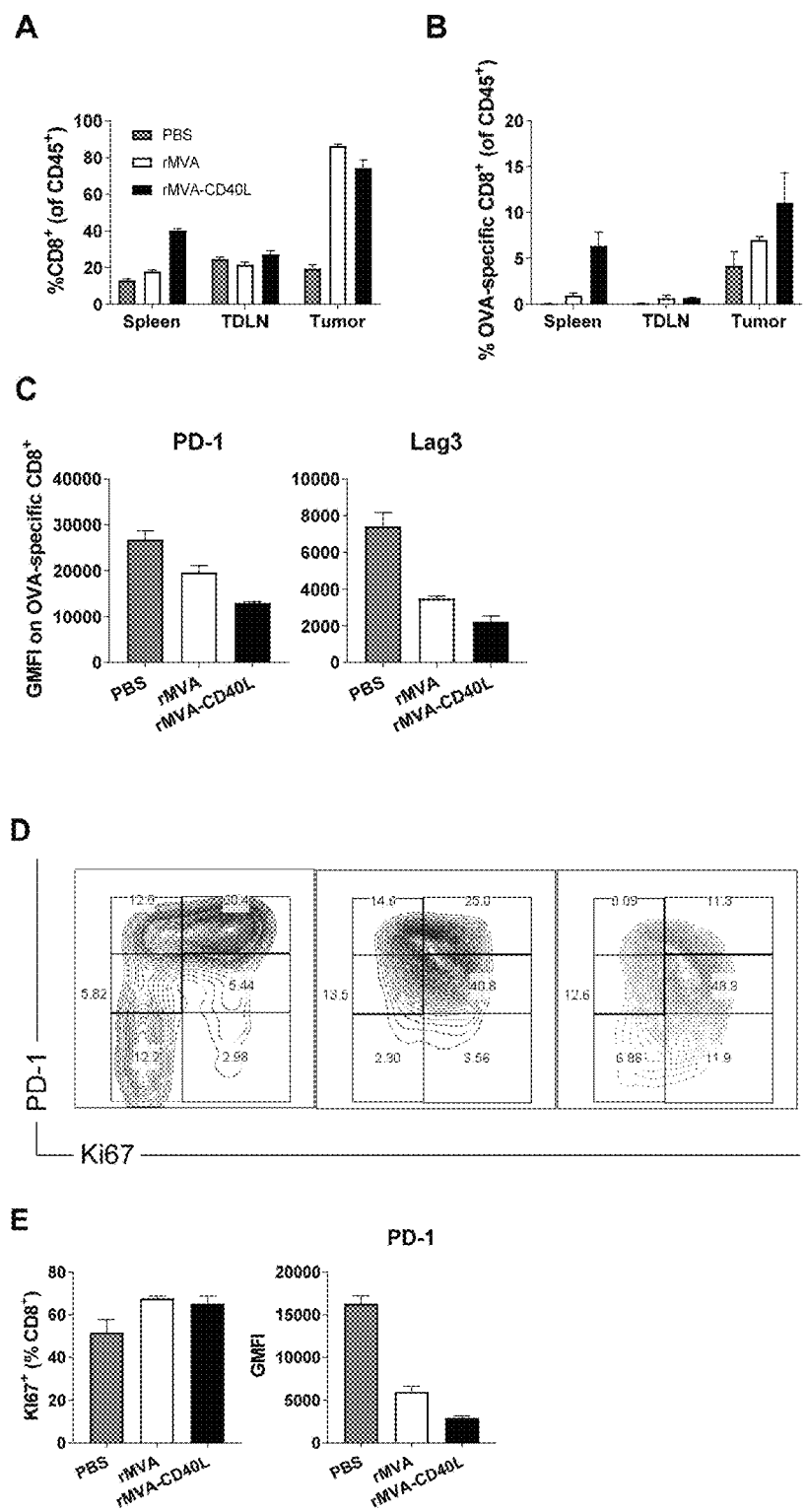
FIGS. 21A-21G show increased T cell infiltration in the tumor microenvironment (TME) after rMVA-CD40L immunization. C57BL/6 mice bearing palpable B16.OVA tumors were immunized IV either with PBS, MVA-OVA (rMVA) or MVA-OVA-CD40L (rMVA-CD40L) as described in Example 16. Seven days later, mice were sacrificed.
Figure 21:
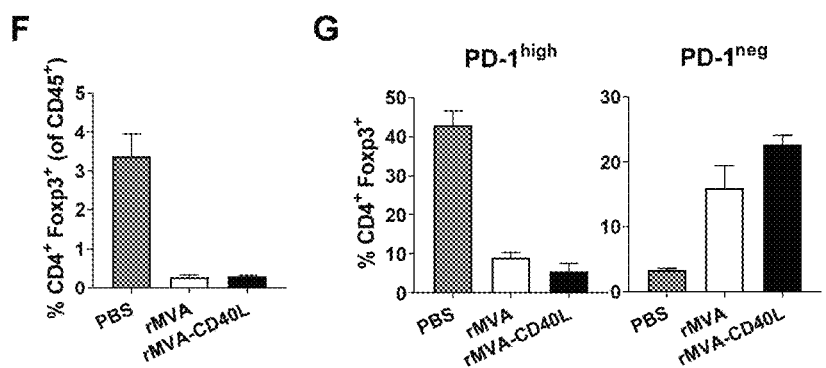
Figure 22:
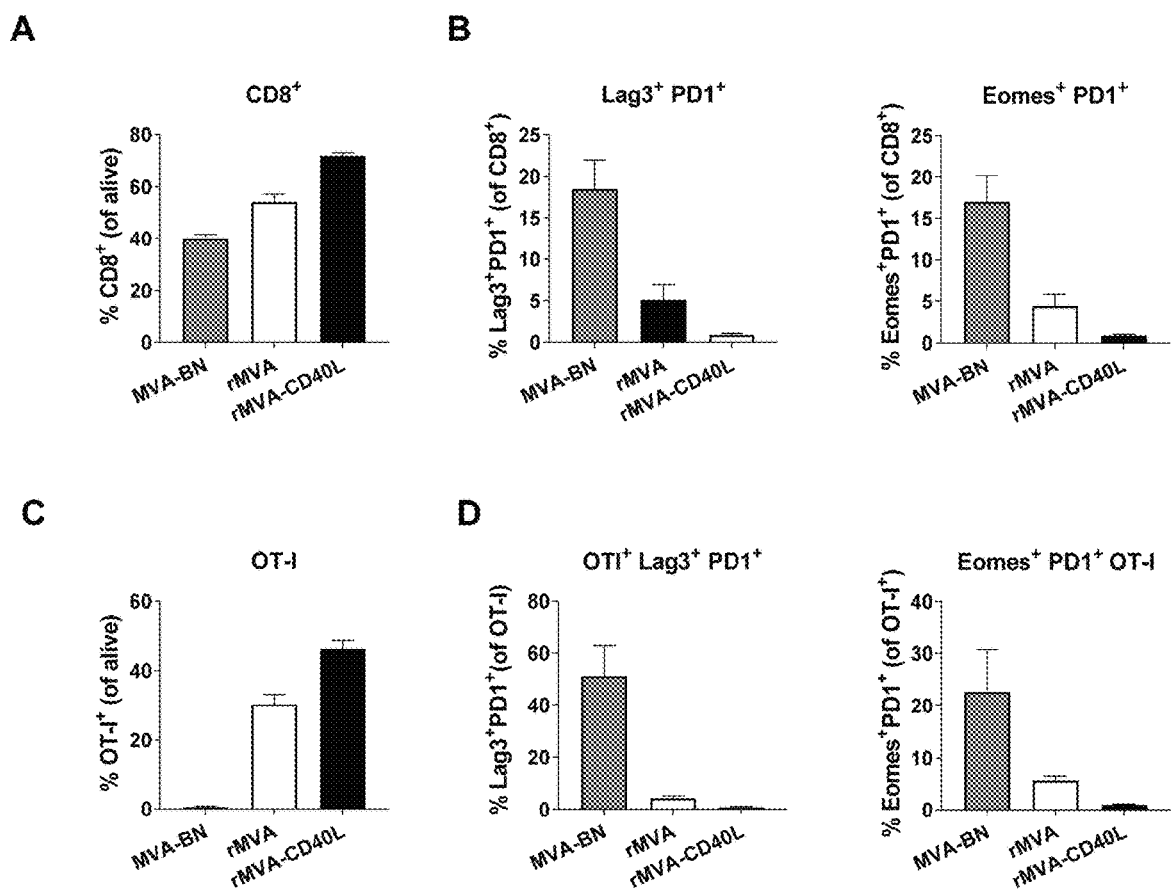
FIGS. 22A-22D show persistence of TAA-specific CD8 T cells with a less exhausted phenotype in the TME after rMVA-CD40L immunization. Purified OVA-specific TCR-transgenic CD8 T cells (OT-I) were IV transferred into B16.OVA tumor bearers when tumors were palpable as described in Example 17. When tumors reached at least 60 mm$^3$ in volume animals were immunized IV with MVA-BN®, MVA-OVA (rMVA) or MVA-OVA-CD40L (rMVA-CD40L). 17 days later, mice were sacrificed and analyzed for: A) Frequency of CD8$^+$ T cells among leukocytes in tumor tissues; B) Frequency of Lag3$^+$PD1$^+$ within CD8+ T cells (left graph); Frequency of Eomes$^+$PD1$^+$ T cells within CD8+ T cells (right graph); C) Presence of OT-I-transgenic CD8$^+$ T cells within the TME upon immunization; D) Frequency of Lag3$^+$PD1$^+$ exhausted T cells within OT-I$^+$ CD8$^+$ T cells (left graph); and Frequency of Eomes$^+$PDF$^+$ exhausted T cells within OT-I+CD8$^+$ T cells (right graph).
Figure 23:
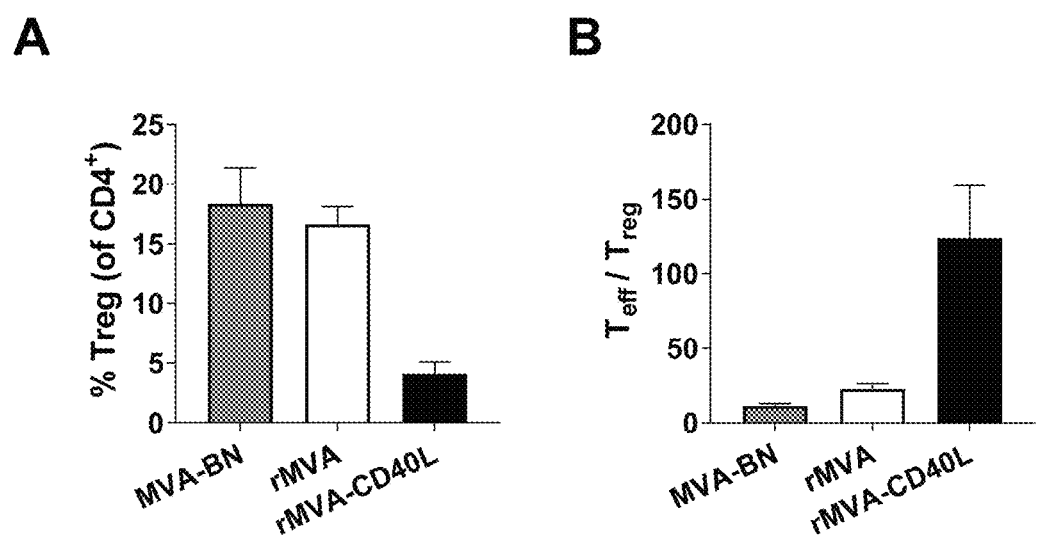
FIGS. 23A-23B show a long-term reduction of regulatory T cells (Treg) in the TME after rMVA-CD40L immunization. Purified OVA-specific TCR-transgenic CD8 T cells (OT-I) were IV transferred into B16.OVA tumor bearers when tumors were palpable as described in Example 18. When tumors reached at least 60 mm$^3$ in volume animals were immunized IV with MVA-BN®, MVA-OVA (rMVA) or MVA-OVA-CD40L (rMVA-CD40L). 17 days later, mice were sacrificed for further analysis.

IV administration of MVA reduces a tumor's immunosuppressive effects. Illustrated in FIGS. 29A-29D and 32, intravenously administered recombinant MVA encoding a heterologous antigen and optionally a CD40L, induced infiltration of CD8$^+$ T cells in the tumor and reduced multiple immunosuppressive effects typically employed by tumors to evade the immune system. In addition to increased endogenous CD8$^+$ cells within the tumors upon recombinant MVA with or without CD40L challenge, antigen (OVA)-specific T cells were increased in spleen and tumors upon IV administration of a recombinant MVA with CD40L compared to MVA without CD40L. Moreover, tumor infiltrating T lymphocytes expressed less immunosuppressive surface molecules PD-1 and Lag3 when checked in endogenous T cells (FIGS. 22C-E, 23B) or transferred antigen (OVA)-specific T cells (FIG. 21D) and were proliferating in the tumor microenvironment. Reduced PD-1 expression on tumor-infiltrating T cells after rMVA and rMVA-CD40L immunization was unexpected because type I and II interferons, which are induced by both vectors (FIGS. 14C and 14E), are known inducer of PD-1 and PD-L1 expression (reviewed by Dong et al. (2017) *Oncotarget* 8: 2171-86). Unexpectedly, immunosuppressive T regulatory cell (Treg) numbers in the tumor microenvironment were decreased (FIG. 22F, 23A) when recombinant MVA encoding a heterologous antigen and optionally a CD40L, resulting in an enhanced effector T cell to Treg ratio in the tumor microenvironment (FIG. 23B). Reduced expression of immune-dampening molecules such as PD-1 and Lag3 as well as reduced numbers of Tregs in the tumor tissue correlate with the enhanced anti-tumor effects seen after rMVA and rMVA-CD40L immunization.

The pharmaceutical combination of the present invention reduces tumor burden and increases survival rate in cancer patients. In various embodiments, the pharmaceutical combination includes a) an IV administration of a recombinant MVA encoding a heterologous TAA and optionally CD40L and b) an administration of an antibody. Shown in FIGS. 26A-26B and 33A-33B, the pharmaceutical combination resulted in a reduction in tumor volume and an increase in overall survival rate.

In at least one aspect, the enhanced anti-tumor effects of the pharmaceutical combination (e.g., reduced tumor volume and/or increased survival rate) is achieved from the synergistic combining of the individual enhancements of the innate and adaptive T cell responses described herein. In one exemplary embodiment, these individual enhancements include one or more of those listed above, e.g., an enhanced innate (e.g., NK cell) response, enhanced ADCC mediated killing of tumor cells, enhanced NK cell killing of tumor cells having lower MHC class I levels, and an enhanced adaptive T cell response. Furthermore, the one or more dosing regimens of the present invention further improve and enable a patient's immune system to kill tumor cells over a period of time.

IV Administration of MVA-HER2-Brachyury plus anti-HER2 antibody. In one advantageous embodiment of the invention, the pharmaceutical combination comprises a) an intravenous administration of a recombinant MVA encoding HER2 and Brachyury antigens and optionally a CD40L and b) an administration of an anti-HER2 antibody. This embodiment induces the enhanced immune response described herein and additionally focuses tumor cell killing on HER2 and Brachyury expressing tumor cells. In additional advantageous aspects, the HER2 antigen comprises one more modifications that further increase the efficacy of the combination therapy of the present invention. Shown in FIG. 29A-29D, the rMVA-HER2-Brachyury and the rMVA-HER2-Brachyury-CD40L showed activation of Dendritic Cells (DCs). DC activation was enhanced by rMVA-HER2-Brachyury-CD40L as compared to rMVA-HER2-Brachyury. Shown in FIG. 33A-33B, administration of the pharmaceutical combination described in the present invention resulted in a significant increase in tumor reduction and overall survival rate of the subjects.

In one specific embodiment, the present invention is directed and tailored to treat cancer patients with HER2 expressing malignancies such as HER2 positive breast or gastric cancers which are treated with HER2 binding antibodies. The recombinant MVA encoding HER2 induces highly effective killer T cells against the HER2 expressing tumor cells while the Brachyury transgene encoded by the recombinant MVA induces highly effective killer T cells against Brachyury tumor cells that have the potential to be metastatic.

Definitions

As used herein, the singular forms "a," "an," and "the," include plural references unless the context clearly indicates otherwise. Thus, for example, reference to "a nucleic acid" includes one or more of the nucleic acid and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having." Any of the aforementioned terms (comprising, containing, including, having), though less preferred, whenever used herein in the context of an aspect or embodiment of the present invention can be substituted with the term "consisting of. When used herein "consisting of" excludes any element, step, or ingredient not specified in the claim element. When used herein, "consisting essentially of" does not exclude materials or steps that do not materially affect the basic and novel characteristics of the claim.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

"Mutation" described herein is as defined herein any a modification to a nucleic acid or amino acid, such as deletions, additions, insertions, and/or substitutions.

A "host cell" as used herein is a cell that has been introduced with a foreign molecule, virus, or microorganism. In one non-limiting example, as described herein, a cell of a suitable cell culture as, e.g., CEF cells, can be infected with a poxvirus or, in other alternative embodiments, with a plasmid vector comprising a foreign or heterologous gene. Thus, a suitable host cell and cell cultures serve as a host to poxvirus and/or foreign or heterologous gene.

"Percent (%) sequence homology or identity" with respect to nucleic acid sequences described herein is defined as the percentage of nucleotides in a candidate sequence that are identical with the nucleotides in the reference sequence (i.e., the nucleic acid sequence from which it is derived), after aligning the sequences and introducing gaps, if necessary, to achieve the maximum percent sequence identity, and not considering any conservative substitutions as part of the sequence identity. Alignment for purposes of determining percent nucleotide sequence identity or homology can be achieved in various ways that are within the skill in the art, for example, using publicly available computer software such as BLAST, ALIGN, or Megalign (DNASTAR) software. Those skilled in the art can determine appropriate parameters for measuring alignment, including any algorithms needed to achieve maximum alignment over the full length of the sequences being compared.

For example, an appropriate alignment for nucleic acid sequences is provided by the local homology algorithm of Smith and Waterman ((1981) *Advances in Applied Mathematics* 2: 482-489). This algorithm can be applied to amino acid sequences by using the scoring matrix developed by Dayhoff (*Atlas of Protein Sequences and Structure*, M. O. Dayhoff ed., 5 suppl. 3: 353-358, National Biomedical Research Foundation, Washington, D.C., USA), and normalized by Gribskov ((1986) *Nucl. Acids Res.* 14(6): 6745-6763). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present invention is to use the MPSRCH package of programs copyrighted by the University of Edinburgh, developed by Collins and Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated, the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: blast.ncbi.nlm.nih.gov/.

The term "prime-boost vaccination" or "prime-boost regimen" refers to a vaccination strategy or regimen using a first priming injection of a vaccine targeting a specific antigen followed at intervals by one or more boosting injections of the same vaccine. Prime-boost vaccination may be homologous or heterologous. A homologous prime-boost vaccination uses a vaccine comprising the same antigen and vector for both the priming injection and the one or more boosting injections. A heterologous prime-boost vaccination uses a vaccine comprising the same antigen for both the priming injection and the one or more boosting injections but different vectors for the priming injection and the one or more boosting injections. For example, a homologous prime-boost vaccination may use a recombinant poxvirus comprising nucleic acids expressing one or more antigens for the priming injection and the same recombinant poxvirus expressing one or more antigens for the one or more boosting injections. In contrast, a heterologous prime-boost vaccination may use a recombinant poxvirus comprising nucleic acids expressing one or more antigens for the priming injection and a different recombinant poxvirus expressing one or more antigens for the one or more boosting injections.

The term "recombinant" means a polynucleotide, virus or vector of semisynthetic, or synthetic origin which either does not occur in nature or is linked to another polynucleotide in an arrangement not found in nature.

As used herein, reducing or a reduction in tumor volume can be characterized as a reduction in tumor volume and/or size but can also be characterized in terms of clinical trial endpoints understood in the art. Some exemplary clinical trial endpoints associated with a reduction in tumor volume and/or size can include, but are not limited to, Response Rate (RR), Objective response rate (ORR), and so forth.

As used herein an increase in survival rate can be characterized as an increase in survival of a cancer patient, but can also be characterized in terms of clinical trial endpoints understood in the art. Some exemplary clinical trial endpoints associated with an increase in survival rate include, but are not limited to, overall survival rate (ORR), Progression free survival (PFS) and so forth.

As used herein, a "transgene" or "heterologous" gene is understood to be a nucleic acid or amino acid sequence which is not present in the wild-type poxviral genome (e.g., Vaccinia, Fowlpox, or MVA). The skilled person understands that a "transgene" or "heterologous gene", when present in a poxvirus, such as Vaccinia Virus, is to be incorporated into the poxviral genome in such a way that, following administration of the recombinant poxvirus to a host cell, it is expressed as the corresponding heterologous gene product, i.e., as the "heterologous antigen" and\or "heterologous protein." Expression is normally achieved by operatively linking the heterologous gene to regulatory elements that allow expression in the poxvirus-infected cell. Preferably, the regulatory elements include a natural or synthetic poxviral promoter.

A "vector" refers to a recombinant DNA or RNA plasmid or virus that can comprise a heterologous polynucleotide. The heterologous polynucleotide may comprise a sequence of interest for purposes of prevention or therapy, and may optionally be in the form of an expression cassette. As used herein, a vector needs not be capable of replication in the ultimate target cell or subject. The term includes cloning vectors and viral vectors.

Pharmaceutical Combinations and Methods

In various embodiments, the present invention includes a pharmaceutical combination for treating a cancer patient by reducing tumor volume and/or increasing survival in the cancer patient. The pharmaceutical combination comprises a recombinant MVA comprising a first nucleic acid encoding a first heterologous tumor-associated antigen (TAA) that when administered intravenously induces both an enhanced Natural Killer (NK) cell response and an enhanced T cell response as compared to a NK cell response and a T cell response induced by a non-intravenous administration of a recombinant MVA virus comprising a nucleic acid encoding a heterologous tumor-associated antigen.

Enhanced NK Cell Response

In one aspect, an enhanced NK cell response according to the present disclosure is characterized by one or more of the following: 1) an increase in NK cell frequency, 2) an increase in NK cell activation, and/or 3) an increase in NK cell proliferation. Thus, whether an NK cell response is enhanced in accordance with the present disclosure can be determined by measuring the expression of one or more cytokines which are indicative of an increased NK cell frequency, increased NK cell activation, and/or increased NK cell proliferation. Exemplary markers that are useful in measuring NK cell frequency and/or activity include one or more of: NKp46, IFN-γ, CD69, CD70, NKG2D, FasL, granzyme B, CD56, and/or Bcl-$X_L$. Exemplary markers that are useful in measuring NK cell activation include one or more of IFN-γ, CD69, CD70, NKG2D, FasL, granzyme B and/or Bcl-$X_L$. Exemplary markers that are useful in measuring NK cell proliferation include: Ki67. These molecules and the measurement thereof are validated assays that are understood in the art and can be carried out according to known techniques (see, e.g., Borrego et al. (1999) *Immunology* 97: 159-65; Fogel et al. (2013) *J Immunol.* 190: 6269-76). Additionally, assays for measuring the molecules can be found in Examples 1-3, and 9 of the present disclosure. At least in one aspect, 1) an increase in NK cell frequency can be defined as at least a 2-fold increase in $CD3^-NKp46^+$ cells compared to pre-treatment/baseline; 2) an increase in NK cell activation can be defined as at least a 2-fold increase in IFN-γ, CD69, CD70, NKG2D, FasL, granzyme B and/or Bcl-$X_L$ expression compared to pre-treatment/baseline expression; and/or 3) an increase in NK cell proliferation is defined as at least a 1.5 fold increase in Ki67 expression compared to pre-treatment/baseline expression.

In a more preferred aspect, an "enhanced NK cell response" as used in the present disclosure is characterized by an increase in NK cell mediated tumor cell killing. NK cell mediated tumor cell killing can be analyzed by measuring release of Lactate Dehydrogenase (LDH) into the cell culture medium, as shown in Example 5. Thus, within the context of the present invention, whether or not a pharmaceutical combination "enhances an NK cell response" can be characterized by the existence of an increase in NK cell mediated tumor cell killing. NK cell mediated tumor cell killing can be analyzed by measuring the release of Lactate Dehydrogenase as seen in Example 5. Assays associated with LDH and the measurement thereof are validated and understood in the art. At least one aspect, the increase in NK cell mediated tumor cell killing can be defined as at least a 2-fold increase in tumor cell killing.

Enhanced ADCC Response

In at least one aspect, the enhanced NK cell response induced by the present invention results in an enhanced ADCC response. An "enhanced ADCC response" according to the present invention is characterized by an increase in innate immune effector cells' ability to target and kill tumor cells coated by antibodies. In the context of the present disclosure an innate immune effector can include, but is not limited to, NK cells, macrophages, neutrophils, basophils, eosinophils, mast cells, dendritic cells and so forth. In a more preferred aspect, an innate immune effector is an NK cell. Assays that are useful for measuring an effector cell's ability to kill tumor cells include ex vivo Effector:Target killing assays, where "effector" are isolated effector cells and "target" are tumor cells in the presence of antibodies (see Yamashita et al. (2016) *Sci. Rep.* 6: 19772 and Broussas et al. (2013) *Methods Mol. Biol.* 988: 305-17). The ex vivo Effector:Target killing assays are validated and understood in the art. Additionally, assays for measuring an effector cell's ability to kill tumor cells can be found in Example 5. Thus, in one aspect, within the context of the present application, whether or not an enhanced innate immune response, including an enhanced NK cell response, enhances ADCC can be characterized by measuring levels of tumor cell killing through one or more of: 1) using different ratios of effector cells per coated target cell (tumor cell coated with antibody); and 2) using a constant ratio of effector cells and one or more concentrations of antibodies e.g., lower concentrations of antibody bound to tumor antigen are compared to levels of tumor cell killing at higher concentrations.

In a preferred aspect "enhances ADCC response" according to the present disclosure is characterized by an increase in NK cells' ability to target and kill tumor cells coated by antibodies. Assays that are useful for measuring an NK cell's ability to kill tumor cells include ex vivo Effector:Target killing assays, where "effector" are isolated NK cells and "target" are tumor cells in the presence of antibodies. Additionally, assays for measuring a NK cell's ability to kill tumor cells can be found in Example 5. Thus, in one aspect, within the context of the present application, whether or not an NK cell response enhances ADCC can be characterized by measuring levels of tumor cell killing: 1) using different ratios of NK cells per coated target cell (tumor cell coated with antibody); and/or 2) using a constant ratio of NK cells and one or more concentrations of antibodies, e.g., lower concentrations of antibody bound to tumor antigen are compared to levels of tumor cell killing at higher concentrations.

Stronger NK Cell Mediated Toxicity

In additional aspects, the enhanced NK cell response results in an increased ability of the innate immune effectors, such as NK cells, to attack and kill tumor cells having low MHC expression levels. In one aspect killing tumor cells having low MHC levels can be characterized by innate immune effectors, e.g., NK cells, having a stronger NK cell mediated toxicity, meaning NK cells are more efficiently killing tumor cells. NK cells having a stronger NK cell mediated toxicity can be measured by an increased number of tumor cells killed per NK cells. This can be determined through the use of an effector: target killing assay. Such assays are validated and known in the art and demonstrated by the present application in at least Example 4 and FIG. 9.

Enhanced Innate Immune Effector Cells

In additional aspects, an IV administration of the recombinant poxviruses of the present application not only enhances the NK cell response, but also enhances all aspects of the innate immune response. Enhancement of the innate immune response can be characterized as an increase in innate effector cell: 1) frequency, 2) activation, and/or 3) proliferation. The innate effector cells can include NK cells, innate lymphoid cells (ILCs), macrophages, neutrophils, basophils, eosinophils, mast cells, monocytes, and/or dendritic cells. In various aspects, whether an innate immune response is enhanced in accordance with the present application can be determined by measuring one or more of the expression of cytokines and/or activation markers associated with the described effector cells of the innate response. These cytokines and activation markers and the measurement thereof are validated and understood in the art and can be carried out according to known techniques (see Borrego et al. (1999) *Immunology* 97: 159-65; Fogel et al. (2013) *J Immunol.* 190: 6269-76).

Enhanced T Cell Response

In accordance with the present application, an "enhanced T cell response" is characterized by one or more of the following: 1) an increase in frequency of CD8 T cells; 2) an increase in CD8 T cell activation; and/or 3) an increase in CD8 T cell proliferation. Thus, whether a T cell response is enhanced in accordance with the present application can be determined by measuring the expression of one or more cytokines which are indicative of 1) an increase in CD8 T cell frequency 2) an increase in CD8 T cell activation; and/or 3) an increase CD8 T cell proliferation. Exemplary markers that are useful in measuring CD8 T cell frequency, activation, and proliferation include CD3, CD8, IFN-γ, TNF-α, IL-2, CD69 and/or CD44, and Ki67, respectively. Measuring antigen specific T cell frequency can also be measured by ELIspot or MHC Multimers such as pentamers or dextramers as shown in FIGS. 11, 12, 15A-15D, 19A-19C, and 21A-21E. Such measurements and assays are validated and understood in the art.

In one aspect, an increase in CD8 T cell frequency is characterized by an at least a 2-fold increase in IFN-γ and/or dextramee CD8 T cells compared to pre-treatment/baseline. An increase in CD8 T cell activation is characterized as at least a 2-fold increase in CD69 and/or CD44 expression compared to pre-treatment/baseline expression. An increase in CD8 T cell proliferation is characterized as at least a 2-fold increase in Ki67 expression compared to pre-treatment/baseline expression.

In an alternative aspect, an enhanced T cell response is characterized by an increase in CD8 T cell expression of effector cytokines and/or an increase of cytotoxic effector functions. An increase in expression of effector cytokines can be measured by expression of one or more of IFN-γ, TNF-α, and/or IL-2 compared to pre-treatment/baseline. An increase in cytotoxic effector functions can be measured by expression of one or more of CD107a, granzyme B, and/or perforin and/or antigen-specific killing of target cells.

The assays, cytokines, markers, and molecules described herein and the measurement thereof are validated and understood in the art and can be carried out according to known techniques. Additionally, assays for measuring the T cells responses can be found in Examples 6 and 7, wherein T cell responses were analyzed.

The enhanced T cell response realized by the present invention is particularly advantageous in combination with the enhanced NK cell response, as the enhanced T cells effectively target and kill those tumor cells that have evaded and/or survived past the initial innate immune responses in the cancer patient. Furthermore, antibody treatment can enhance MHC class I presentation of TAAs, resulting in higher susceptibility of TAA-expressing tumors to lysis by TAA-specific T cells (Kono et al. (2004) Clin. Cancer Res. 10: 2538-44).

In additional embodiments, the pharmaceutical combination further comprises an antibody, wherein the antibody is specific to an antigen that is expressed or overexpressed on the cell membrane, preferably an outer cell membrane of a tumor cell. It is contemplated that the antibody can be any antibody as described by the present disclosure. In preferred embodiments, the antibody comprises an Fc domain.

In additional embodiments, there is a method for reducing tumor volume and/or increasing survival in a cancer patient. The method comprises a) intravenously administering to the cancer patient a recombinant MVA comprising a first nucleic acid encoding a first heterologous tumor-associated antigen (TAA) that when administered intravenously induces both an enhanced innate immune response and an enhanced T cell response as compared to an innate immune response and a T cell response induced by a non-intravenous administration of a recombinant MVA virus comprising a nucleic acid encoding a heterologous tumor-associated antigen; and b) administering to the cancer patient an antibody, wherein the antibody comprises an Fc domain and is specific to an antigen that is expressed on the cell membrane of a tumor cell, wherein administration of a) and b) to the cancer patient reduces tumor size in the cancer patient and/or increases survival of the cancer patient as compared to a non-intravenous administration of a) or an administration of b) alone. In a more preferred embodiment, the enhanced innate immune response comprises an enhanced NK cell response as described herein.

In another embodiment, there is a method for enhancing antibody therapy in a patient, the method comprising a) administering to the cancer patient an antibody, wherein the antibody comprises an Fc domain and is specific to an antigen that is expressed on the cell membrane of a tumor cell, and wherein administering the antibody induces ADCC in the patient; and b) intravenously administering to the cancer patient a recombinant MVA comprising a first nucleic acid encoding a first heterologous tumor-associated antigen (TAA) that induces both an enhanced innate immune response and an enhanced T cell response in the patient, wherein the enhanced innate immune response enhances the ADCC in the patient, as compared to a non-intravenously administered combination of a) and b) or a) and b) alone. In a more preferred embodiment, the enhanced innate immune response comprises an enhanced NK cell response as described herein.

In still another embodiment there is a method for increasing the effectiveness of antibody therapy in a cancer patient, the method comprising administering the pharmaceutical combination of the present invention, wherein administering the combination to the patient decreases the antibody concentration needed for NK cell-mediated toxicity in tumor cells. In at least one advantageous aspect, decreasing antibody concentration needed for NK cell mediated toxicity enables the enhanced NK cell response to kill tumor cells that have decreased extracellular antigen expression in order to evade destruction by bound antibody targets. Additionally, decreasing needed antibody concentration can enable treatment with decreasing amounts of antibody.

In the context of the present application, decreasing the antibody concentration needed for NK cell mediated toxicity can be characterized as a decrease in antibody concentration needed for tumor cell killing. A decrease in antibody concentration needed for tumor cell killing can be measured by an ex vivo Effector: target killing assays, where "effector" are isolated NK cells and "target" are tumor cells in the presence of antibodies. Additionally, assays for measuring include measuring levels of tumor cell killing by for example, 1) using different ratios of NK cells per coated target cell (tumor cell coated with antibody); and/or 2) using a constant ratio of NK cells and one or more concentrations of antibodies e.g., lower concentrations of antibody bound to tumor antigen are compared to levels of tumor cell killing at higher concentrations. Such assays are known in the art and also presently described in Example 5 and 31 of the present application.

In yet additional embodiments, the pharmaceutical combination and methods described herein are for treating a human cancer patient. In preferred embodiments, the cancer patient is suffering from and/or is diagnosed with a cancer selected from the group consisting of: breast cancer, lung cancer, head and neck cancer, thyroid, melanoma, gastric cancer, bladder cancer, kidney cancer, liver cancer, melanoma, pancreatic cancer, prostate cancer, ovarian cancer, urothelial, cervical, or colorectal cancer.

In still additional preferred embodiments, the pharmaceutical combinations and methods of the present invention each comprise CD40L. Preferably the CD40L is encoded by the recombinant MVA.

Exemplary Tumor-Associated Antigens

In certain preferred embodiments, the first and/or second Tumor Associated antigen (TAA) includes but is not limited to HER2, PSA, PAP, CEA, MUC-1, survivin, TYRP1, TYRP2, or Brachyury alone or in combinations. Such exemplary combination may include HER2 and Brachyury, CEA and MUC-1, or PAP and PSA.

Numerous TAAs are known in the art. Exemplary TAAs include, but are not limited to, 5 alpha reductase, alpha-fetoprotein, AM-1, APC, April, BAGE, beta-catenin, Bc112, bcr-abl, Brachyury, CA-125, CASP-8/FLICE, Cathepsins, CD19, CD20, CD21, CD23, CD22, CD33 CD35, CD44, CD45, CD46, CDS, CD52, CD55, CD59, CDC27, CDK4, CEA, c-myc, Cox-2, DCC, DcR3, E6/E7, CGFR, EMBP, Dna78, farnesyl transferase, FGF8b, FGF8a, FLK-1/KDR, folic acid receptor, G250, GAGE-family, gastrin 17, gastrin-releasing hormone, GD2/GD3/GM2, GnRH, GnTV, GP1, gp100/Pme117, gp-100-in4, gp15, gp75/TRP-1, hCG, heparanase, HER2/neu, HMTV, Hsp70, hTERT, IGFR1, IL-13R, iNOS, Ki67, KIAA0205, K-ras, H-ras, N-ras, KSA, LKLR-FUT, MAGE-family, mammaglobin, MAP17, melan-A/MART-1, mesothelin, MIC AB, MT-MMPs, mucin, NY-ESO-1, osteonectin, p15, P170/MDR1, p53, p97/melanotransferrin, PAI-1, PDGF, uPA, PRAME, probasin, progenipoietin, PSA, PSM, RAGE-1, Rb, RCAS1, SART-1, SSX-family, STAT3, STn, TAG-72, TGF-alpha, TGF-beta, Thymosin-beta-15, TNF-alpha, TYRP-, TYRP-2, tyrosinase, VEGF, ZAG, p16INK4, and glutathione-S-transferase.

A preferred PSA antigen comprises the amino acid change of isoleucine to leucine at position 155, as found in U.S. Pat. No. 7,247,615, which is incorporated herein by reference.

In more preferred embodiments of present invention, the first and/or second heterologous TAA are selected from HER2 and Brachyury. In even more preferred embodiments, the first and/or second heterologous TAA are selected from the synthetic HER2 and Brachyury proteins as described herein.

In additional preferred embodiments, the first and/or second heterologous TAA comprise one or more mutations. In at least one embodiment, the one or more mutations comprise mutations that prevent the antibodies of the present disclosure from binding to the first and/or second heterologous TAA. In additional embodiments, the one or more mutations comprise mutations that prevent the first and/or second TAA from performing the one or more normal cellular functions of the TAA. Exemplary embodiments of the one or more mutations are described by the synthetic HER2 and synthetic Brachyury proteins of the present invention.

Synthetic HER2 Proteins

With the development of the present invention, the inventors determined that one or more modifications of the HER2 antigens and/or nucleic acids encoding the HER2 antigens as described herein increase the efficacy of the combination therapy.

Accordingly, in various embodiments the present invention includes a nucleic acid encoding a HER2 antigen selected from HER2v1 and HER2v2. HER2v1 and HER2v2 comprise SEQ ID NO: 1 and SEQ ID NO: 13, respectively.

In at least one specific aspect, the nucleic acid encoded by SEQ ID NO:1 and/or 13 is particularly advantageous as SEQ ID NO: 1 and/or 13 is configured to function synergistically with antibodies to the HER2 antigen when administered as part of the combination therapy.

In one exemplary embodiment of the present invention, the HER2 antibodies comprise those antibodies that are approved for treatment of a HER2 expressing cancer, or in more specific embodiment, a HER2 expressing breast cancer. Two humanized monoclonal antibodies targeting HER2 have been developed and approved for treatment of HER2-expressing breast cancer. Both antibodies bind at different sites in the extracellular domain of HER2. Trastuzumab (branded as Herceptin® and having Herzuma and ABP 980 as biosimilars) binding results in signal transduction blockade and prevention of HER2 cleavage. In contrast, Pertuzumab (Perjeta®) sterically blocks HER2 dimerization with other EGF receptors and blocks ligand-activated signaling. Both Trastuzumab and Pertuzumab provide a dual blockade of HER2-driven signaling pathways and in addition have the ability to mediate ADCC against breast cancer. Thus, in various specific embodiments of the present invention, the antibodies of the present invention comprise Trastuzumab, Herzuma, ABP 980, and/or Pertuzumab.

Synthetic HER2 v1

In one or more embodiments, the synthetic HER2 protein is HER2v1 (SEQ ID NO: 1). As previously described herein, to enhance the efficacy of the combination therapy, mutations to the transgenes encoded by the recombinant MVA are made to minimize any potential interaction and/or binding between the transgene and the administered antibodies. Accordingly, to enhance the efficacy of a therapy involving co-administration of a HER2 antibody such as, Trastuzumab and Pertuzumab, one or more mutations of the HER2 antigen were made. More specifically, the relevant antibody binding sites in HER2 were mutated. Thus, in one or more embodiments, the synthetic HER2 protein comprises one or more mutations in the following amino acid domains: 579-625 (Trastuzumab Binding domain), 267-337 (Pertuzumab binding domain), 274-288 (HER2 dimerization domain), 721-987 (kinase domain), and 1139-1248 (phosphorylation domain). In one or more exemplary embodiments of the present invention, the HER2 antigen includes one or more of the following mutations: E580A, F595A, K615A, L317A, H318A, D277R, E280K, K753M, Y1023A. Mutations to the HER2v1 antigen (based on HER2 (NP_004439.2) are illustrated below.

```
  1 MELAALCRWG LLLALLPPGA ASTQVCTGTD MKLRLPASPE THLDMLRHLY QGCQVVQGNL

61 ELTYLPTNAS LSFLQDIQEV QGYVLIAHNQ VRQVPLQRLR IVRGTQLFED NYALAVLDNG

121 DPLNNTTPVT GASPGGLREL QLRSLTEILK GGVLIQRNPQ LCYQDTILWK DIFHKNNQLA

181 LTLIDTNRSR ACHPCSPMCK GSRCWGESSE DCQSLTRTVC AGGCARCKGP LPTDCCHEQC

241 AAGCTGPKHS DCLACLHFNH SGICELHCPA LVTYNTRTFK SMPNPEGRYT FGASCVTACP

301 YNYLSTDVGS CTLVCPAANQ EVTAEDGTQR CEKCSKTCAR VCYGLGMEHL REVRAVTSAN
```

-continued

```
 361 IQEFAGCKKI FGSLAFLPES FDGDPASNTA PLQPEQLQVF ETLEEITGYL YISAWPDSLP

421 DLSVFQNLQV IRGRILHNGA YSLTLQGLGI SWLGLRSLRE LGSGLALIHH NTHLCFVHTV

481 PWDQLFRNPH QALLHTANRP EDECVGEGLA CHQLCARGHC WGPGPTQCVN CSQFLRGQEC

541 VEECRVLQGL PREYVNARHC LPCHPECQPQ NGSVTCFGPA ADQCVACAHY KDPPACVARC

601 PSGVKPDLSY MPIWAFPDEE GACQPCPINC THSCVDLDDK GCPAEQRASP LTSIISAVVG

661 ILLVVVLGVV FGILYKRRQQ KIRKYTMRRL LQETELVEPL TPSGAMPNQA QMRILKETEL

721 RKVKVLGSGA FGTVYKGIWI PDGENVKIPV AIMVLRENTS PKANKEILDE AYVMAGVGSP

781 YVSRLLGICL TSTVQLVTQL MPYGCLLDHV RENRGRLGSQ DLLNWCMQIA KGMSYLEDVR

841 LVHRDLAARN VLVKSPNHVK ITDFGLARLL DIDETEYHAD GGKVPIKWMA LESILRRRFT

901 HQSDVWSYGV TVWELMTFGA KPYDGIPARE IPDLLEKGER LPQPPICTID VYMIMVKCWM

961 IDSECRPRFR ELVSEFSRMA RDPQRFVVIQ NEDLGPASPL DSTFYRSLLE DDDMGDLVDA

1021 EEALVPQQGF FCPDPAPGAG GMVHHRHRSS STRSGGGDLT LGLEPSEEEA PRSPLAPSEG

1081 AGSDVFDGDL GMGAAKGLQS LPTHDPSPLQ RYSEDPTVPL PSETDGYVAP LTCSPQPE

1141 ~~NQPDVRPQPP~~ ~~SPREGPLPAA~~ ~~RPAGATLERP~~ ~~KTLSPGKNGV~~ ~~VKDVFAFGGA~~ ~~VENPEYLTPQ~~

1201 ~~GGAAPQPHPP~~ ~~PAFSPAFDNL~~ ~~YYWDQDPPER~~ ~~GAPPSTFKGT~~ ~~PTAENPEY~~LG LDVPV
```

Amino Acid Sequence of HER2 vi. Synthetic HER shown above is based from HER2 NP_004439.2. Mutated amino acids are shown by underlines and strikethrough. Amino Acids 579-625 is the binding site for Herceptin. Amino Acids 267-337 is the binding site for Perjeta. Amino Acids 274-288 are the residues for the dimerization domain. Amino Acids 721-987 are the residues for the kinase domian. Amino Acids 1139-1248 are the residues in the phosphorylation domain. (SEQ ID NO: 1)

Synthetic HER2 v2

In one or more embodiments, the synthetic HER2 protein is HER2v2 (SEQ ID NO: 13). As previously described herein, to enhance the efficacy of the combination therapy, mutations to the transgenes encoded by the recombinant MVA are made to minimize any potential interaction and/or binding between the transgene and the administered antibodies. Accordingly, to enhance the efficacy of a therapy involving co-administration of a HER2 antibody such as, Trastuzumab and Pertuzumab, one or more mutations of the HER2 antigen were made. More specifically, the relevant antibody binding sites in HER2 were mutated. Thus, in one or more embodiments, the synthetic HER2 protein comprises one or more mutations in the following amino acid domains: 579-625 (Trastuzumab Binding domain), 267-337 (Pertuzumab binding domain), 274-288 (HER2 dimerization domain), 721-987 (kinase domain), and 1139-1248 (phosphorylation domain). In one or more exemplary embodiments of the present invention, the HER2 antigen includes one or more of the following mutations: E580A, F595A, K615A, L317A, H318A, D277R, E280K, K753M, Y1023A.

At least in one aspect, the above mutations enhance the combination therapy as they function to minimize any interaction and/or unwanted binding of MVA-HER2 antigen with the HER2 antibodies Trastuzumab and Pertuzumab. Interaction of Trastuzumab with HER2 involves 3 loops in the juxtamembrane region of HER2 formed by amino acids 579-583 (loop1), 592-595 (loop2), as well as 615-625 (loop3) (see, e.g., Cho et al. (2003) *Nature* 421: 756-60). In those loops there are several key residues for HER2-Trastuzumab binding, including E580, D582, P594, F595, K615, Q624S (Satyanarayanajois et al. (2009) *Chem. Biol. Drug Des.* 74: 246-57).

Accordingly, in one embodiment, the HER2 antigen of the present invention includes one or more mutations to the residues that interfere with the binding of the HER2 antigen to Trastuzumab. Some exemplary residues include, but are not limited to E580, D582, P594, F595, K615, and Q624. Thus, in a more particular embodiment, the HER2 antigen of the present invention includes one or more mutations to the residues selected from the group consisting of E580, D582, P594, F595, K615, Q624, and combination thereof. In yet a more specific embodiment, the HER2 antigen of the present invention includes one or more mutations to the residues selected from E580, F595 and K615. In still another specific embodiment, the one more mutations to the HER2 antigen includes Ala substitutions to E580, F595 and K615 (e.g., E580A, F595A and K615A).

In another exemplary embodiment, the HER2 antigen comprises one or more mutations to the Pertuzumab binding domain. Pertuzumab binds close to a loop in the dimerization domain (domain II) of HER2, involving key residues H267, Y274, 5310, L317, H318 and K333. Mutations at the binding interface strongly reduce binding of Perjeta to HER2 (Franklin et al. (2004) *Cancer Cell* 5: 317-28). Additional amino acid residues in this binding domain potentially contribute to the Pertuzumab-HER2 interaction, including F279, V308, and P337.

Accordingly, in one embodiment, the HER2 antigen of the present invention includes one or more mutations to the residues that interfere with the binding of the HER2 antigen to Pertuzumab. In a more specific embodiment, the HER2 antigen of the present invention includes one or more mutations to the residues selected from the group consisting of H267, F279, V308, S310, L317, H318, K333 and P337, and combination thereof. In still another specific embodiment, the one or more mutations to the HER2 antigen includes Ala substitutions to H267, F279, V308, 5310, L317, H318, K333 and P337 (e.g. H267A, F279A, V308A, S310A, L317A, H318A, K333A and P337A).

In at least one aspect of the present invention, it was postulated that if the dimerization of HER2 was minimized this minimizes interaction and binding between the MVA encoded HER2 and other HER-family members, such as EGFR, HER3 or HER4, expressed by the MVA-transduced cell. Minimizing HER dimerization would be particularly advantageous as HER2 exerts its oncogenic potential through intracellular signaling initiated by dimerization. Accordingly, in one embodiment, the HER2 antigen of the present invention includes one or more mutations to the residues that interfere with dimerization of HER2. Some exemplary residues include, but are not limited to L317, H318, D277, and E280. Thus, in a more specific embodiment, the HER2 antigen of the present invention includes one or more mutations to the residues selected from the group consisting of L317, H318, D277, E280, and combinations thereof. In a more specific embodiment, the HER2 antigen of the present invention includes one or more mutations to the residues selected from D277, E280. In still another specific embodiment, the one more mutations to the HER2 antigen includes an Arg substitution to D277 (D277R) and a Lys substitution to E280 (E280K).

In additional aspects, it was postulated that if the tyrosine kinase activity was minimized this minimizes downstream activation of cell signals that might induce cell proliferation and angiogenesis. Accordingly, in one embodiment, the HER2 antigen of the present invention includes one or more mutations to the residues that interfere with tyrosine kinase activity of HER2. An exemplary residue includes, but is not limited to K753. Thus, in a more specific embodiment, the HER2 antigen of the present invention includes a mutation to the K753 residue. In a more specific embodiment, the HER2 antigen of the present invention includes a Met substitution to residue K753 (K753M).

In still additional aspects, it was postulated that if the potential phosphorylation sites were eliminated this minimizes downstream activation of cell signals that might induce cell proliferation and angiogenesis. Accordingly, in one embodiment, the HER2 antigen of the present invention includes one or more mutations to the residues that interfere with potential phosphorylation sites in HER2. Some exemplary residues include, but are not limited to amino acids 1139 to 1248 and Y1023. Thus, in a more specific embodiment, the HER2 antigen of the present invention includes one or more mutations to the residues selected from amino acids 1139 to 1248, Y1023, and combination thereof. In a more specific embodiment, the HER2 antigen of the present invention includes a deletion of amino acids 1139 to 1248 and/or a substitution of Y1023 to Ala (Y1023A).

In one preferred embodiment, the HER2 antigen comprises one or more mutations to the Pertuzumab binding domain, Trastuzumab binding domain, dimerization domain, kinase domain, and/or phosphorylation domain found in HER2. Exemplary Mutations to the HER2 antigen (based on NP 004439.2) in the previously described domains are illustrated below as synthetic HER2v2.

1 MELAALCRWG LLLALLPPGA ASTQVCTGTD MKLRLPASPE THLDMLRHLY QGCQVVQGNL

61 ELTYLPTNAS LSFLQDIQEV QGYVLLAHNQ VRQVPLQRLR IVRGTQLFED NYALAVLDNG

121 DPLNNTTPVT GASPGGLREL QLRSLTEILK GGVLIQRNPQ LCYQDTILWK DIFHKNNQLA

181 LTLIDTNRSR ACEPCSPMCK GSRCWGESSE DCQSLTRTVC AGGCARCKGP LPTDCCHEQC

241 AAGCTGPKHS DCLACLHFNH SGICELACPA LVTYNTRTAK SMPNPEGRYT FGASCVTACP

301 YNYLSTDAGA CTLVCPAANQ EVTAEDGTQR CEACSKACAR VCYGLGMEHL REVRAVTSAN

361 IQEFAGCKKI FGSLAFLPES FDGDPASNTA PLQPEQLQVF ETLEEITGYL YISAWPDSLP

421 DLSVFQNLQV IRGRILHNGA YSLTLQGLGI SWLGLRSLRE LGSGLALIHH NTHLCFVHTV

481 PWDQLFRNPH QALLHTANRP EDECVGEGLA CHQLCARGHC WGPGPTQCVN CSQFLRGQEC

541 VEECRVLQGL PREYVNARHC LPCHPECQPQ NGSVTCFGPA ADQCVACAHY KDPPACVARC

601 PSGVKPDLSY MPIWAFPDEE GACQPCPINC THSCVDIDDK GCPAEQRASP LTSIISAVVG

661 ILLVVVLGVV FGILIKRRQQ KIRKYTMRRL LQETELVEPL TPSGAMPNQA QMRILKETEL

721 RKVKVLGSGA FGTVYKGIWI PDGENVKIPV AIMVLRENTS PKANKEILDE AYVMAGVGSP

781 YVSRLLGICL TSTVQLVTQL MPYGCLLDHV RENRGRLGSQ DLLNWCMQIA KGMSYLEDVR

841 LVHRDLAARN VLVKSPNHVK ITDFGLARLL DIDETEYHAD GGKVPIKWMA LESILRRRFT

901 HQSDVWSYGV TVWELMTFGA KPYDGIPARE IPDLLEKGER LPQPPICTID VYMIMVKCWM

961 IDSECRPRFR ELVSEFSRMA RDPQRFVVIQ NEDLGPASPL DSTFYRSLLE DDDMGDLVDA

1021 EEALVPQQGF FCPDRAPGAG GMVHHRHRSS STRSGGGDLT LGLEPSEEEA PRSPLAPSEG

1081 AGSDVFDGDL GMGAAKGLQS LPTHDPSPLQ RYSEDPTVPL PSETDGYVAP LTCSPQPE

1141 ~~NQPDVRPQPP~~ ~~SPREGPLPAA~~ ~~RPAGATLERP~~ ~~KTLSPGKNGV~~ ~~VKDVFAFGGA~~ ~~VENPEYLTPQ~~

1201 ~~GGAAPQPHPP~~ ~~PAFSPAFDNL~~ ~~YYWDQDPPER~~ ~~GAPPSTFKGT~~ ~~PTAENPEY~~LG LDVPV

Amino Acid Sequence of HER2_v2. (SEQ ID: NO 13) Synthetic HER_version2 shown above is based on HER2 NP_004439.2. Mutated amino acids are shown by underlines and strikethrough Amino acids 579-625 are the binding site for trastuzumab Amino acids 267-337 are the binding site for pertuzumab. Amino acids 274-288 are the residues for the dimerization domain Amino acids 721-987 are the residues for the kinase domian. Amino acids 1139-1248 are the residues in the phosphorylation domain.

In accordance with the defined advantages herein, in various embodiments the present invention includes a synthetic HER2 antigen wherein one or more amino acids of the HER2 are mutated to prevent the HER2 antigen from binding a HER2 antibody. In a more preferred embodiment, the synthetic HER2 antigen is mutated to prevent binding of an antibody selected from pertuzumab, trastuzumab, and ado-trastuzumab emtansine.

In other embodiments, the synthetic HER2 antigen comprises one or more mutations to prevent extracellular dimerization, tyrosine kinase activity, and/or phosphorylation of the HER2 antigen (once expressed by the rMVA). In further specific embodiments, the synthetic HER2 antigen comprises one or more mutations to at least one of 3 loops in a juxtamembrane region of HER2.

In various further embodiments, the present invention includes a nucleic acid encoding a HER2 antigen comprising The inventors determined that one or more modifications of the Brachyury antigens and/or nucleic acids encoding the Brachyury antigens as described herein increase the efficacy of the combination therapy. More specifically, one or more mutations were made to the nuclear localization signal (NLS) domain in order to minimize and/or avoid any nuclear localization of the Brachyury antigen by a host cell.

Accordingly, in various embodiments, the synthetic Brachyury polypeptide includes one more mutations to prevent nuclear localization of Brachyury. "Nuclear localization" can be defined as localization and/or transport to the nucleus. Conducting assays to determine whether one or more mutations prevent nuclear localization of a Brachyury antigen is within the ordinary skill in the art. Such assays can include immunofluorescence analysis and immunofluorescence microscopy.

In more specific embodiments, the synthetic Brachyury polypeptide includes one more mutations in the NLS domain. In a more specific and preferred embodiment, the synthetic Brachyury polypeptide has deleted amino acids 286-293 of the Brachyury antigen (GenBank reference NP_003172.1), as shown below.

```
  1 MSSPGTESAG KSLQYRVDHL LSAVENELQA GSEKGDPTER ELRVGLEESE LWLRFKELTN

61 EMIVTKNGRR MFPVLKVNVS GLDPNAMYSF LLDFVAADNH RWKYVNGEWV PGGKPEPQAP

121 SCVYIHPDSP NFGAHWMKAP VSFSKVKLTN KLNGGGQIML NSLHKYEPRI HIVRVGGPQR

181 MITSHCFPET QFIAVTAYQN EEITALKIKY NPFAKAFLDA KERSDHKEMM EEPGDSQQPG

241 YSQWGWLLPG TSTLCPPANP HPQFGGALSL PSTHSCDRYP TLRSHRSSPY PSPYAHRNNS

301 PTYSDNSPAC LSMLQSHDNW SSLGMPAHPS MLPVSHNASP PTSSSQYPSL WSVSNGAVTP

361 GSQAAAVSNG LGAQFFRGSP AHYTPLTHPV SAPSSSGSPL YEGAAAATDI VDSQYDAAAQ

421 GRLIASWTPV SPPSM
```

SEQ ID NO: 1. In additional embodiments, the present invention includes a nucleic acid encoding a HER2 antigen having at least 90%, 95%, 97% 98%, or 99% identity to SEQ ID NO:1.

In one embodiment, the present invention includes a nucleic acid comprising SEQ ID NO:2, which encodes the HER2 antigen of SEQ ID NO:1. In additional embodiments, the present invention includes a nucleic acid encoding a HER2 antigen, the nucleic acid having at least 90%, 95%, 97% 98%, or 99% identity to SEQ ID NO:2.

In various additional embodiments, the present invention includes a nucleic acid encoding a HER2 antigen comprising SEQ ID NO: 13. In additional embodiments, the present invention includes a nucleic acid encoding a HER2 antigen having at least 90%, 95%, 97% 98%, or 99% identity to SEQ ID NO:13.

In one embodiment, the present invention includes a nucleic acid comprising SEQ ID NO:14, which encodes the HER2 antigen of SEQ ID NO:13. In additional embodiments, the present invention includes a nucleic acid encoding a HER2 antigen, the nucleic acid having at least 90%, 95%, 97% 98%, or 99% identity to SEQ ID NO:14.

Synthetic Brachyury Proteins

As illustrated previously, the addition of a second disease/tumor associate antigen encoded by the MVA enhanced the anti-tumor response/activity of the combination therapy. In accordance therewith, in various embodiments of the invention, the recombinant MVA additionally encodes a Brachyury antigen.

Amino Acid Sequence of an exemplary modified Brachyury. The Conserved core motif residues RSSPYPSP within a potential NLS of Brachyury were deleted (shown by strikethrough) (SEQ ID NO:3).

In more specific embodiments, the present invention includes a nucleic acid encoding a Brachyury antigen selected from the group consisting of SEQ ID NO: 3, SEQ ID NO: 5, and SEQ ID NO:7. In a preferred aspect, the various embodiments of the present invention include a nucleic acid encoding SEQ ID NO:3.

In at least one specific aspect, the nucleic acid encoded by SEQ ID NO:3 is particularly advantageous as SEQ ID NO: 3 is configured to prevent and/or minimize the Brachyury antigen encoded by the MVA from being localized and/or transported to the nucleus where there may be a possibility of undesired transcriptional activity.

In accordance with defined advantages to the combination therapy, in various aspects, the embodiments the present invention includes a nucleic acid encoding a Brachyury antigen comprising SEQ ID NO: 3. In additional aspects, the embodiments of the present invention include a nucleic acid encoding a Brachyury antigen having at least 90%, 95%, 97% 98%, or 99% identity to SEQ ID NO:3.

In further aspects, the embodiments of the present invention include a nucleic acid comprising SEQ ID NO:4, which encodes the Brachyury antigen of SEQ ID NO:3. In additional aspects, the embodiments of the present invention include a nucleic acid encoding a Brachyury antigen, the nucleic acid having at least 90%, 95%, 97% 98%, or 99% identity to SEQ ID NO:4.

CD40L

As illustrated by the present disclosure the inclusion of CD40L as part of the pharmaceutical combination and related method further enhances the decrease in tumor volume, prolongs progression-free survival and increase survival rate realized by the present invention. Thus, in various embodiments, the pharmaceutical combination further comprises administering CD40L to a cancer patient.

While CD40 is constitutively expressed on many cell types, including B cells, macrophages, and dendritic cells, its ligand CD40L is predominantly expressed on activated T helper cells. The cognate interaction between dendritic cells and T helper cells early after infection or immunization 'licenses' dendritic cells to prime CTL responses. Dendritic cell licensing results in the up-regulation of co-stimulatory molecules, increased survival and better cross-presenting capabilities. This process is mainly mediated via CD40/CD40L interaction. However, various configurations of CD40L are described, from membrane bound to soluble (monomeric to trimeric) which induce diverse stimuli, either inducing or repressing activation, proliferation, and differentiation of APCs.

As shown by the results of Example 19, the MVA encoded CD40L presents a much safer alternative to a cancer patient, as the CD40L encoded by MVA presents decreased toxicity compared to as a soluble CD40 agonist.

In one or more preferred embodiments, CD40L is encoded by the MVA of the present invention. In even more preferred embodiments, the CD40L comprises a nucleic acid encoding SEQ ID NO: 11. In still more preferred embodiments, the CD40L comprises a nucleic acid having at least 90%, 95%, 97% 98%, or 99% identity to SEQ ID NO:12. In a most preferred embodiment, the CD40L comprises SEQ ID NO:12.

Exemplary Antibodies

In various embodiments, the pharmaceutical combination and related methods include an antibody specific to an antigen that is expressed on the cell membrane of a tumor cell. It is understood in the art that in many cancers, one or more antigens are expressed or overexpressed on the tumor cell membrane (see, e.g., Duerig et al. (2002) *Leukemia* 16: 30-5; Mocellin et al. (2013) *Biochim. Biophys. Acta* 1836: 187-96; Arteaga (2017); Finn (2018) *J Immunol.* 200: 385-91; Ginaldi et al. (1998) *J. Clin. Pathol.* 51: 364-9). Assays for determining whether an antigen is expressed or overexpressed on a tumor cells are readily understood in the art (Id), as well as methods for producing antibodies to a particular antigen.

In more specific embodiments, the pharmaceutical combination and related methods include an antibody, wherein in the antibody is a) specific to an antigen that is expressed on a cell membrane of a tumor and b) comprises an Fc domain. In at least one aspect, the characteristics of the antibody (e.g., a) and b)) enable the antibody to bind to and interact with an effector cell, such as an NK cell, macrophage, basophil, neutrophil, eosinophil, monocytes, mast cells, and/or dendritic cells, and enable the antibody to bind a tumor antigen that is expressed on a tumor cell. In a preferred embodiment, the antibody comprises an Fc domain. In an additional preferred embodiment, the antibody is able to bind and interact with an NK cell.

Some exemplary antibodies to antigens expressed on tumor cells that are contemplated by the present disclosure include, but are not limited to, anti-CD20 (e.g., rituximab, ofatumumab, tositumomab), anti-CD52 (e.g., alemtuzumab, Campath® antibody), anti-EGFR (e.g., cetuximab, Erbitux® antibody, panitumumab), anti-CD2 (e.g., siplizumab), anti-CD37 (e.g., BI836826), anti-CD123 (e.g., JNJ-56022473), anti-CD30 (e.g., XmAb2513), anti-CD38 (e.g., daratumumab, Darzalex® antibody), anti-PDL1 (e.g., avelumab, atezolilzumab, durvalumab), anti-GD2 (e.g., 3F8, ch14.18, KW-2871, dinutuximab), anti-CEA, anti-MUC1, anti-FLT3, anti-CD19, anti-CD40, anti-SLAMF7, anti-CCR4, anti-B7-H3, anti-ICAM1, anti-CSF1R, anti-CA125 (e.g., oregovomab), anti-FRα (e.g. MOv18-IgG1, mirvetuximab soravtansine (IMGN853), MORAb-202), anti-mesothelin (e.g. MORAb-009) and anti-HER2 (e.g., trastuzumab, Herzuma® antibody, ABP 980, and/or pertuzumab).

In a more preferred embodiment, the antibody included as part of present invention includes an antibody that when administered to a patient binds to the corresponding antigen on a tumor cell and induces antibody dependent cell-mediated cytotoxicity (ADCC). In an even more preferred embodiment, the antibody comprises an antibody that is approved or in pre-approval for the treatment of a cancer.

In even more preferred embodiments, the antibody is an anti-HER2 antibody. In a most preferred embodiment, antibody is selected from pertuzumab, trastuzumab, Herzuma® antibody, ABP 980, and ado-trastuzumab emtansine.

In additional embodiments, the antibody comprises a fusion of one or more antibodies and/or antibody fragments. Exemplary fusion antibodies and/or antibody fragments include, but are not limited to Bispecific Killer cell Engagers (BiKE) and Trispecific Killer cell Engagers (TriKE). BiKEs and TriKEs are known to effectively drive NK cell anti-tumor effects and enable NK cell-mediated ADCC (see, e.g., Tay et al. (2016) *Hum. Vaccin. Immunother.* 12: 2790-96). It is contemplated that the 161533 TriKE and/or the 1633 BiKE can be used as the antibody in the present invention. It is additionally contemplated that the antibodies of the present invention can be embodied as Bispecific T cell engagers, or BiTEs (see, e.g., Huehls et al. (2015) *Immunol. Cell Biol.* 93: 290-296).

Recombinant Poxviruses

In one or more aspects of the present invention, the nucleotides and proteins sequences of the present disclosure can be included in a recombinant poxvirus.

In the various embodiments of the present disclosure, the recombinant poxvirus is preferably an orthopoxvirus such as, but not limited to, a vaccinia virus, a Modified Vaccinia Ankara (MVA) virus, MVA-BN, or a derivative of MVA-BN.

Examples of vaccinia virus strains are the strains Temple of Heaven, Copenhagen, Paris, Budapest, Dairen, Gam, MRIVP, Per, Tashkent, TBK, Tom, Bern, Patwadangar, BIEM, B-15, Lister, EM-63, New York City Board of Health, Elstree, Ikeda and WR. A preferred vaccinia virus (VV) strain is the Wyeth (DRYVAX) strain (U.S. Pat. No. 7,410,644).

Recombinant MVA

In more preferred embodiments of the present invention, the one or more proteins and nucleotides disclosed herein are included in a recombinant MVA. As described and illustrated by the present disclosure, the intravenous administration of the recombinant MVAs of the present disclosure induces in various aspects an enhanced immune response in cancer patients. Thus, in one or more preferred embodiments, the invention includes a recombinant MVA comprising one or more nucleic acids encoding HER2, Brachyury, and/or CD40L described herein. In more preferred embodiments, the recombinant MVA comprises one or more nucleic acids encoding the synthetic HER2 and synthetic Brachyury antigens described herein. In another more preferred embodiment, the recombinant MVA comprises one or more nucleic acids encoding the synthetic HER2 and the synthetic Brachyury antigens described herein as well as CD40L. In still another more preferred embodiment, the recombinant MVA comprises one or more nucleic acids encoding SEQ ID NO:1 or SEQ ID NO: 13 (Her2), and SEQ ID NO: 3 (Brachyury). In yet another preferred embodiment, the recombinant MVA comprises one or more nucleic acids encoding SEQ ID NO:1 or SEQ ID NO: 13, SEQ ID NO: 3, and CD40L. In a more preferred embodiment, the recombinant MVA comprises one or more nucleic acids encoding SEQ ID NO:1, SEQ ID NO: 3, SEQ ID NO: 11, and/or SEQ ID NO: 13. In a most preferred embodiment, the recombinant MVA comprises one or more nucleic acids encoding SEQ ID NO:13, SEQ ID NO:3, and SEQ ID NO:11

In additional embodiments, the recombinant MVA comprises one or more nucleic acids selected from the group consisting of SEQ ID NO:2, SEQ ID NO: 4, and/or SEQ ID NO: 14. In another more preferred embodiment, the recombinant MVA comprises one or more nucleic acids selected from the group consisting of SEQ ID NO:2, SEQ ID NO:4, and CD40L. In still another preferred embodiment, the recombinant MVA comprises one or more nucleic acids selected from the group consisting of SEQ ID NO:2, SEQ ID NO: 4, and SEQ ID NO: 12. In a more preferred embodiment, the recombinant MVA comprises SEQ ID NO: 2, SEQ ID NO: 4, and SEQ ID NO: 12. In a most preferred embodiment, the recombinant MVA comprises SEQ ID NO: 14, SEQ ID NO: 4, and SEQ ID NO:12.

Example of MVA virus strains that are useful in the practice of the present invention and that have been deposited in compliance with the requirements of the Budapest Treaty are strains MVA 572, deposited at the European Collection of Animal Cell Cultures (ECACC), Vaccine Research and Production Laboratory, Public Health Laboratory Service, Centre for Applied Microbiology and Research, Porton Down, Salisbury, Wiltshire SP4 OJG, United Kingdom, with the deposition number ECACC 94012707 on Jan. 27, 1994, and MVA 575, deposited under ECACC 00120707 on Dec. 7, 2000, MVA-BN, deposited on Aug. 30, 2000 at the European Collection of Cell Cultures (ECACC) under number V00083008, and its derivatives, are additional exemplary strains.

"Derivatives" of MVA-BN refer to viruses exhibiting essentially the same replication characteristics as MVA-BN, as described herein, but exhibiting differences in one or more parts of their genomes. MVA-BN, as well as derivatives thereof, are replication incompetent, meaning a failure to reproductively replicate in vivo and in vitro. More specifically in vitro, MVA-BN or derivatives thereof have been described as being capable of reproductive replication in chicken embryo fibroblasts (CEF), but not capable of reproductive replication in the human keratinocyte cell line HaCat (Boukamp et al. (1988), *J. Cell Biol.* 106: 761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, MVA-BN or derivatives thereof have a virus amplification ratio at least two-fold less, more preferably three-fold less than MVA-575 in Hela cells and HaCaT cell lines. Tests and assay for these properties of MVA-BN and derivatives thereof are described in WO 02/42480 (issued as U.S. Pat. No. 6,913,752) and WO 03/048184 (U.S. Pat. No. 7,759,116).

The term "not capable of reproductive replication" or "no capability of reproductive replication" in human cell lines in vitro as described in the previous paragraphs is, for example, described in WO 02/42480, which also teaches how to obtain MVA having the desired properties as mentioned above. The term applies to a virus that has a virus amplification ratio in vitro at 4 days after infection of less than 1 using the assays described in WO 02/42480 or in U.S. Pat. No. 6,761,893.

The term "failure to reproductively replicate" refers to a virus that has a virus amplification ratio in human cell lines in vitro as described in the previous paragraphs at 4 days after infection of less than 1. Assays described in WO 02/42480 or in U.S. Pat. No. 6,761,893 are applicable for the determination of the virus amplification ratio.

The amplification or replication of a virus in human cell lines in vitro as described in the previous paragraphs is normally expressed as the ratio of virus produced from an infected cell (output) to the amount originally used to infect the cell in the first place (input) referred to as the "amplification ratio." An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

In another embodiment, the recombinant poxvirus, including the synthetic nucleotides and proteins of the present invention can be embodied in an avipoxvirus, such as but not limited to, a fowlpox virus.

The term "avipoxvirus" refers to any avipoxvirus, such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus.

An example of a canarypox virus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of a Fowlpox virus are strains FP-1, FP-5, TROVAC (U.S. Pat. No. 5,766,598), PDXVAC-TC (U.S. Pat. No. 7,410,644), TBC-FPV (Therion Biologics-FPV), FP-1 is a Duvette strain modified to be used as a vaccine in one-day old chickens. The strain is a commercial fowlpox virus vaccine strain designated O DCEP 25/CEP67/239 October 1980 and is available from Institute Merieux, Inc. FP-5 is a commercial fowlpox virus vaccine strain of chicken embryo origin available from American Scientific Laboratories (Division of Schering Corp., Madison, Wis., United States Veterinary License No. 165, serial No. 30321).

Expression Cassettes/Control Sequences

In various aspects, the one or more nucleic acids described herein are embodied in in one or more expression cassettes in which the one or more nucleic acids are operatively linked to expression control sequences. "Operably linked" means that the components described are in relationship permitting them to function in their intended manner e.g., a promoter to transcribe the nucleic acid to be expressed. An expression control sequence operatively linked to a coding sequence is joined such that expression of the coding sequence is achieved under conditions compatible with the expression control sequences. The expression control sequences include, but are not limited to, appropriate promoters, enhancers, transcription terminators, a start codon at the beginning a protein-encoding open reading frame, splicing signals for introns, and in-frame stop codons. Suitable promoters include, but are not limited to, the SV40 early promoter, an RSV promoter, the retrovirus LTR, the adenovirus major late promoter, the human CMV immediate early I promoter, and various poxvirus promoters including, but not limited to the following vaccinia virus or MVA-derived and FPV-derived promoters: the 30K promoter, the 13 promoter, the PrS promoter, the PrS5E promoter, the Pr7.5K, the PrHyb promoter, the Pr13.5 long promoter, the 40K promoter, the MVA-40K promoter, the FPV 40K promoter, 30k promoter, the PrSynIIm promoter, the PrLE1 promoter, and the PR1238 promoter. Additional promoters are further described in WO 2010/060632, WO 2010/102822, WO 2013/189611, WO 2014/063832, and WO 2017/021776 which are incorporated fully by reference herein.

Additional expression control sequences include, but are not limited to, leader sequences, termination codons, polyadenylation signals and any other sequences necessary for the appropriate transcription and subsequent translation of the nucleic acid sequence encoding the desired recombinant protein (e.g., HER2, Brachyury, and/or CD40L) in the desired host system. The poxvirus vector may also contain additional elements necessary for the transfer and subsequent replication of the expression vector containing the nucleic acid sequence in the desired host system. It will further be understood by one skilled in the art that such vectors are easily constructed using conventional methods (Ausubel et al. (1987) in "Current Protocols in Molecular Biology," John Wiley and Sons, New York, N.Y.) and are commercially available.

In certain embodiments, the one or more recombinant MVAs of the present disclosure comprises one or more cytokines, such as IL-2, IL-6, IL-12, IL-15, IL-7, IL-21 RANTES, GM-CSF, TNF-α, or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as CD70, OX-40L or 4-1 BBL, or combinations of these molecules, can be used as biological adjuvants (see, for example, Salgaller et al. (1998) *J Surg. Oncol.* 68(2): 122-38; Lotze et al. (2000) *Cancer J. Sci. Am.* 6 (Suppl. 1): S61-6; Cao et al. (1998) *Stem Cells* 16 (Suppl 1): 251-60; Kuiper et al. (2000) *Adv. Exp. Med. Biol.* 465: 381-90). These molecules can be administered systemically (or locally) to the host. In several examples, IL-2, RANTES, GM-CSF, TNF-α, IFN-γ, G-CSF, LFA-3, CD72, B7-1, B7-2, B7-1 B7-2, CD70, OX-40L, 4-1 BBL and ICAM-1 are administered.

Methods and Dosing Regimens for Administering the Pharmaceutical Combination

In still further aspects, the present disclosure provides for one or more regimens for administration of the pharmaceutical combination and/or methods of the present invention. In at least one aspect, the regimens of the present invention increase the effectiveness of the pharmaceutical combination and/or therapy to reduce tumor volume and increase survival rate of a cancer patient.

Thus, in one embodiment, there is a pharmaceutical combination and/or method for reducing tumor size and/or increasing survival in a cancer patient comprising administering to the cancer patient a pharmaceutical combination of the present disclosure, wherein the recombinant MVA is administered at the same time or after administration of the antibody.

In one specific exemplary embodiment, there is a pharmaceutical combination and/or method for reducing tumor size and/or increasing survival in a cancer patient comprising a) administering to the cancer patient an antibody, wherein the antibody comprises an Fc domain and is specific to an antigen that is expressed on the cell membrane of a tumor cell; and b) intravenously administering to the cancer patient a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced cytotoxic T cell response; wherein b) is administered at the same time or after a).

In several specific embodiments, the recombinant MVA can be administered at the same time as the antibody. In other specific embodiments, the recombinant MVA is administered after or subsequent to administration of the antibody. In various embodiments, the recombinant MVA is administered within 1 to 6 days after the antibody.

In more preferred embodiments, the recombinant MVA is administered within 0 to 5 days, 0 to 4 days, 0 to 3 days, or 0-2 days after administration of the antibody. In most preferred embodiment, the recombinant MVA is administered 0 to 3 days after the antibody is administered.

In various additional embodiments, the recombinant MVA is administered within 1 to 6 days after the antibody. In more preferred embodiments, the recombinant MVA is administered within 1 to 5 days, 1 to 4 days, 1 to 3 days, or 1-2 days after administration of the antibody. In most preferred embodiment, the recombinant MVA is administered 1 to 3 days after the antibody is administered.

In one advantageous aspect of the present invention, administering the recombinant MVA at the same time or after the antibody enables the administered antibody to bind tumor cells at the same time or prior to enhancement of the NK cell response that results from administering the recombinant MVA. Accordingly, in an exemplary first step, an antibody is administered resulting in the antibody binding to the antigen on the surface of one or more tumor cells. In an exemplary second step, a recombinant MVA is intravenously administered which as described herein, enhances and/or increases both the subject's innate immune response (e.g., the NK cell response) and T cell response. The enhanced innate immune response aggressively targets and kills tumor cells having the bound antibody.

In another advantageous aspect, the regimens of the present invention are designed to effectively attack the tumor with the both the subject's innate immune and adaptive immune responses. In one exemplary aspect, the pharmaceutical combination is designed to a recombinant MVA intravenously administered at the same time or after the antibody administration, the recombinant MVA inducing an enhanced NK and innate immune response that attacks and kill those tumor cells having bound antibody. During the period in which the innate immune response is killing antibody-coated tumor cells, the recombinant MVA is also inducing a specific T cell response (including both CD8 and CD4 T cells) in the patient. The disclosed regimen is designed such that as the innate immune response e.g., NK cells, is naturally declining, an enhanced specific CD8/CD4 T cell response is killing tumor cells. The designed regimen is particularly advantageous, as the enhanced specific CD8/CD4 T cell response can kill those tumor cells that have potentially evaded a patient's innate and/or non-specific immune response.

In other aspects, the pharmaceutical combination of the present invention is administered as part of a homologous and/or heterologous prime-boost regimen. Illustrated in FIGS. 8A-13B, a homologous and/or heterologous prime boost regimen prolongs and reactivates enhanced NK cell responses as well as increases a subject's specific CD8 and CD4 T cell responses. Thus, in one or more embodiments there is a pharmaceutical combination and/or method for a reducing tumor size and/or increasing survival in a cancer patient comprising administering to the cancer patient a pharmaceutical combination of the present disclosure, wherein the pharmaceutical combination is administered as part of a homologous or heterologous prime-boost regimen. In more preferred aspect of the prime-boost regimen, the recombinant MVA is intravenously administered at the same time or after to the administration of the antibody.

Generation of Recombinant MVA Viruses Comprising Transgenes

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in *Molecular Cloning, A Laboratory Manual* (2nd ed., Sambrook et al., Cold Spring Harbor Laboratory Press (1989)), and techniques for the handling and manipulation of viruses are described in *Virology Methods Manual* (Mahy et al. (eds.), Academic Press (1996)). Similarly, techniques and know-how for the handling, manipulation and genetic engineering of MVA are described in *Molecular Virology: A Practical Approach* (Davison & Elliott (eds.), The Practical Approach Series, IRL Press at Oxford University Press, Oxford, U K (1993); see, e.g., "Chapter 9: Expression of genes by Vaccinia virus vectors") and *Current Protocols in Molecular Biology* (John Wiley & Son, Inc. (1998); see, e.g., "Chapter 16, Section IV: Expression of proteins in mammalian cells using vaccinia viral vector").

For the generation of the various recombinant MVA viruses disclosed herein, different methods may be applicable. The DNA sequence to be inserted into the virus can be placed into an *E. coli* plasmid construct into which DNA homologous to a section of DNA of the poxvirus has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of poxviral DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA virus. Recombination between homologous MVA viral DNA in the plasmid and the viral genome, respectively, can generate a poxvirus modified by the presence of foreign DNA sequences.

According to a preferred embodiment, a cell of a suitable cell culture as, e.g., CEF cells, can be infected with a MVA virus. The infected cell can be, subsequently, transfected with a first plasmid vector comprising a foreign or heterologous gene or genes, such as one or more of the nucleic acids provided in the present disclosure; preferably under the transcriptional control of a poxvirus expression control element. As explained above, the plasmid vector also comprises sequences capable of directing the insertion of the exogenous sequence into a selected part of the MVA viral genome. Optionally, the plasmid vector also contains a cassette comprising a marker and/or selection gene operably linked to a poxviral promoter. Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a MVA virus genome cloned as a bacterial artificial chromosome (BAC) and a linear foreign sequence flanked with DNA sequences homologous to sequences flanking the desired site of integration in the MVA virus genome.

The one or more nucleic acids of the present disclosure may be inserted into any suitable part of the MVA virus or MVA viral vector. Suitable parts of the MVA virus are non-essential parts of the MVA genome. Non-essential parts of the MVA genome may be intergenic regions or the known deletion sites 1-6 of the MVA genome. Alternatively or additionally, non-essential parts of the recombinant MVA can be a coding region of the MVA genome which is non-essential for viral growth. However, the insertion sites are not restricted to these preferred insertion sites in the MVA genome, since it is within the scope of the present invention that the nucleic acids of the present invention (e.g., HER2, Brachyury, and CD40L) and any accompanying promoters as described herein may be inserted anywhere in the viral genome as long as it is possible to obtain recombinants that can be amplified and propagated in at least one cell culture system, such as Chicken Embryo Fibroblasts (CEF cells).

Preferably, the nucleic acids of the present invention may be inserted into one or more intergenic regions (IGR) of the MVA virus. The term "intergenic region" refers preferably to those parts of the viral genome located between two adjacent open reading frames (ORF) of the MVA virus genome, preferably between two essential ORFs of the MVA virus genome. For MVA, in certain embodiments, the IGR is selected from IGR 07/08, IGR 44/45, IGR 64/65, IGR 88/89, IGR 136/137, and IGR 148/149.

For MVA virus, the nucleotide sequences may, additionally or alternatively, be inserted into one or more of the known deletion sites, i.e., deletion sites I, II, III, IV, V, or VI of the MVA genome. The term "known deletion site" refers to those parts of the MVA genome that were deleted through continuous passaging on CEF cells characterized at 20 passage 516 with respect to the genome of the parental virus from which the MVA is derived from, in particular the parental chorioallantois vaccinia virus Ankara (CVA) e.g., as described in Meisinger-Henschel et al. ((2007) *J. Gen. Virol.* 88: 3249-59).

Vaccines

In certain embodiments, the recombinant MVA of the present disclosure can be formulated as part of a vaccine. For the preparation of vaccines, the MVA virus can be converted into a physiologically acceptable form. In certain embodiments, such preparation is based on experience in the preparation of poxvirus vaccines used for vaccination against smallpox, as described, for example, in Stickl et al. ((1974) *Dtsch. med. Wschr.* 99: 2386-2392)

An exemplary preparation follows. Purified virus is stored at −80° C. with a titer of $5 \times 10^8$ TCID50/ml formulated in 10 mM Tris, 140 mM NaCl, pH 7.4. For the preparation of vaccine shots, e.g., $1 \times 10^8$-$1 \times 10^9$ particles of the virus can be lyophilized in phosphate-buffered saline (PBS) in the presence of 2% peptone and 1% human albumin in an ampoule, preferably a glass ampoule. Alternatively, the vaccine shots can be prepared by stepwise, freeze-drying of the virus in a formulation. In certain embodiments, the formulation contains additional additives such as mannitol, dextran, sugar, glycine, lactose, polyvinylpyrrolidone, or other additives, such as, including, but not limited to, antioxidants or inert gas, stabilizers or recombinant proteins (e.g. human serum albumin) suitable for in vivo administration. The ampoule is then sealed and can be stored at a suitable temperature, for example, between 4° C. and room temperature for several months. However, as long as no need exists, the ampoule is stored preferably at temperatures below −20° C., most preferably at about −80° C.

In various embodiments involving vaccination or therapy, the lyophilisate is dissolved in 0.1 to 0.5 ml of an aqueous solution, preferably physiological saline or Tris buffer such as 10 mM Tris, 140 mM NaCl pH 7.7. It is contemplated that the recombinant MVA, vaccine or pharmaceutical composition of the present disclosure can be formulated in solution in a concentration range of $10^4$ to $10^{10}$ TCID$_{50}$/ml, $10^5$ to $5 \times 10^8$ TCID$_{50}$/ml, $10^6$ to $10^8$ TCID$_{50}$/ml, or $10^7$ to $10^8$ TCID$_{50}$/ml. A preferred dose for humans comprises between $10^6$ to $10^{10}$ TCID$_{50}$, including a dose of $10^6$ TCID$_{50}$, $10^7$ TCID$_{50}$, $10^8$ TCID$_{50}$, $5 \times 10^8$ TCID$_{50}$, $10^9$ TCID$_{50}$, $5 \times 10^9$ TCID$_{50}$, or $10^{10}$ TCID$_{50}$. Optimization of dose and number of administrations is within the skill and knowledge of one skilled in the art.

In one or more preferred embodiments, as set forth herein, the recombinant MVA is administered to a cancer patient intravenously.

In additional embodiments, the antibody can be administered either systemically or locally, i.e., by intraperitoneal, parenteral, subcutaneous, intravenous, intramuscular, intranasal, intradermal, or any other path of administration known to a skilled practitioner.

Kits, Compositions, and Methods of Use

In various embodiments, the invention encompasses kits, pharmaceutical combinations, pharmaceutical compositions, and/or immunogenic combination, comprising the a) recombinant MVA that includes the nucleic acids described herein and b) one or more antibodies described herein.

It is contemplated that the kit and/or composition can comprise one or multiple containers or vials of a recombinant poxvirus of the present disclosure, one or more containers or vials of an antibody of the present disclosure, together with instructions for the administration of the recombinant MVA and antibody. It is contemplated that in a more particular embodiment, the kit can include instructions for administering the recombinant MVA and antibody in a first priming administration and then administering one or more subsequent boosting administrations of the recombinant MVA and antibody.

The kits and/or compositions provided herein may generally include one or more pharmaceutically acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycolic acids, polymeric amino acids, amino acid copolymers, lipid aggregates, or the like.

Certain Exemplary Embodiments

Embodiment 1 is a method of reducing tumor size and/or increasing survival in a cancer patient, the method comprising: a) intravenously administering to the cancer patient a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced cytotoxic T cell response as compared to an NK cell response and a T cell response induced by a non-intravenous administration of a recombinant MVA comprising a first nucleic acid encoding a first heterologous cancer-associated antigen; and b) administering to the cancer patient an antibody, wherein the antibody comprises an Fc domain and is specific to an antigen that is expressed or over-expressed on the cell membrane of a tumor cell; wherein administration of a) and b) to the cancer patient reduces tumor size in the cancer patient and/or increases the survival rate of the cancer patient as compared to a non-intravenous administration of a) or an administration of b) alone.

Embodiment 2 is a method of reducing tumor size and/or increasing survival in a cancer patient, the method comprising: (a) administering to the cancer patient an antibody, wherein the antibody comprises an Fc domain and is specific to an antigen that is expressed on the cell membrane of a tumor cell; and (b) intravenously administering to the cancer patient a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced cytotoxic T cell response as compared to an NK cell response and a T cell response induced by a non-intravenous administration of a recombinant MVA comprising a first nucleic acid encoding a first heterologous cancer-associated antigen; wherein administration of (a) and (b) to the cancer patient reduces tumor size in the cancer patient and/or increases the survival rate of the cancer patient as compared to an non-intravenous administration of (a) or an administration of (b) alone.

Embodiment 3 is a method of reducing tumor size and/or increasing survival in a cancer patient, the method comprising: (a) administering to the cancer patient an antibody, wherein the antibody comprises an Fc domain and is specific to an antigen that is expressed on the outer surface of cell membrane of a tumor cell that when administered induces ADCC in the cancer patient; and (b) intravenously administering to the cancer patient a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced T cell response as compared to an NK cell response and a T cell response induced by a non-intravenous administration of a recombinant MVA comprising a first nucleic acid encoding a first heterologous cancer-associated antigen; wherein administration of (a) and (b) to the cancer patient reduces tumor size in the cancer patient and/or increases the survival rate of the cancer patient as compared to an non-intravenous administration of (a) or an administration of (b) alone.

Embodiment 4 is the method of any one of embodiments 1-3, wherein the antibody is specific to an antigen that is overexpressed on the cell membrane of the tumor cell.

Embodiment 5 is the method of any one of Embodiments 1-4 further comprising intravenously administering CD40L to the cancer patient.

Embodiment 6 is the method of any one of Embodiments 1-5, wherein the CD40L is encoded by the MVA.

Embodiment 7 is the method of any one of Embodiments 1-6, wherein inducing an enhanced NK cell response comprises at least one of a) inducing an enhanced ADCC response and b) inducing NK cells to target and kill tumor cells having low MHC expression.

Embodiment 8 is the method of any one of Embodiments 1-6, wherein inducing an enhanced NK cell response comprises inducing an enhanced ADCC response.

Embodiment 9 is the method of any one of Embodiments 1-8, wherein the recombinant MVA is administered at the same time or after the antibody.

Embodiment 10 is the method of any one of Embodiments 1-8, wherein the recombinant MVA is administered after the antibody.

Embodiment 11 is the method of any one of Embodiments 1-10, wherein the the MVA further comprises a second nucleic acid encoding a second heterologous TAA.

Embodiment 12 is the method of any one of Embodiments 1-11, wherein the first and/or second TAA is selected from the group consisting of: 5-α-reductase, α-fetoprotein ("AFP"), AM-1, APC, April, B melanoma antigen gene ("BAGE"), β-catenin, Bc112, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-G1cNAc:RiMan(α1-6)R$_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, HER2, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), PRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST").

Embodiment 13 is the method of any one of Embodiments 1-12, wherein the antibody is an antibody approved for the treatment of a cancer patient.

Embodiment 14 is the method of any one of Embodiments 1-13, wherein the antibody is selected from the group consisting of: Anti-CD20 (e.g., rituximab; ofatumumab; tositumomab), Anti-CD52 (e.g., alemtuzumab Campath®), Anti-EGFR (e.g., cetuximab Erbitux®, panitumumab), Anti-CD2 (e.g., Siplizumab), Anti-CD37 (e.g., BI836826), Anti-CD123 (e.g., JNJ-56022473), Anti-CD30 (e.g., XmAb2513), Anti-CD38 (e.g., daratumumab Darzalex®), Anti-PDL1 (e.g., avelumab, atezolilzumab, durvalumab), CTLA-4 (e.g., ipilumumab), Anti-GD2 (e.g., 3F8, ch14.18, KW-2871, dinutuximab), Anti-CEA, Anti-MUC1, Anti-FLT3, Anti-CD19, Anti-CD40, Anti-SLAMF7, Anti-CCR4, Anti-B7-H3, Anti-ICAM1, Anti-CSF1R, anti-CA125 (e.g. Oregovomab), anti-FRα (e.g. MOv18-IgG1, Mirvetuximab soravtansine (IMGN853), MORAb-202), anti-mesothelin (e.g. MORAb-009), and Anti-HER2

Embodiment 15 is the method of any one of Embodiments 1-14, wherein the antibody is specific to the HER2 antigen.

Embodiment 16 is the method of any one of Embodiments 1-15, wherein the antibody is selected from Pertuzumab, Trastuzumab, Herzuma, ABP 980, and Ado-trastuzumab emtansine.

Embodiment 17 is the method of any one of Embodiments 1-16, wherein the first and/or second TAA has been modified to prevent binding of the antibody to the first and/or second TAA.

Embodiment 18 is the method of any one of Embodiments 1-17, wherein the first TAA is HER2.

Embodiment 19 is the method of Embodiment 18, wherein one or more amino acids of the HER2 are mutated to prevent the HER2 antibody from binding the HER2 antigen.

Embodiment 20 is the method of any one of Embodiments 18-19, wherein the one or more amino acids of HER2 are mutated to prevent extracellular dimerization, tyrosine kinase activity, and/or phosphorylation of the HER2 polypeptide and/or antigen.

Embodiment 21 is the method of any one of Embodiments 18-20, wherein one or more mutations have been made to at least one of 3 loops in a juxtamembrane region of HER2.

Embodiment 22 is the method of any one of 18-21, wherein the 3 loops of the juxtamembrane region of HER2 is selected from amino acids 579-583 (loop1), 592-595 (loop2), and 615-625 (loop3).

Embodiment 23 is the method of any one of Embodiments 18-22, wherein the HER2 antigen comprises at least one mutation in at least one of amino acids H267, Y274, S310, L317, H318, K333, E580, D582, P594, F595, K615, and Q624.

Embodiment 24 is the method of any one of Embodiments 18-23, wherein the HER2 antigen comprises at least one mutation selected from the group consisting of: E580A, F595A, K615A, S310A, H318A, L317A, D277R, E280K, K573M, and Y1023A.

Embodiment 25 is the method of any one of Embodiments 18-24, wherein the HER2 antigen comprises at least one mutation to amino acids 1139-1248.

Embodiment 26 is the method of any one of Embodiments 18-25, wherein the HER2 antigen comprises at least one deletion to amino acids 1139-1248.

Embodiment 27 is the method of any one of Embodiments 18-26, wherein the HER2 antigen comprises a deletion of amino acids 1139-1248.

Embodiment 28 is the method of any one of Embodiments 18-27, wherein the first nucleic acid encodes a HER2 antigen having at least 90%, 95%, 97% 98%, or 99% identity to SEQ ID NO:1.

Embodiment 29 is the method of any one of Embodiments 18-28, wherein the first nucleic acid encodes a HER2 antigen comprising SEQ ID NO:1.

Embodiment 30 is the method of any one of Embodiments 18-29, wherein the first nucleic acid encodes a HER2 antigen, the first nucleic acid having at least 90%, 95%, 97% 98%, or 99% identity to SEQ ID NO:2.

Embodiment 31 is the method of any one of Embodiments 18-30, wherein the first nucleic acid comprises SEQ ID NO:2.

Embodiment 32 is the method of any one of Embodiments 1-31, wherein the MVA comprises a second nucleic acid encoding a second heterologous TAA different from the first TAA.

Embodiment 33 is the method of Embodiment 32, wherein the second TAA is Brachyury.

Embodiment 34 is the method of Embodiment 33, wherein the Brachyury antigen comprises one or more mutations that prevent nuclear localization of the Brachyury antigen.

Embodiment 35 is the method of any one of Embodiments 33-34, wherein the Brachyury antigen comprises one or more mutations to the nuclear localization signal (NLS) domain.

Embodiment 36 is the method of any one of Embodiments 33-35, wherein the Brachyury antigen has the NLS domain deleted.

Embodiment 37 is the method of any one of Embodiments 33-36, wherein the second nucleic acid comprises a Brachyury antigen having at least 90%, 95%, 97% 98%, or 99% identity to SEQ ID NO:3.

Embodiment 38 is the method of any one of Embodiments 33-37, wherein the second nucleic acid comprises SEQ ID NO:3.

Embodiment 39 is the method of any one of Embodiments 33-38, wherein the second nucleic acid encodes a Brachyury antigen, the second nucleic acid having at least 90%, 95%, 97% 98%, or 99% identity to SEQ ID NO:4.

Embodiment 40 is the method of any one of Embodiments 33-39, wherein the second nucleic acid comprises SEQ ID NO:4.

Embodiment 41 is the method of any one of Embodiments 1-40, wherein the antibody is selected from the group consisting of: Anti-CD20 (rituximab; ofatumumab; tositumomab), Anti-CD52 (alemtuzumab Campath®), Anti-EGFR (cetuximab Erbitux® panitumumab), Anti-CD38 (daratumumab Darzalex®), Anti-PDL1 (avelumab), Anti-CTLA4 (ipilimumab), Anti-GD2 (3F8, ch14.18, KW-2871, dinutuximab), Anti-CEA, Anti-Muc1, Anti-FLT3L, Anti-CD19, Anti-CD40, Anti-SLAMF7, Anti-CCR4, Anti-B7-H3, Anti-ICAM1, Anti-CSF1R, and Anti-HER2.

Embodiment 42 is the method of any one of Embodiments 1-41, wherein the antibody is specific to the HER2 antigen.

Embodiment 43 is the method of Embodiment 42, wherein the anti-HER2 antibody is selected from Pertuzumab, Trastuzumab, and Ado-trastuzumab emtansine.

Embodiment 44 the method of any one of Embodiments 1-43, wherein the antibody and the MVA are administered as a homologous prime-boost regimen.

Embodiment 45 is the method of any one of Embodiments 1-44, wherein the MVA is MVA-BN, or a derivative of MVA-BN.

Embodiment 46 is the method of any one of Embodiments 1-45, wherein the cancer patient is suffering from and/or has been diagnosed with a cancer selected from the group consisting of breast cancer, lung cancer, head and neck cancer, thyroid, melanoma, gastric cancer, bladder cancer, kidney cancer, liver cancer, melanoma, pancreatic cancer, prostate cancer, ovarian cancer, or colorectal cancer.

Embodiment 47 is a pharmaceutical combination for use in reducing tumor size and/or increasing survival in a cancer patient, the combination comprising: a) a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced T cell response as compared to an NK cell response and a T cell response induced by a non-intravenous administration of a recombinant MVA virus comprising a nucleic acid encoding a heterologous TAA; and b) an antibody, wherein the antibody comprises an Fc domain and is specific to an antigen that is expressed on the cell membrane of a tumor cell; wherein administration of a) and b) to the cancer patient reduces tumor size and/or increases the survival rate of the cancer patient as compared to an non-IV administration of a) or an administration of b) alone.

Embodiment 48 is a pharmaceutical combination for use in reducing tumor size and/or increasing survival in a cancer patient, the combination comprising: a) a recombinant modified vaccinia virus Ankara (MVA) comprising a first nucleic acid encoding a first heterologous tumor-associated antigen (TAA) that when administered intravenously induces both an enhanced Natural Killer (NK) cell response and an enhanced T cell response as compared to an NK cell response and a T cell response induced by a non-intravenous administration of a recombinant MVA comprising a nucleic acid encoding a heterologous TAA; and b) an antibody, wherein the antibody comprises an Fc domain and is specific to an antigen that is expressed on the cell membrane of a tumor cell that when the antibody is administered, the antibody binds to the antigen on the tumor cell in the human cancer patient and induces antibody dependent cell-mediated cytotoxicity (ADCC); wherein administration of a) and b) to the cancer patient reduces tumor size and/or increases the survival rate of the cancer patient as compared to an non-IV administration of a) or an administration of b) alone.

Embodiment 49 is the pharmaceutical combination of any one of Embodiments 47-48, wherein the CD40L is encoded by the recombinant MVA.

Embodiment 50 is the pharmaceutical combination of any one of Embodiments 47-49, wherein the recombinant MVA further comprises a second nucleic acid encoding a second heterologous TAA.

Embodiment 51 is the pharmaceutical combination of any one of Embodiments 47-50, wherein the first and/or second TAA is selected from the group consisting of: 5-α-reductase, α-fetoprotein ("AFP"), AM-1, APC, April, B melanoma antigen gene ("BAGE"), β-catenin, Bcl12, bcr-abl, Brachyury, CA-125, caspase-8 ("CASP-8", also known as "FLICE"), Cathepsins, CD19, CD20, CD21/complement receptor 2 ("CR2"), CD22/BL-CAM, CD23/F$_c$εRII, CD33, CD35/complement receptor 1 ("CR1"), CD44/PGP-1, CD45/leucocyte common antigen ("LCA"), CD46/membrane cofactor protein ("MCP"), CD52/CAMPATH-1, CD55/decay accelerating factor ("DAF"), CD59/protectin, CDC27, CDK4, carcinoembryonic antigen ("CEA"), c-myc, cyclooxygenase-2 ("cox-2"), deleted in colorectal cancer gene ("DCC"), DcR3, E6/E7, CGFR, EMBP, Dna78, farnesyl transferase, fibroblast growth factor-8a ("FGF8a"), fibroblast growth factor-8b ("FGF8b"), FLK-1/KDR, folic acid receptor, G250, G melanoma antigen gene family ("GAGE-family"), gastrin 17, gastrin-releasing hormone, ganglioside 2 ("GD2")/ganglioside 3 ("GD3")/ganglioside-monosialic acid-2 ("GM2"), gonadotropin releasing hormone ("GnRH"), UDP-G1cNAc:RiMan(α1-6)R$_2$ [GlcNAc to Man(α1-6)] β1,6-N-acetylglucosaminyltransferase V ("GnT V"), GP1, gp100/Pme117, gp-100-in4, gp15, gp75/tyrosine-related protein-1 ("gp75/TRP-1"), human chorionic gonadotropin ("hCG"), heparanase, HER2, human mammary tumor virus ("HMTV"), 70 kiloDalton heat-shock protein ("HSP70"), human telomerase reverse transcriptase ("hTERT"), insulin-like growth factor receptor-1 ("IGFR-1"), interleukin-13 receptor ("IL-13R"), inducible nitric oxide synthase ("iNOS"), Ki67, KIAA0205, K-ras, H-ras, N-ras, KSA, LKLR-FUT, melanoma antigen-encoding gene 1 ("MAGE-1"), melanoma antigen-encoding gene 2 ("MAGE-2"), melanoma antigen-encoding gene 3 ("MAGE-3"), melanoma antigen-encoding gene 4 ("MAGE-4"), mammaglobin, MAP17, Melan-A/melanoma antigen recognized by T-cells-1 ("MART-1"), mesothelin, MIC A/B, MT-MMPs, mucin, testes-specific antigen NY-ESO-1, osteonectin, p15, P170/MDR1, p53, p97/melanotransferrin, PAI-1, platelet-derived growth factor ("PDGF"), μPA, PRAME, probasin, progenipoietin, prostate-specific antigen ("PSA"), prostate-specific membrane antigen ("PSMA"), RAGE-1, Rb, RCAS1, SART-1, SSX-family, STAT3, STn, TAG-72, transforming growth factor-alpha ("TGF-α"), transforming growth factor-beta ("TGF-β"), Thymosin-beta-15, tumor necrosis factor-alpha ("TNF-α"), TP1, TRP-2, tyrosinase, vascular endothelial growth factor ("VEGF"), ZAG, p16INK4, and glutathione-S-transferase ("GST")

Embodiment 52 is the pharmaceutical combination of any one of Embodiments 47-51, wherein the first TAA is HER2.

Embodiment 53 is the pharmaceutical combination of Embodiment 52, wherein the HER2 antigen comprises at least one mutation selected from the group consisting of: E580A, F595A, K615A, S310A, H318A, L317A, D277R, E280K, K573M, and Y1023A.

Embodiment 54 is the pharmaceutical combination of any one of Embodiments 52-53, wherein the first nucleic acid comprises a HER2 antigen having at least 90%, 95%, 97% 98%, or 99% identity to SEQ ID NO:1.

Embodiment 55 is the pharmaceutical combination of any one of Embodiments 52-54, wherein the first nucleic acid comprises SEQ ID NO:1.

Embodiment 56 is the pharmaceutical combination of any one of Embodiments 52-55, wherein the first nucleic acid encodes a HER2 antigen, the first nucleic acid having at least 90%, 95%, 97% 98%, or 99% identity to SEQ ID NO:2.

Embodiment 57 is the pharmaceutical combination of any one of Embodiments 52-56, wherein the first nucleic acid comprises SEQ ID NO:2.

Embodiment 58 is the pharmaceutical combination of any one of Embodiments 47-57, wherein the MVA comprises a second nucleic acid encoding a second heterologous TAA different from the first TAA.

Embodiment 59 is the pharmaceutical combination of Embodiment 58, wherein the second TAA is Brachyury.

Embodiment 60 is the pharmaceutical combination of Embodiment 59, wherein the second nucleic acid comprises a Brachyury antigen having at least 90%, 95%, 97% 98%, or 99% identity to SEQ ID NO:3.

Embodiment 61 is the pharmaceutical combination of any one of Embodiments 59-60, wherein the second nucleic acid encodes an antigen comprising SEQ ID NO:3.

Embodiment 62 is the pharmaceutical combination of any one of Embodiments 59-61, wherein the second nucleic acid encodes a Brachyury antigen, the second nucleic acid having at least 90%, 95%, 97% 98%, or 99% identity to SEQ ID NO:4.

Embodiment 63 is the pharmaceutical combination of any one of Embodiments 59-62, wherein the second nucleic acid comprises SEQ ID NO:4.

Embodiment 64 is the pharmaceutical combination of any one of Embodiments 47-63, wherein the antibody is selected from the group consisting of: anti-CD20 (e.g., rituximab, ofatumumab, tositumomab), anti-CD52 (e.g., alemtuzumab, Campath® antibody), anti-EGFR (e.g., cetuximab, Erbitux® antibody, panitumumab), anti-CD2 (e.g., siplizumab), anti-CD37 (e.g., BI836826), anti-CD123 (e.g., JNJ-56022473), anti-CD30 (e.g., XmAb2513), anti-CD38 (e.g., daratumumab, Darzalex® antibody, anti-PDL1 (e.g., avelumab, atezolilzumab, durvalumab), CTLA-4 (e.g., ipilumumab), anti-GD2 (e.g., 3F8, ch14.18, KW-2871, dinutuximab), anti-CEA, anti-MUC1, anti-FLT3, anti-CD19, anti-CD40, anti-SLAMF7, anti-CCR4, anti-B7-H3, anti-ICAM1, anti-CSF1R, anti-CA125 (e.g., oregovomab), anti-FRα (e.g. MOv18-IgG1, mirvetuximab soravtansine (IMGN853), MORAb-202), anti-mesothelin (e.g., MORAb-009), and anti-HER2.

Embodiment 65 is the pharmaceutical combination of any one of Embodiments 47-64, wherein the antibody is specific to the HER2 antigen.

Embodiment 66 is the pharmaceutical combination of Embodiment 65, wherein the antibody is selected from pertuzumab, trastuzumab, Herzuma® antibody, ABP 980, and ado-trastuzumab emtansine.

Embodiment 67 is the pharmaceutical combination of any one of Embodiments 47-66, wherein the MVA is MVA-BN or a derivative of MVA-BN.

Embodiment 68 is a method for inducing an enhanced Natural Killer (NK) response in a cancer patient comprising administering a pharmaceutical combination of any one of Embodiments 47-66, wherein administering the combination enhances the NK cell response of the cancer patient as compared to a non-intravenously administered combination of a) or an administration of b) alone.

Embodiment 69 is a method for inducing both an enhanced innate and an enhanced adaptive immune response in a cancer patient comprising administering a pharmaceutical combination of any one of Embodiments 47-67 wherein administering the combination enhances the NK cell response of the cancer patient as compared to a non-intravenously administered combination of (a) or an administration of (b) alone.

Embodiment 70 is the method of Embodiment 69, wherein the enhanced adaptive immune response comprises an enhanced T cell response.

Embodiment 71 is the method of Embodiment 70, wherein the enhanced T cell response comprises an enhanced CD8 T cell response and an enhanced CD4 T cell response.

Embodiment 72 is a method for enhancing antibody therapy in a cancer patient, the method comprising administering a pharmaceutical combination of any one of Embodiments 47-67, wherein administering the pharmaceutical combination enhances antibody dependent cell-mediated cytotoxicity (ADCC) induced by the antibody therapy, as compared to administering the antibody therapy alone.

Embodiment 73 is a method for enhancing the killing of tumor cells having reduced MHC levels in a cancer patient, the method comprising administering a pharmaceutical combination of any one of Embodiments 47-67, wherein administering the combination enhances the killing of tumor cells having reduced MHC levels as compared to administering b) alone.

Embodiment 74 is a method for treating a human cancer patient comprising administering to the cancer patient a pharmaceutical combination of any one of Embodiments 47-67.

Embodiment 75 is a method of any one of Embodiments 68-74, wherein the recombinant MVA is administered at the same time or after the antibody.

Embodiment 76 is a method of any one of Embodiments 68-74, wherein the recombinant MVA is administered after the antibody.

Embodiment 77 is a method of any one of Embodiments 68-75, wherein the recombinant MVA is administered 0 to 8 days, 0 to 7 days, 0 to 6 days, 0 to 5 days, 0 to 4 days, 0 to 3 days, 0 to 2 days, or 0 to 1 day after the antibody.

Embodiment 78 is a method of any one of Embodiments 68-75, wherein the recombinant MVA is administered 1 to 8 days, 1 to 7 days, 1 to 6 days, 1 to 5 days, 1 to 4 days, 1 to 3 days, 1 to 2 days, or 1 day after the antibody.

Embodiment 79 is a method of any one of Embodiments 68-77, wherein the recombinant MVA is administered 0 to 3 days, 0 to 2 days, 0 to 1 day after the antibody.

Embodiment 80 is a method of Embodiment 79, wherein the recombinant MVA is administered 0 to 3 days after the antibody.

Embodiment 81 is a method of any one of Embodiments 68-80, wherein the antibody and the MVA are administered as part of a homologous or heterologous prime boost regimen.

Embodiment 82 is a method of any one of Embodiments 68-80, wherein the antibody and the MVA are administered as part of a homologous prime boost regimen.

Embodiment 83 is a method of any one of Embodiments 1-45 and 68-82, wherein the cancer patient is suffering from and/or is diagnosed with a cancer selected from the group consisting of: breast cancer, lung cancer, head and neck cancer, thyroid, melanoma, gastric cancer, bladder cancer, kidney cancer, liver cancer, melanoma, pancreatic cancer, prostate cancer, ovarian cancer, or colorectal cancer.

Embodiment 84 is a pharmaceutical combination for use in reducing tumor volume and/or increasing survival of a cancer patient, the pharmaceutical combination comprising the pharmaceutical combination of any one of Embodiments 47-67, wherein administering the combination reduces tumor volume and/or increases survival of the patient, as compared to a non-intravenously administered combination of (a) or an administration of (b) alone.

Embodiment 85 is use of the pharmaceutical combination of any one of Embodiments 47-67 in a method of reducing tumor volume and/or increasing survival of a cancer patient.

Embodiment 86 is use of the pharmaceutical combination of any one of Embodiments 47-67 in the preparation of a pharmaceutical or medicament for reducing tumor volume and/or increasing survival of a cancer patient.

Embodiment 87 is a method of reducing tumor size and/or increasing survival in a cancer patient, the method comprising: (a) intravenously administering to the cancer patient a recombinant modified vaccinia virus Ankara (MVA) comprising a first nucleic acid encoding a first heterologous tumor-associated antigen (TAA) that when administered intravenously induces both an enhanced innate immune response and an enhanced T cell response as compared to an innate immune response and a T cell response induced by a non-intravenous administration of a recombinant MVA comprising a first nucleic acid encoding a first heterologous cancer-associated antigen; and (b) administering to the cancer patient an antibody, wherein the antibody comprises an Fc domain and is specific to an antigen that is expressed on the cell membrane of a tumor cell; wherein administration of (a) and (b) to the cancer patient reduces tumor size in the cancer patient and/or increases the survival rate of the cancer patient as compared to a non-intravenous administration of a) or an administration of b) alone.

Embodiment 88 is the method of Embodiment 87, wherein the enhanced innate immune response comprises at least one of an enhanced NK cell response, an enhanced macrophage response, an enhanced monocyte response, an enhanced neutrophil response, an enhanced basophil response, an enhanced eosinophil response, an enhanced mast cell response, and an enhanced dendritic cell response.

Embodiment 89 is the method of any one of Embodiments 87-88, wherein the recombinant MVA further encodes CD40L.

Embodiment 90 is the method of any one of Embodiments 88-89, wherein inducing an enhanced NK cell response comprises at least one of (a) inducing an enhanced ADCC response and (b) inducing NK cells to target and kill tumor cells having low MHC expression.

Embodiment 91 is the method of any one of Embodiments 87-90, wherein the recombinant MVA is administered at the same time or after the antibody.

Embodiment 92 is the method of any one of Embodiments 87-91, wherein the recombinant MVA is administered after the antibody.

Embodiment 93 is the method of any one of Embodiments 87-92, wherein the MVA comprises a first and/or second nucleic acid encoding a first and/or second heterologous TAA from any one of Embodiments 51-63.

Embodiment 94 is the method of any one of Embodiments 87-93, wherein the antibody comprises an antibody from any one of Embodiments 64-66.

Embodiment 95 is a pharmaceutical combination for reducing tumor size and/or increasing survival in a cancer patient, the combination comprising: (a) a recombinant modified vaccinia virus Ankara (MVA) comprising a first nucleic acid encoding a first heterologous tumor-associated antigen (TAA) that when administered intravenously induces both an enhanced innate immune response and an enhanced T cell response as compared to an innate immune response and a T cell response induced by a non-intravenous administration of a recombinant MVA virus comprising a nucleic acid encoding a heterologous TAA; and (b) an antibody, wherein the antibody comprises an Fc domain and is specific to an antigen that is expressed on the cell membrane of a tumor cell; wherein administration of (a) and (b) to the cancer patient reduces tumor size and/or increases the survival rate of the cancer patient as compared to an non-IV administration of a) or an administration of b) alone.

Embodiment 96 is the pharmaceutical combination of Embodiment 95, wherein the recombinant MVA further encodes CD40L.

Embodiment 97 is the pharmaceutical combination of any one of Embodiments 95-96, wherein the enhanced innate immune response comprises at least one of an enhanced NK cell response, an enhanced macrophage response, an enhanced neutrophil response, an esophil response, an enhanced eosinophil response, an enhanced mast cell response, and an enhanced dendritic cell response.

Embodiment 98 is the pharmaceutical combination of any one of Embodiments 95-97, wherein inducing an enhanced NK cell response comprises at least one of (a) inducing an enhanced ADCC response and (b) inducing NK cells to target and kill tumor cells having low MHC expression.

Embodiment 99 is the pharmaceutical combination of any one of Embodiments 95-98, wherein the MVA comprises a first and/or second nucleic acid encoding a first and/or second heterologous TAA from any one of Embodiments 51-63.

Embodiment 100 is the pharmaceutical combination of any one of Embodiments 95-99, wherein the antibody comprises an antibody from any one of
Embodiments 64-66.

Embodiment 101 is a pharmaceutical combination for reducing tumor size and/or increasing survival in a cancer patient, the combination comprising: (a) a recombinant poxvirus comprising a first nucleic acid encoding a first heterologous tumor-associated antigen (TAA) that when administered intravenously induces both an enhanced Natural Killer (NK) cell response and an enhanced T cell response as compared to an NK cell response and a T cell response induced by a non-intravenous administration of a recombinant poxvirus comprising a nucleic acid encoding a heterologous TAA; and (b) an antibody, wherein the antibody comprises an Fc domain and is specific to an antigen that is expressed on the cell membrane of a tumor cell; wherein administration of (a) and (b) to the cancer patient reduces tumor size and/or increases the survival rate of the cancer patient as compared to an non-IV administration of (a) or an administration of (b) alone.

Embodiment 102 is the pharmaceutical combination of Embodiment 101, wherein the recombinant poxvirus further encodes CD40L.

Embodiment 103 is the pharmaceutical combination of any one of Embodiments 101-102, wherein the MVA comprises a first and/or second nucleic acid encoding a first and/or second heterologous TAA from any one of Embodiments 51-63.

Embodiment 104 is the pharmaceutical combination of any one of Embodiments 101-103, wherein the antibody comprises an antibody from any one of Embodiments 64-66.

Embodiment 105 is a method of reducing tumor size and/or increasing survival in a cancer patient, the method comprising: (a) intravenously administering to the cancer patient a recombinant modified Vaccinia Ankara (MVA) comprising a first nucleic acid encoding a first heterologous tumor-associated antigen (TAA) that when administered intravenously induces both an enhanced Natural Killer (NK) cell response and an enhanced T cell response as compared to an NK cell response and a T cell response induced by a non-intravenous administration of a recombinant MVA virus comprising a nucleic acid encoding a heterologous tumor-associated antigen; and (b) administering to the cancer patient an antibody, wherein the antibody is specific to an antigen that is expressed on the cell membrane of a tumor cell; wherein administration of (a) and (b) to the cancer patient reduces tumor size in the cancer patient and/or increases the survival rate of the cancer patient as compared to an non-intravenous administration of (a) or an administration of (b) alone.

Embodiment 106 is a pharmaceutical combination for reducing tumor size and/or increasing survival in a cancer patient, the combination comprising: (a) an antibody, wherein the antibody comprises an Fc domain and is specific to an antigen that is expressed on the cell membrane of a tumor cell that when administered to the patient induces ADCC in the patient; and (b) a recombinant modified Vaccinia Ankara (MVA) virus comprising a first nucleic acid encoding a first heterologous tumor-associated antigen (TAA), wherein the MVA when administered intravenously to the patient induces an enhanced Natural Killer (NK) cell response that enhances the ADCC in the patient and enhances NK cell mediated toxicity, and wherein the MVA induces an enhanced T cell response; as compared to an NK cell response and a T cell response induced by a non-intravenous administration of a recombinant MVA virus comprising a nucleic acid encoding a heterologous tumor-associated antigen; and wherein administration of (a) and (b) to the cancer patient reduces tumor size and/or increases the survival rate of the cancer patient as compared to an non-IV administration of (a) or an administration of (b) alone.

Embodiment 107 is the pharmaceutical combination of Embodiment 106, wherein the recombinant MVA further comprises a nucleic acid encoding CD40L.

Embodiment 108 is the pharmaceutical combination of any one of Embodiments 106-107, wherein the MVA comprises a first and/or second nucleic acid encoding a first and/or second heterologous TAA from any one of Embodiments 51-63.

Embodiment 109 is a method for reducing tumor volume and/or increasing survival in a cancer patient comprising administering the pharmaceutical combination of any one of Embodiments 106-108.

Embodiment 110 is a pharmaceutical combination for use in reducing tumor volume and/or increasing survival of a cancer patient, the pharmaceutical combination comprising the pharmaceutical combination of any one of Embodiments 106-108, wherein administering the combination reduces tumor volume and/or increase survival of the patient, as compared to compared to an administration of a) or a non-intravenous administration of b) alone.

Embodiment 111 is use of the pharmaceutical combination of any one of Embodiments 106-108 in a method of reducing tumor volume and/or increasing survival of a cancer patient.

Embodiment 112 is use of the pharmaceutical combination of any one of Embodiments 106-108 for the preparation of a pharmaceutical or medicament for reducing tumor volume and/or increasing survival of a cancer patient.

Embodiment 113 is a method for increasing the effectiveness of antibody therapy in a cancer patient, the method comprising administering the pharmaceutical combination of any one of Embodiments 47-67, and 106-108, wherein administering the combination to the patient decreases the antibody concentration needed for NK cell-mediated toxicity in tumor cells.

Embodiment 114 is the pharmaceutical combination of any one of Embodiments 47-67 and 106-108, wherein the recombinant MVA comprises a nucleic acid encoding CD40L, the CD40L comprising SEQ ID NO:11.

Embodiment 115 is the pharmaceutical combination of Embodiment 114, wherein the nucleic acid encoding CD40L is a nucleic acid having at least 95%, 98%, 99%, or 100% sequence identity to SEQ ID NO:12.

Embodiment 116 is the method of any one of Embodiments 1-46, wherein the recombinant MVA comprises a nucleic acid encoding CD40L, the CD40L comprising SEQ ID NO:11.

Embodiment 117 is the method of Embodiment 116, wherein the nucleic acid encoding CD40L is a nucleic acid having at least 95%, 98%, 99%, or 100% sequence identity to SEQ ID NO:12.

Embodiment 118 is the method of Embodiment 83, wherein the Breast Cancer is a HER2 overexpressing breast cancer.

Embodiment 119 is a method of any one of embodiments 18-19, wherein the one or more amino acids of HER2 are mutated to prevent extracellular dimerization, tyrosine kinase activity, and/or phosphorylation of the HER2 polypeptide and/or antigen once expressed by the recombinant MVA.

Embodiment 120 is a method of any one of embodiments 18-19, wherein the HER antigen comprises one or more mutations for preventing the HER2 antibody from binding the HER2 antigen expressed by the recombinant MVA.

Embodiment 121 is a pharmaceutical combination for use of any one of embodiments 50-63, wherein the first and/or second TAA comprises one or more mutations to prevent binding of the antibody to the first and/or second TAA.

Embodiment 122 is the method of any one of Embodiments 18-20, wherein one or more mutations have been made to at least one of 3 loops in a juxtamembrane region of HER2.

Embodiment 123 is the method of any one of 18-21, wherein the 3 loops of the juxtamembrane region of HER2 is selected from amino acids 579-583 (loop1), 592-595 (loop2), and 615-625 (loop3).

Embodiment 124 is the method of any one of Embodiments 18-22, wherein the HER2 antigen comprises at least one mutation in at least one of amino acids E580A, F595A, K615A, H267A, F279A, V308A, S310A, L317A, H318A, K333A, P337A.

Embodiment 125 is the method of any one of Embodiments 18-23, wherein the HER2 antigen comprises at least one mutation selected from the group consisting of: E580A, F595A, K615A, H267A, F279A, V308A, S310A, L317A, H318A, K333A, P337A, D277R, E280K, K753M, and Y1023A.

Embodiment 126 is a pharmaceutical combination for use in therapy by reducing tumor volume and/or increasing survival of a cancer patient (preferably wherein the cancer patient is suffering from and/or is diagnosed with a cancer selected from the group consisting of: breast cancer, lung cancer, head and neck cancer, thyroid, melanoma, gastric cancer, bladder cancer, kidney cancer, liver cancer, melanoma, pancreatic cancer, prostate cancer, ovarian cancer, or colorectal cancer), the pharmaceutical combination comprising the pharmaceutical combination of any one of Embodiments 47-67, wherein administering the combination reduces tumor volume and/or increases survival of the patient, as compared to an non-intravenously administered combination of (a) or an administration of (b) alone.

Embodiment 127 is use of the pharmaceutical combination of any one of Embodiments 47-67 in the preparation of a pharmaceutical or medicament for reducing tumor volume and/or increasing survival of a cancer patient, preferably wherein the cancer patient is suffering from and/or is diagnosed with a cancer selected from the group consisting of: breast cancer, lung cancer, head and neck cancer, thyroid, melanoma, gastric cancer, bladder cancer, kidney cancer, liver cancer, melanoma, pancreatic cancer, prostate cancer, ovarian cancer, or colorectal cancer.

Embodiment 128 is the method of any one of Embodiments 18-27, wherein the first nucleic acid encodes a HER2 antigen having at least 90%, 95%, 97% 98%, or 99% identity to SEQ ID NO: 13.

Embodiment 129 is the method of any one of Embodiments 18-28, wherein the first nucleic acid encodes a HER2 antigen comprising SEQ ID NO: 13.

Embodiment 130 is the method of any one of Embodiments 18-29, wherein the first nucleic acid encodes a HER2 antigen, the first nucleic acid having at least 90%, 95%, 97% 98%, or 99% identity to SEQ ID NO: 14.

Embodiment 131 is the method of any one of Embodiments 18-30, wherein the first nucleic acid comprises SEQ ID NO: 14.

Embodiment 132 is the method of any one of Embodiments 18-27, wherein the first nucleic acid encodes a HER2 antigen having at least 90%, 95%, 97% 98%, or 99% identity to the full length of SEQ ID NO: 13.

Embodiment 133 is the method of any one of Embodiments 18-29, wherein the first nucleic acid encodes a HER2 antigen, the first nucleic acid having at least 90%, 95%, 97% 98%, or 99% identity to the full length of SEQ ID NO: 14.

Embodiment 134 is the method of any one of Embodiments 18-27, wherein the first nucleic acid encodes a HER2 antigen having at least 90%, 95%, 97% 98%, or 99% identity to the full length of SEQ ID NO: 1.

Embodiment 135 is the method of any one of Embodiments 18-29, wherein the first nucleic acid encodes a HER2 antigen, the first nucleic acid having at least 90%, 95%, 97% 98%, or 99% identity to the full length of SEQ ID NO: 2.

Embodiment 136 is the method of any one of Embodiments 34-36, wherein the first nucleic acid encodes a HER2 antigen having at least 90%, 95%, 97% 98%, or 99% identity to the full length of SEQ ID NO: 3.

Embodiment 137 is the method of any one of Embodiments 18-29, wherein the first nucleic acid encodes a HER2 antigen, the first nucleic acid having at least 90%, 95%, 97% 98%, or 99% identity to the full length of SEQ ID NO: 4.

EXAMPLES

The following examples illustrate the invention but should not be construed as in any way limiting the scope of the claims.

Example 1: Intravenous Administration of Recombinant MVA Results in Stronger Activation of NK Cells C57BL/6 mice were immunized subcutaneously (SC) or intravenously (IV) with $5 \times 10^7$ TCID$_{50}$ MVA-OVA (shown as rMVA) or MVA-OVA-CD40L (shown as rMVA-CD40L). PBS was injected SC. One day later, NK Cell frequencies and protein expression (shown as Geometric Mean Fluorescence Intensity (GMFI)) were assessed using flow cytometry in the spleen (shown in FIGS. 1A-1G), in the liver shown in (FIGS. 2A-2G), and in the lung shown in FIGS. 3A-3G) by staining for (A) NKp46$^+$CD3$^-$ cells; (B) CD69; (C) NKG2D; (D) FasL; (E); Bcl-X$_L$; (F), CD70; and (G) IFN-γ.

Additionally, C57BL/6 mice were immunized subcutaneously (SC) or intravenously (IV) with $5\times10^7$ TCID$_{50}$ of a recombinant MVA encoding HER2, TWIST, and CD40L antigens (shown as MVA-HER2-TWIST-CD40L). PBS was injected SC. One day later, NK Cell frequencies and protein expression (shown as Geometric Mean Fluorescence Intensity (GMFI)) were assessed using flow cytometry in the spleen (shown FIGS. 4A-4F), in the liver (shown in FIGS. 5A-5F), and in the lung (shown in FIGS. 6A-6F) by staining for (A) NKp46$^+$CD3$^-$ cells; (B) CD69; (C) FasL; (D); Bcl-X$_L$; (E), CD70; and (F) IFN-γ.

Shown in the Figures, splenic NK cell frequencies dropped or were maintained after rMVA, rMVA-CD40L, and MVA-HER2-TWIST-CD40L injection regardless of the application route. In (A) IV rMVA application increased NK cell frequencies in liver and lung as compared to SC application. In (B) CD69 is a stimulatory receptor for NK cells (Borrego et al. (1999) *Immunology* 97: 159-65) and is strongly upregulated after IV but not SC injection of rMVA, rMVA-CD40L, and MVA-HER2-TWIST-CD40L. The highest CD69 expression was induced by rMVA-CD40L IV application. In FIGS. 1(C)-3(C) the activating C-type lectin-like receptor NKG2D is upregulated on NK cells after rMVA and rMVA-CD40L immunization as compared to PBS treatment. In FIGS. 1(D)-3(D) and FIGS. 4(C)-6(C) the apoptosis-inducing factor FasL (CD95L) is upregulated on NK cells after rMVA and rMVA-CD40L immunization as compared to PBS treatment. In FIGS. 1-3(D) and FIGS. 4-6(C) spleen and lung, FasL expression was highest after IV rMVA-CD40L and MVA-HER2-TWIST-CD40L injection. In FIGS. 1-3(E) and 4-6(D) IV rMVA-CD40L and MVA-HER2-TWIST-CD40L immunization also lead to a higher expression of the anti-apoptotic Bcl family member Bcl-x$_L$ as compared to SC immunization. In FIGS. 1-3(F) and 4-6(E) upregulation of the co-stimulatory molecule CD70, a member of the tumor necrosis factor (TNF) superfamily, is induced by IV injection of rMVA, rMVA-CD40L, and MVA-HER2-TWIST-CD40L, especially on splenic NK cells. In FIGS. 1-3(G) and 4-6(F) importantly, the effector cytokine IFN-γ is most strongly expressed after IV rMVA-CD40L or IV MVA-HER2-TWIST-CD40L immunization in spleen, lung and liver. These data show that IV immunization with either rMVA-CD40L or MVA-HER2-TWIST-CD40L but not SC immunization leads to a strong, systemic NK cell activation.

Example 2: Intravenous Administration of Recombinant MVA-CD40L Results in Stronger Systemic Activation of NK Cells C57BL/6 mice were immunized IV with $5\times10^7$ TCID$_{50}$ MVA-OVA (rMVA), MVA-OVA-CD40L (rMVA-CD40L), or PBS. Six hours after injection, serum cytokine levels (A) IFN-γ, (B) IL-12p70, and (C) CD69$^+$ granzyme B$^+$ were quantified by a bead assay (Luminex) (A and B) and flow cytometry (C), as shown in FIGS. 7A-7F. The NK cell activating cytokine IL-12p70 was only detectable after rMVA-CD40L immunization. The concentration of IFN-γ was higher after rMVA-CD40L as compared to rMVA immunization. The increased serum levels of IFN-γ are in line with higher GMFI IFN-γ of NK cells (compared to FIG. 1G) and higher frequencies of spleen CD69$^+$ Granzyme B$^+$ NK cells 48 hours after rMVA-CD40L immunization.

Similar responses were seen in NHPs (*Macaca fascicularis*) after IV injection of MVA-MARV-GP-huCD40L, namely higher serum concentrations of IFN-γ (D) and IL-12p40/70 (E) as well as more proliferating (Ki671 NK cells (F) as compared to MVA-MARV-GP. These data demonstrate that CD40L-encoding MVA vaccines have comparable immunological properties in mice and NHPs.

Example 3: Intravenous Administration Results in Stronger NK Cell Activation and Proliferation Over Time C57BL/6 mice were immunized IV with $5\times10^7$ TCID$_{50}$ MVA-OVA (rMVA), MVA-OVA-CD40L (rMVA-CD40L), or PBS. NK cell activation and proliferation were measured for (A) CD3$^-$CD19$^-$NKp46$^+$, (B) Ki67, and (C) CD69 in the spleen, liver, and lung on day 1 and 4 after immunization. Results are shown in FIG. 8A-8C.

Shown in FIG. 8(A) Splenic NK cell frequencies (defined as CD3$^-$CD19$^-$NKp46$^+$) temporarily dropped by day 1 after rMVA and rMVA-CD40L immunization as seen in Example 1, but were increased by day 4 compared to PBS. In liver and lung both vectors induced higher NK cell frequencies already by day 1. Unexpectedly on day 4, NK cells frequencies in the liver were 2.4-times higher after rMVA and 4-times higher after rMVA-CD40L immunization compared to PBS. Similarly, NK cell frequencies in lung and blood were drastically enhanced on day 4 after immunization shown in FIG. 8A. In line with the systemic NK cell increase, more than 80% of all NK cells on day 4 after rMVA and rMVA-CD40L immunization were in proliferation, as indicated by the expression of the proliferation marker Ki67 in 8B. The peak of CD69 expression (shown as Geometric Mean Fluorescence Intensity (GMFI)) in all analyzed organs and blood was on day 1. By day 4 after immunization, CD69 expression was back at basal level (FIG. 8C).

Example 4: Intravenous Administration of Recombinant MVA Results in Stronger NK Cell Mediated Toxicity C57BL/6 mice were immunized IV with $5\times10^7$ TCID$_{50}$ MVA-OVA (rMVA), MVA-OVA-CD40L (rMVA-CD40L), or PBS. 24 hours later mice were sacrificed and splenic NK cells were purified by magnetic cells sorting and used as effectors in an effector: target killing assay. Briefly NK cells were cultured with CFSE-labelled MHC class I-deficient YAC-1 cells at the ratios shown in FIG. 9. Specific killing was assessed by quantifying unviable CFSE$^+$YAC-1 cells by flow cytometry. As a result, rMVA and rMVA-CD40L activated NK cells upon IV immunization are potent killers of MHC class I-deficient target cells.

Example 5: Intravenous Administration of Recombinant MVA Results in Enhanced ADCC Shown in FIG. 10A, C57BL/6 mice were treated IV either with 25 µg anti-CD4 (clone GK1.5), MVA-OVA (rMVA)+5 µg rat IgG2b, or 1 µg anti-CD4 or MVA-OVA (rMVA)+1 µg anti-CD4. 24 hours later mice were sacrificed and CD4 T cell (CD3$^+$CD4$^+$) depletion in the liver was analyzed by flow cytometry. 25 µg anti-CD4 was defined as 100% specific killing. In comparison to rMVA+IgG2b (defined as 0% specific killing), 1 µg anti-CD4 depleted 61% of all liver CD4 T cells. The combination of rMVA+1 µg anti-CD4 resulted in 93% CD4 T cell depletion, which is almost as efficient as 25 µg anti-CD4. Thus, combination of rMVA and depleting antibodies leads to synergistic target cell killing in vivo.

Shown in FIGS. 10B and 10C to assess ex vivo ADCC activity of NK cells, C57BL/6 (B) or Balb/c (C) mice were immunized IV either with PBS, MVA-OVA (rMVA) or MVA-OVA-CD40L (rMVA-CD40L). 24 hours later mice were sacrificed; splenic NK cells were purified by magnetic cell sorting and used as effectors in antibody-dependent effector: target killing assays. (FIG. 10B) Target B16.F10 cells were coated with mouse anti-human/mouse Trp1 mAb (clone TA99) and (FIG. 10C) Target CT26-HER2 cells were coated with mouse anti-human HER2 mAb (clone 7.16.4). Purified NK cells were added to the antibody-coated target cells at a 5:1 and 4:1 ratio, respectively. Cell death was determined by measuring release of Lactate Dehydrogenase (LDH) into the cell culture medium. In both assays, target cell lysis was stronger when NK cells were activated in vivo by rMVA or rMVA-CD40L compared to PBS. Activation by rMVA-CD40L resulted in the highest lytic activity. CT26-HER2 cells incubated with different concentrations of anti-human HER2 (0.1 to 10 µg/ml anti-HER2) were also more efficiently killed by rMVA-CD40L activated NK cells as compared to rMVA activated NK cells (shown in FIG. 10D).

Shown in FIG. 10E, ex vivo ADCC activity of NK cells was analyzed using MVA-HER2-Twist-CD40L. Balb/c mice were immunized IV either with PBS or MVA-HER2-Twist-CD40L. CT26-HER2 cells were coated with 5, 0.5, and 0.05 µg/ml of mouse anti-human HER2 mAb (clone 7.16.4). Purified NK cells were added to the antibody-coated target cells at a 5:1 ratio. Cell death was determined by measuring release of Lactate Dehydrogenase (LDH) into the cell culture medium. Target cell lysis was stronger when NK cells were activated in vivo by MVA-HER2-Twist-CD40L compared to PBS.

Thus, ADCC-mediated killing of tumor cells expressing relevant human tumor antigens can be enhanced by rMVA and especially rMVA-CD40L and MVA-HER2-Twist-CD40L mediated NK cell activation. Furthermore, rMVA and especially rMVA-CD40L and MVA-HER2-Twist-CD40L enhanced ADCC activity is observed over a wide dose range of antibody.

Example 6: Intravenous Administration of Recombinant MVA Induces Strong CD8 T Cell Responses C57BL/6 mice were immunized IV or SC with $5\times10^7$ TCID$_{50}$ MVA-OVA on days 0 and 16. On days 7 and 22, OVA-specific CD8 T cell responses in the blood were assessed by flow cytometry after staining with H-2K$^b$/OVA$_{257\text{-}264}$ dextramers. Shown in FIG. 11, on day 7 the frequency of OVA-specific CD8 T-cells was 9-fold higher as compared to SC injections. On day 22, OVA-specific T-cells were 4-fold higher than after SC injection.

Example 7: Intravenous Administration of Recombinant MVA-CD40L Further Enhances CD8 T Cell Responses Shown in FIG. 12, C57BL/6 mice were immunized intravenously with $5\times10^7$ TCID$_{50}$MVA-OVA or MVA-OVA-CD40L on days 0 and 35. OVA-specific CD8 T cell responses in the blood were assessed by flow cytometry after staining with H-2Kb/OVA$_{257\text{-}264}$ dextramers. At the peak of the primary (day 7) and secondary (day 39) response, the frequency of OVA-specific CD8 T cells was enhanced 4-fold and 2-fold, respectively after MVA-OVA-CD40L compared to MVA-OVA immunization (Lauterbach et al. 2013).

Example Prime-Boost Immunization Shows Repeated NK Cell Activation and Proliferation

TABLE 1

Examples 8-10 IV immunization scheme

| groups | prime day 0 | boost day 21 | boost day 42 |
|---|---|---|---|
| PBS | PBS | PBS | PBS |
| rMVA hom | rMVA | rMVA | rMVA |
| rMVA-CD40L hom | rMVA-CD40L | rMVA-CD40L | rMVA-D40L |
| rMVA-CD40L het | rMVA-CD40L | rMVA | rMVA |

C57BL/6 mice were immunized IV as shown in Table 1 (recombinant MVA dosages were at $5\times10^7$ TCID$_{50}$). NK cells (CD3$^-$NKp46$^+$) were analyzed in the blood by flow cytometry one and four days after second and third immunization. Shown in FIGS. 13A and 13B are the GMFI CD69 (A) and the frequency of Ki67+NK cells (B). FIGS. 13A and 13B illustrate that NK cells are activated by each immunization despite the presence of anti-vector immunity. This unexpected finding supports combination of antibody therapy with boost immunizations that would activate NK cells. Thus, when cancer patients are treated multiple times with recombinant MVA and mount anti-vector responses, NK cell activation is not impaired. In contrast, each treatment leads to de novo NK cell activation.

Example 9: Prime-Boost Immunization Shows Stronger Induction of CD4 T Helper Cells C57BL/6 mice were immunized as shown in Table 1 (recombinant MVA dosages were at $5\times10^7$ TCID$_{50}$). Serum cytokine levels were quantified at 6 hours post immunization by a multiplex bead assay (Luminex). Shown are the results from the expression of the named cytokines. FIG. 14A) IL-6; 14B) CXCL10; 14C) IFN-α; 14D) IL-22; 14E) IFN-γ; 14F) CXCL1; 140) CCL4; 14H) CCL7; 141) CCL2; 14J) CCL5; 14K) TNF-α; 14L) IL-12p70; and 14M) Th-18.

Shown in FIGS. 14A-14M, rMVA-CD40L hom-treated mice had a similar cytokine profile as mice primed with rMVA and boosted with rMVA-CD40L (rMVA-CD40L het). rMVA hem-treated mice displayed lower levels of IL-6, 1L12p70, IL-22, IFN-α, TNF-α, CCL2, CCL5 and CXCL1 after the first and second immunization compared to mice primed with rMVA-CD40L. A cytokine absent after the prime but highly produced after second and third immunization was IL-22. IL-22 is largely produced by effector T helper cells and subpopulations of innate lymphocyte cells. The higher expression of IL-22 in rMVA-CD40L het or rMVA-CD40L hom-treated mice thus indicates stronger induction CD4 T helper responses by rMVA-CD40L immunization. Overall, IV rMVA and rMVA-CD40L immunization induced high systemic cytokine responses that are highest in mice primed with rMVA-CD40L.

Example 10: Prime-Boost Immunization Shows Stronger Antigen Specific CD8 T Cell Responses C57BL/6 mice were immunized IV as shown in Table 1 (recombinant MVA dosages were at $5\times10^7$ TCID$_{50}$). Similar to NK cells, induction of antigen-specific CD8 T cell responses after repetitive immunization was assessed. Shown in FIG. 15A-15D, CD8 T cell frequencies were drastically enhanced after the second and third immunization with rMVA and rMVA-CD40L. Of note, after the second immunization, about 80% of all PBL were CD8 T cells (FIG. 15A). While the vector-specific (B8) CD8 T cell response peaked after the second immunization (FIG. 15B), transgene-specific (OVA) responses could be further boosted with a third immunization (FIG. 15C). This resulted in increased ratios of OVA/B8-specific CD8 T cells (FIG. 15D), indicating an immune focusing towards the transgene. Importantly, these results demonstrate that antigen-specific T cell responses can be boosted by IV immunization in the presence of anti-vector immunity. Thus, in cancer patients, multiple treatments might result in stronger tumor-antigen specific CD8 T cell responses.

Example 11: Prime-Boost Immunization Shows Stronger Memory CD8 and CD4 T Cell Responses C57BL/6 mice were immunized IV as shown in Table 1. The results are shown in FIG. 16A-16B. Phenotypically, effector and effector memory T cells can be identified by the expression of CD44 and the lack of surface CD62L. Monitoring CD44$^+$CD62L$^-$CD8 (FIG. 16A) and CD4 (FIG. 16B) T cells in the blood demonstrated that repeated IV immunization induces expansion of effector and effector memory T cells. Interestingly, mice that received either rMVA-CD40L hom or rMVA-CD40L het had about 2.5-fold more circulating effector CD4 T cells than mice primed with rMVA (B, day 25). This indicates that systemic priming with rMVA-CD40L induces stronger CD4 T cell responses than rMVA.

Figure 17:
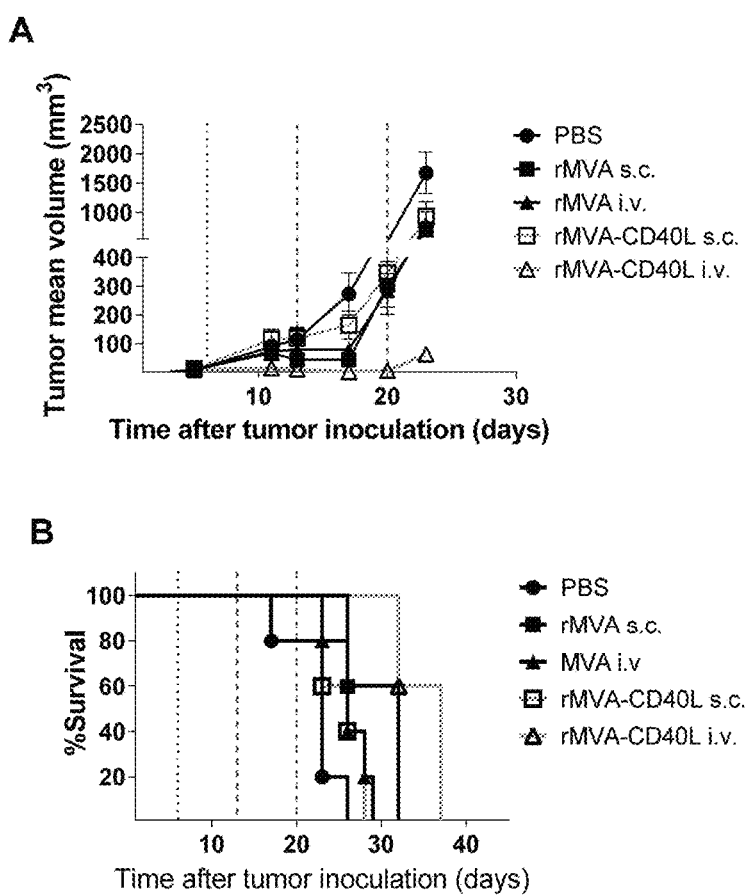
FIGS. 17A-17B show superior anti-tumor effect of IV rMVA-CD40L immunization in a heterologous prime boost scheme in a melanoma model. C57BL/6 mice bearing palpable B16.OVA tumors were primed (dotted line) either with PBS, MVA-OVA (rMVA) or MVA-OVA-CD40L (rMVA-CD40L) SC or IV as described in Example 12. Mice received subsequent boosts with FPV-OVA 7 and 14 days after prime (dashed lines). Tumor growth was measured at regular intervals. Shown are tumor mean volume (FIG. 17A) and survival of tumor-bearing mice (FIG. 17B) by day 45 after tumor inoculation.

Example 12: Intravenous Administration of Recombinant MVA Results in Strong Anti-Tumor Effects in Treating Melanoma C57BL/6 mice bearing palpable B16.OVA tumors were primed (dotted line) either IV or SC with PBS, MVA-OVA (rMVA) or MVA-OVA-CD40L (rMVA-CD40L) (recombinant MVA dosages were at 5×10$^7$ TCID$_{50}$). At 7 and 14 days after prime immunization, the mice received subsequent boosts with FPV-OVA at 5×10$^7$ TCID$_{50}$ (dashed lines). Tumor growth was measured at regular intervals. Shown in FIG. 17 are tumor mean volume (FIG. 17A) and survival of tumor-bearing mice by day 45 after tumor inoculation (FIG. 17B). Thus, priming of B16.OVA tumor bearing mice IV with rMVA-CD40L provides a stronger anti-tumor effect as compared to both SC rMVA-CD40L or SC or IV rMVA.

Figure 18:
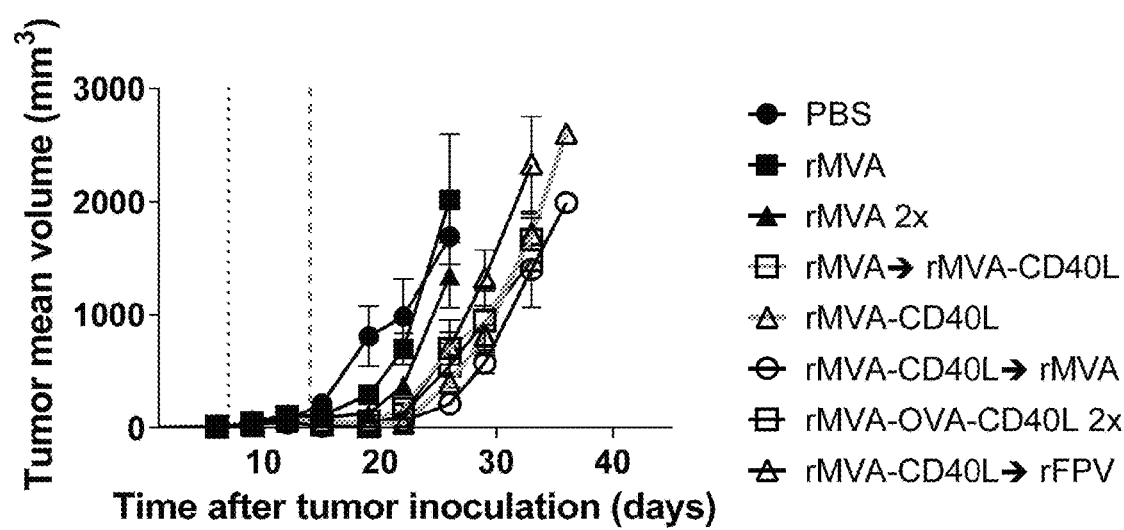
FIG. 18 shows efficient tumor control after a single IV immunization with MVA-OVA-CD40L (rMVA-CD40L). C57BL/6 mice bearing palpable B16.OVA tumors were primed IV or received IV prime and boost as described in Example 13. Tumor growth was measured at regular intervals. Shown is the tumor mean volume.

Example 13: A Single Intravenous Administration of Recombinant MVA Results in Strong Anti-Tumor Effects C57BL/6 mice bearing palpable B16.OVA tumors were IV vaccinated as shown in Table 2. Tumor growth was measured at regular intervals. Shown in FIG. 18 is tumor mean volume. The results indicate that a single therapeutic immunization with rMVA-CD40L is as strong as homologous or heterologous prime/boost immunizations. Importantly, these data highlight the potent anti-tumor activity of rMVA-CD40L.

TABLE 2

Vaccination scheme corresponding to Example 13

| Group | Day 8 Prime | Day 15 Boost |
| --- | --- | --- |
| PBS | PBS | none |
| rMVA | rMVA | none |
| rMVA 2x | rMVA | rMVA |
| rMVA→MVA-CD40L | rMVA | rMVA-CD40L |
| rMVA→CD40L | rMVA-CD40L | none |
| rMVA-CD40L→rMVA | rMVA-CD40L | rMVA |
| rMVA-CD40L 2x | rMVA-CD40L | rMVA-CD40L |
| rMVA-CD40L→rFPV | rMVA-CD40L | rFPV |

Example 14: CD8 T-Cells are Important for rMVA-CD40L Mediated Tumor Control

Figure 19:
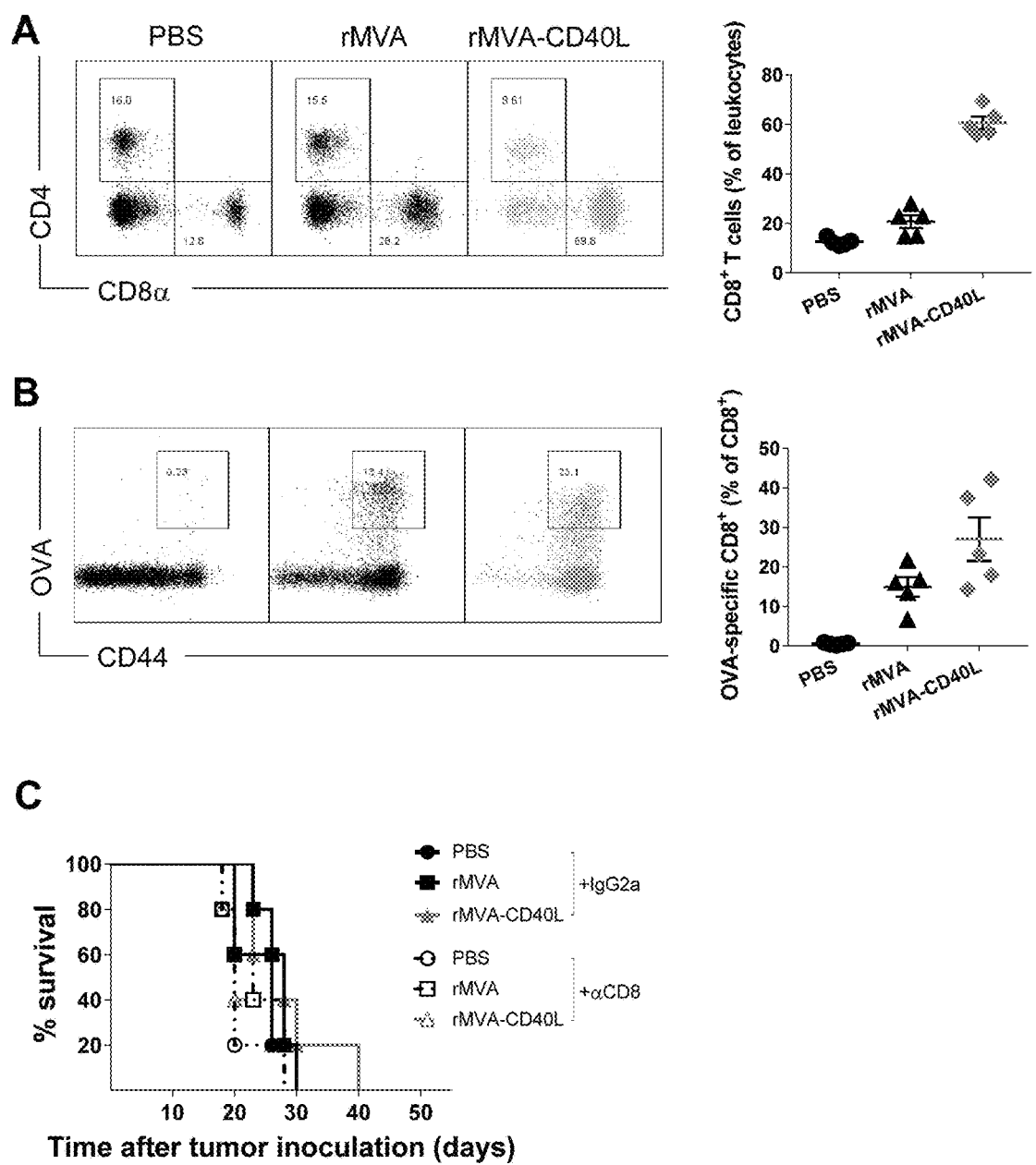
FIGS. 19A-19C show that CD8 T cells are essential players in rMVA-CD40L mediated tumor control. C57BL/6 mice bearing palpable B16.OVA tumors were immunized IV either with PBS, MVA-OVA (rMVA) or MVA-OVA-CD40L (rMVA-CD40L) as described in Example 14. Where indicated, mice received 200 μg anti-CD8 antibody intraperitoneally (IP).

C57BL/6 mice bearing palpable B16.OVA tumors were immunized via intravenous administration with PBS, MVA-OVA (rMVA) or MVA-OVA-CD40L (rMVA-CD40L) (recombinant MVA dosages were at 5×10$^7$ TCID$_{50}$). Mice received intraperitoneal injections of 200 μg anti-CD8 antibody where indicated. Shown in FIG. 19, immunization with rMVA-CD40L induced stronger overall CD8 T cell responses (FIG. 19A) as well as stronger neo-antigen (OVA)-specific CD8 T cell responses (FIG. 19B) compared to rMVA. FIG. 19C) represents overall survival. These data indicate that rMVA-CD40L induces superior CD8 T cell responses in a tumor setting and that the induced CD8 T cell responses are important for the anti-tumor effect seen after therapeutic immunization.

Figure 20:
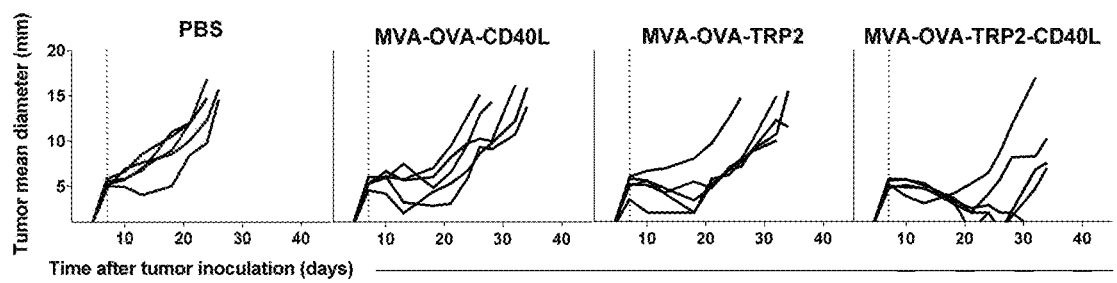
FIGS. 20A-20C show that simultaneous targeting of two TAAs is more efficient than targeting only one. C57BL/6 mice bearing palpable B16.OVA tumors were immunized IV either with PBS, MVA-OVA-CD40L, MVA-OVA-TRP2 or MVA-OVA-TRP2-CD40L as described in Example 15. Tumor growth was measured at regular intervals and is displayed as (FIG. 20A) mean diameter of individual mice.
Figure 20:
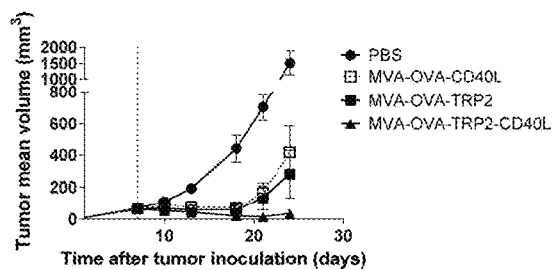
Figure 20:
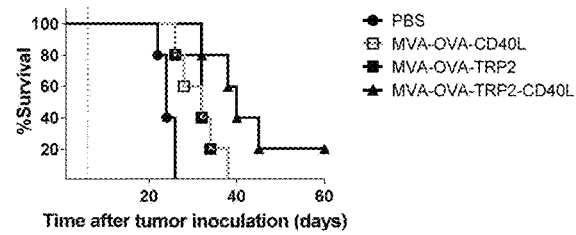

Example 15: IV Administration of Recombinant MVA Encoding at Least Two TAAs is More Effective C57BL/6 mice bearing palpable B16.OVA tumors were immunized IV either with PBS, MVA-OVA-TRP2, MVA-OVA-TRP2-CD40L or MVA-OVA-CD40L. Shown in FIG. 20, tumor growth was measured at regular intervals and is displayed as mean diameter of individual mice (FIG. 20A) and mean volume (FIG. 20B). Survival is shown in FIG. 20(C). These data indicate that a single therapeutic immunization with rMVA-CD40L encoding two TAAs is more efficient than immunization with rMVA-CD40L encoding only one TAA.

Example 16: Intravenous Administration of Recombinant MVA-CD40L Increased T-Cell Infiltration in the Tumor Microenvironment C57BL/6 mice bearing palpable B16.OVA tumors were immunized intravenously with PBS, rMVA (MVA-OVA) or rMVA-CD40L (MVA-OVA-CD40L) (recombinant MVA dosages were at 5×10$^7$ TCID$_{50}$). After 7 days, mice were sacrificed. As shown in FIGS. 21A and 21B, the frequency and distribution of CD8$^+$ T cells and OVA$_{257-264}$-specific CD8+ T cells was analyzed among leukocytes in spleen, tumor-draining lymph nodes (TDLN) and tumor tissues. In FIG. 21C, geometric mean fluorescence intensity (GMFI) of PD-1 and Lag3 on tumor-infiltrating OVA$_{257-264}$-specific CD8$^+$ T cells was analyzed; In FIG. 21D, representative dot plots of tumor-infiltrating CD8$^+$ T cells of Ki67 and PD-1 expression is shown. In FIG. 21E, frequencies of tumor-infiltrating Ki67$^+$CD8$^+$ T cells and GMFI of PD-1 are shown; in FIG. 21F, frequency of tumor-infiltrating regulatory T cells (Treg) among leukocytes is illustrated. In FIG.

21G, frequencies of PD-1$^{high}$- and PD-1$^{neg}$-tumor-infiltrating Treg are shown. Taken together, these data show that rMVA-CD40L immunization leads to a more pronounced infiltration of TAA-specific CD8 T cells into the tumor microenvironment (TME) and that these CD8 T cells express lower amounts of markers associated with 'immune exhaustion' compared to PBS and rMVA immunization. Furthermore, rMVA-CD40L immunization leads to a reduction of highly suppressive Treg in the TME compared to PBS.

Example 17: Intravenous Administration of Recombinant MVA-CD40L Increased Longevity of T-Cell Infiltration of Tumor Microenvironment TCR-transgenic OVA-specific CD8 T cells (OT-I) were intravenously transferred into B16.OVA tumor bearers when tumors were palpable. When tumors reached at least 60 mm$^3$ in volume animals were immunized with MVA-BN, MVA-OVA (rMVA), or MVA-OVA-CD40L (rMVA-CD40L) (recombinant MVA dosages were at 5×10$^7$ TCID50). After 17 days, mice were sacrificed and analyzed for (FIG. 22A) Frequency of CD8$^+$ T cells among leukocytes in tumor tissues; FIG. 22B) Frequency of Lag3$^+$PD1$^+$ within CD8$^+$ T cells and frequency of Eomes$^+$PD1$^+$ T cells within CD8$^+$ T cells; FIG. 22C) Presence of OT-I-transgenic CD8$^+$ T cells within the TME upon immunization; and FIG. 22D) Frequency of Lag3$^+$PD1$^+$ exhausted T cells within OT-1$^+$CD8$^+$ T cells; and frequency of Eomes$^+$PD1$^+$ exhausted T cells within OT-I$^+$CD8$^+$ T cells. The results are shown in FIG. 22A-22D. These data indicate that TAA-specific CD8 T cells that are recruited into the TME upon rMVA-CD40L immunization show less signs of immune exhaustion than after control treatment (MVA-BN without encoded TAA) or rMVA immunization even after prolonged exposure to the TME.

Example 18; Intravenous Administration of Recombinant MVA-CD40L Decreased Levels of Treg in Tumor Microenvironment Purified OVA-specific TCR-transgenic CD8 T cells (OT-I) were intravenously transferred into B16.OVA tumor bearers when tumors were palpable. When tumors reached at least 60 mm$^3$ in volume animals were immunized with MVA-BN, MVA-OVA (rMVA), or MVA-OVA-CD40L (rMVA-CD40L) (recombinant MVA dosages were at 5×10$^7$ TCID$_{50}$). After 17 days mice were sacrificed and analyzed for: (FIG. 23A) Frequency of Foxp3$^+$ CD4$^+$ Treg among CD4$^+$ T cells in tumor tissues; and (FIG. 23B) Ratio of CD8$^+$CD44$^+$ effector T cells to Foxp3$^+$ CD4$^+$ Tregs. The results are shown in FIG. 23A-23B. Taken together, these data show that even after prolonged exposure to the TME, a single immunization with rMVA-CD40L leads to an increased Teff/Treg ratio compared control treatment (MVA-BN without encoded TAA) or rMVA immunization.

Example 19: MVA-OVA-CD40L Safer for Humans as Compared to Agonistic CD40 mAb

TABLE 3

Immunization schedule Example 19

| groups | prime day 0 | boost day 21 | boost day 42 |
|---|---|---|---|
| PBS | PBS | PBS | PBS |
| rMVA hom | rMVA | rMVA | rMVA |
| rMVA-CD40L hom | rMVA-CD40L | rMVA-CD40L | rMVA-CD40L |
| rMVA-CD40L het | rMVA-CD40L | rMVA | rMVA |
| αCD40 | Anti-CD40 mAb | Anti-CD40 mAb | Anti-CD40 mAb |

Figure 24:
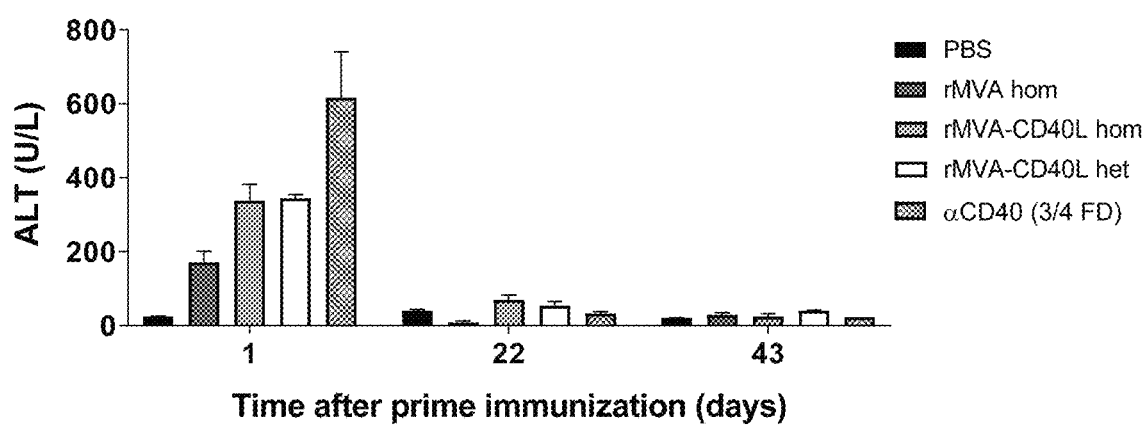
FIG. 24 shows lower serum levels of alanine aminotransferase (ALT) after rMVA and rMVA-CD40L immunization compared to anti-CD40 immunoglobulin injection. C57BL/6 mice were injected IV either with PBS, MVA-OVA (rMVA), MVA-OVA-CD40L (rMVA-CD40L) or anti-CD40 (FGK4.5) as in Example 19. Serum ALT concentration was analyzed one day after each immunization by ELISA.

C57BL/6 mice were injected IV either with PBS, MVA-OVA (rMVA), MVA-OVA-CD40L (rMVA-CD40L) or anti-CD40 (FGK4.5) as shown in Table 3 (recombinant MVA dosages were at 5×10$^7$ TCID$_{50}$, anti-CD40 dosage was at 100 μg). Serum concentration of alanine aminotransferase (ALT) was quantified one day after each immunization by ELISA. Shown in FIG. 24, ALT levels were highest after the first injection of anti-CD40. The ALT concentration after the first immunization with rMVA-CD40L was 2-fold lower than after anti-CD40 treatment. Importantly, serum ALT levels after repeated rMVA and rMVA-CD40L immunization were not enhanced. Although repeated injection of anti-CD40 antibody also did not result in enhanced ALT levels, 3 of 4 mice died in this group (FD=found dead). Also shown in FIG. 21 lower serum levels of alanine aminotransferase (ALT) were seen after rMVA and rMVA-CD40L immunization compared to anti-CD40 immunoglobulin injection. Thus, in contrast to the described liver toxicity of agonistic anti-CD40 (Medina-Echeverz et al., 2015), no such toxicity was observed after repeated IV injection of rMVA and rMVA-CD40L.

Figure 25:
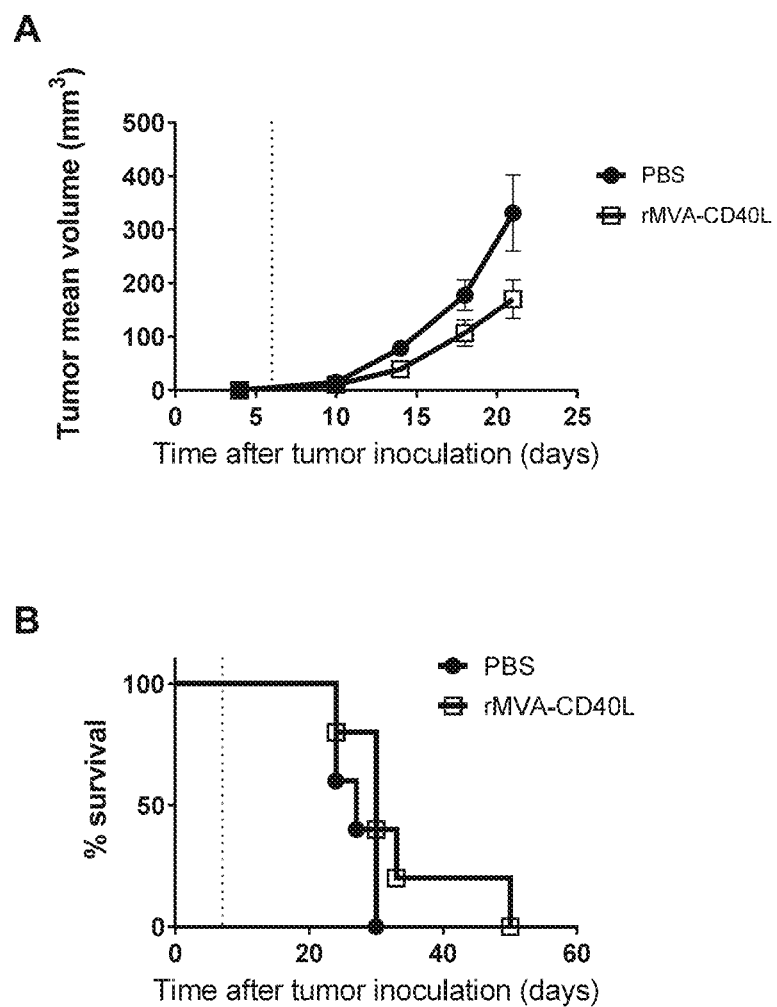
FIGS. 25A-25B show prolonged survival in a colon cancer model after IV rMVA-CD40L immunization. Balb/c mice bearing palpable CT26.HER2 tumors were immunized IV with MVA-AH1A5-p15-Trp2-CD40L (rMVA-CD40L) or received PBS as described in Example 20. Tumor growth was measured at regular intervals. Shown are the tumor mean volume (FIG. 25A) and survival (FIG. 25B).

Example 20: Increased Overall Survival and Tumor Reduction in IV Administration of rMVA-CD40L Balb/c mice bearing palpable CT26.HER2 tumors were immunized IV with MVA-AH1A5-p15-TRP2-CD40L (rMVA-CD40L) or received PBS. Tumor growth was measured at regular intervals. Shown in FIG. 25A-25B are the tumor mean volume (FIG. 25A) and survival (FIG. 25B). These data indicate that a single therapeutic immunization with rMVA-CD40L is efficiently prolonging survival in a colon cancer model.

Example 21: Increased Overall Survival and Tumor Reduction in IV Administration of rMVA-CD40L+Anti-Trp1

Figure 26:
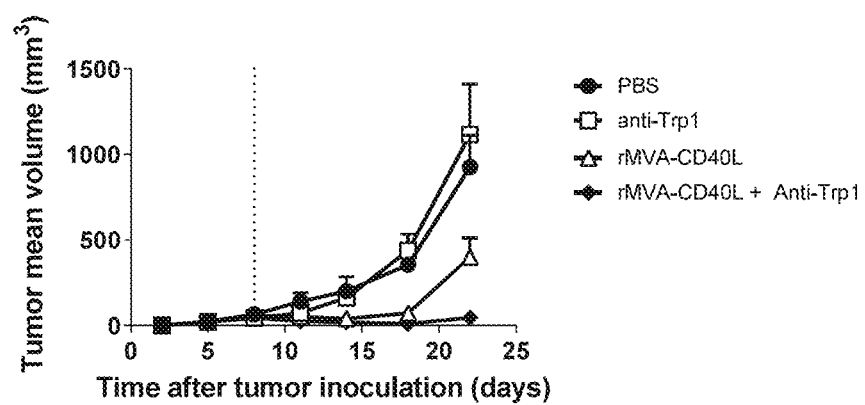
FIGS. 26A-26B show increased anti-tumor effect of rMVA-CD40L in combination with anti-Trp1. C57BL/6 mice bearing palpable B16.OVA tumors were immunized IV with MVA-OVA-CD40L (rMVA-CD40L) on day 8 as described in Example 21. Where indicated 200 μg anti-Trp1 (clone TA99) was injected IP twice/week starting on day 5. Shown is the tumor mean volume (FIG. 26A) and overall survival (FIG. 26B).
Figure 26:
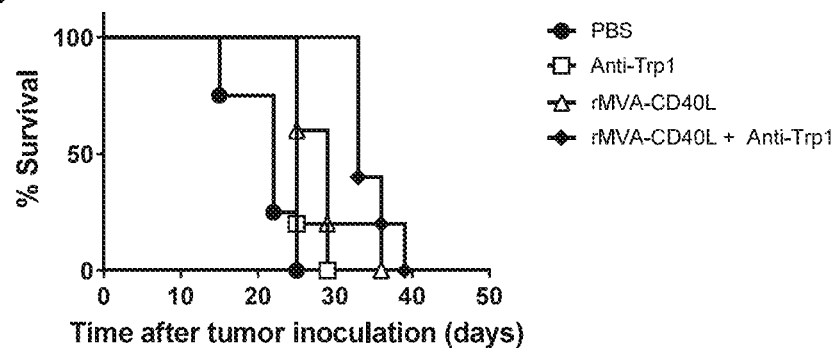
Figure 27:
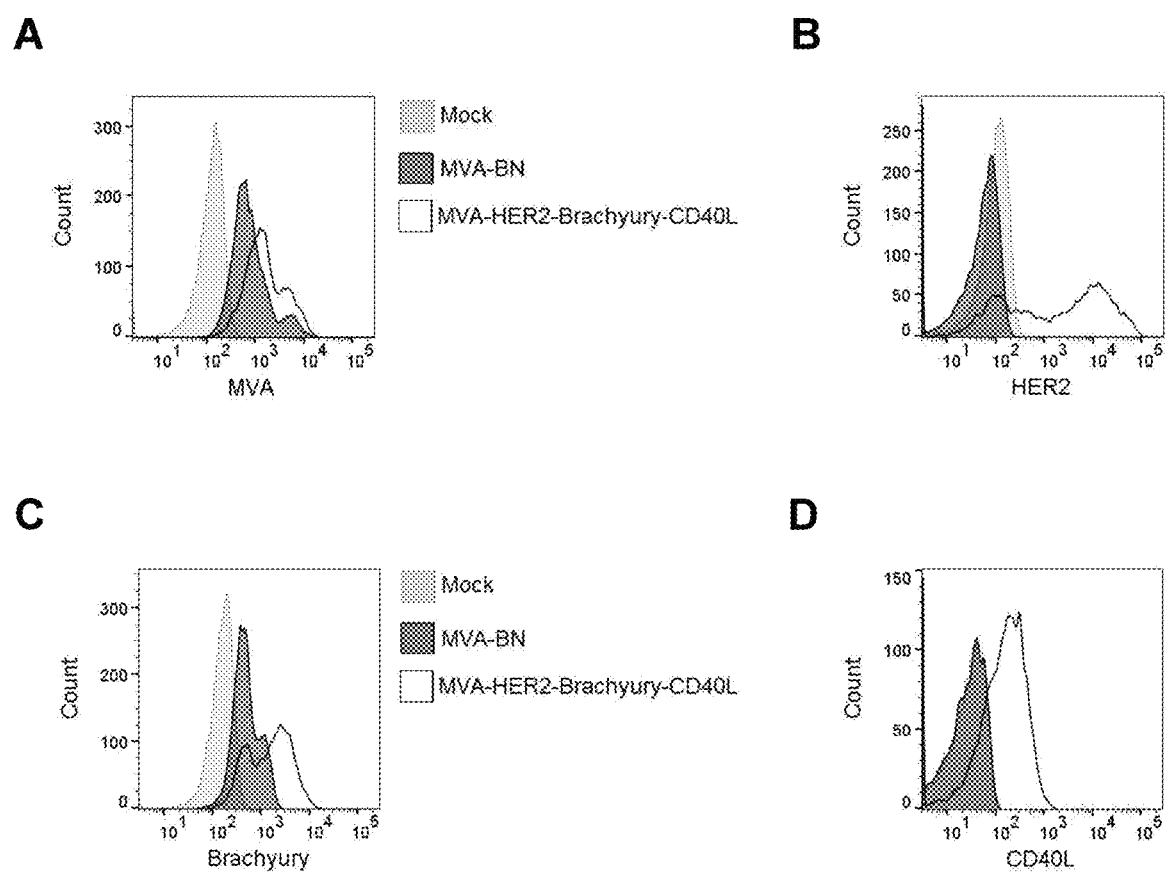
FIGS. 27A-27D show transgene expression of MVA-HER2-Brachyury-CD40L. HeLa cells were left untreated (Mock; filled grey line) or infected with MVA-BN (filled black line) or MVA-HER2-Brachyury-CD40L (open black line) as described in Example 23. Then, (FIG. 27A) MVA, (FIG. 27B) HER2, (FIG. 27C) Brachyury, and (FIG. 27D) CD40L protein expression was determined by flow cytometry (see histograms).

C57BL/6 mice bearing palpable B16.OVA tumors (at least 60 mm$^3$ in volume) were immunized intravenously with MVA-OVA-CD40L (mBNbc115) at 5×10$^7$ TCID$_{50}$ on day 8. Mice were intraperitoneally injected with 200 μg anti-Trp1 (clone TA99) twice/week starting on day 5. Results are shown in FIGS. 26A and 26B for tumor mean volume and overall survival rate, respectively. Shown in the Figures, the combination of rMVA-CD40L and the anti-Trp1 mAb showed an overall reduction in tumor volume and increase in overall survival rate as compared to the anti-Trp1 mAb and the rMVA-CD40L by themselves. Thus, combination of a tumor-specific antibody and rMVA-CD40L administered intravenously has a significantly increased anti-tumor activity as compared to either a non-IV administration of rMVA-CD40L or an administration of antibody alone.

Example 22: Construction of Recombinant MVA Viruses MVA-mBN445, MVA-mBN451, MVA-mBNbc197, MVA-mBNbc195, MVA-mBNbc388, MVA-mBN bc389, and MVA-mBN484

Generation of recombinant MVA viruses that embody elements of the combination therapy (e.g., MVA-mBN445, MVA-mBN451 and MVA-mBN484) was done by insertion of the indicated transgenes with their promoters into the vector MVA-BN. Transgenes were inserted using recombination plasmids containing the transgenes and a selection cassette, as well as sequences homologous to the targeted loci within MVA-BN. Homologous recombination between the viral genome and the recombination plasmid was achieved by transfection of the recombination plasmid into MVA-BN infected CEF cells. The selection cassette was then deleted during a second step with help of a plasmid expressing CRE-recombinase, which specifically targets loxP sites flanking the selection cassette, therefore excising the intervening sequence.

For construction of MVA-BN mBNbc197 and MVA-BN mBNbc195, recombination plasmids were used for the two or three transgenes for mBNbc197 (MVA-OVA-TRP2) and mBNbc195 (MVA-OVA-TRP2-CD40L), respectively. The plasmids included insert sequences which are also present in MVA. Nucleotide sequences encoding the OVA and TRP2 and/or CD40L antigens were present between the MVA insert sequences to allow for recombination into the MVA viral genome. Thus, a plasmid was constructed for each construct that contained the OVA and TRP2 and/or CD40L coding sequences, each downstream of a promoter.

For the construction of mBN451, the recombination plasmid included two transgenes HER2v1 and Brachyury (SEQ ID NO: 1 and SEQ ID NO: 3, respectively), each preceded by a promoter sequence, as well as sequences which are identical to the targeted insertion site within MVA-BN to allow for homologous recombination into the viral genome. The HER2 and Brachyury coding sequences (or nucleotide sequences) are SEQ ID NO: 2 and SEQ ID NO: 4, respectively.

For the construction of mBN445 the recombination plasmid included the three transgenes HER2v1, Brachyury, and CD40L (SEQ ID NO: 1, SEQ ID NO: 3, and SEQ ID NO: 11, respectively), each preceded by a promoter sequence, as well as sequences which are identical to the targeted insertion site within MVA-BN to allow for homologous recombination into the viral genome. The HER2, Brachyury, and CD40L coding sequences (or nucleotide sequences) are SEQ ID NO: 2, SEQ ID NO: 4, and SEQ ID NO: 12, respectively.

For construction of mBNbc388 the recombination plasmid included the three transgenes HER2v1, Twist, and CD40L (SEQ ID NO: 1, SEQ ID NO: 15, and SEQ ID NO: 17, respectively), each preceded by a promoter sequence, as well as sequences which are identical to the targeted insertion site within MVA-BN to allow for homologous recombination into the viral genome. The HER2v1, Twist, and CD40L coding sequences (or nucleotide sequences) are SEQ ID NO: 2, SEQ ID NO: 16, and SEQ ID NO: 18, respectively.

For construction of mBNbc389 the recombination plasmid included the two transgenes HER2v1 and Twist (SEQ ID NO: 1, SEQ ID NO: 15, respectively), each preceded by a promoter sequence, as well as sequences which are identical to the targeted insertion site within MVA-BN to allow for homologous recombination into the viral genome. The HER2, Twist, and CD40L coding sequences (or nucleotide sequences) are SEQ ID NO: 2 and SEQ ID NO: 16 respectively.

For construction of mBN484 the recombination plasmid included the three transgenes HER2 v.2, Brachyury, and CD40L (SEQ ID NO: 13, SEQ ID NO: 3, and SEQ ID NO: 11, respectively), each preceded by a promoter sequence, as well as sequences which are identical to the targeted insertion site within MVA-BN to allow for homologous recombination into the viral genome. The HER2 v.2, Twist, and CD40L coding sequences (or nucleotide sequences) are SEQ ID NO: 14, SEQ ID NO: 4, and SEQ ID NO: 12, respectively.

For generation of the above described mBN MVAs, (e.g, .mBN445, mBN451, and mBN484), CEF cell cultures were each inoculated with MVA-BN and transfected each with the corresponding recombination plasmid. In turn, samples from these cell cultures were inoculated into CEF cultures in medium containing drugs inducing selective pressure, and fluorescence-expressing viral clones were isolated by plaque purification. Loss of the fluorescent protein-containing selection cassette from these viral clones was mediated in a second step by CRE-mediated recombination involving two loxP sites flanking the selection cassette in each construct. After the second recombination step only the transgene sequences (e.g., HER2, Brachyury, and/or CD40L) with their promoters inserted in the targeted loci of MVA-BN were retained. Stocks of plaque-purified virus lacking the selection cassette were prepared.

Expression of the identified transgenes was subsequently demonstrated in cells inoculated with the described construct (See e.g., FIG. 27A-27D).

Generation of MVA-mBNbc197, mBNbc195, mBNbc388, and mBNbc389 was carried out by using a cloned version of MVA-BN in a bacterial artificial chromosome (BAC). Recombination plasmids containing the different transgenes for mBNbc197 (MVA-Ova-Trp2), mBNbc195 (MVA-Ova-Trp2-CD40L), mBNbc388 and mBNbc389 were used. The plasmids included sequences that are also present in MVA and therefore allow for specific targeting of the integration site. Nucleotide sequences encoding the OVA, Her2 v1, TwistTrp2 and/or CD40L antigens were present between the MVA sequences that allow for recombination into the MVA viral genome. Thus, a plasmid was constructed for each construct that contained the OVA, Her2 v1, Twist, Trp2 and/or CD40L coding sequences, each downstream of a promoter. Briefly, infectious viruses were reconstituted from BACs by transfecting BAC DNA into BHK-21 cells and superinfecting them with Shope fibroma virus as a helper virus. After three additional passages on CEF cell cultures, helper-virus free MVA-mBNbc197, MVA-mBNbc195, MVA-mBNbc388 and MVA-mBNbc389 were obtained. An exemplary MVA generation is also found in Baur et al. ((2010) *J. Virol.* 84: 8743-52).

Example 23: Heterologous Expression of MVA-HER2-Brachyury-CD40L

HeLa cells were left untreated (mock) or infected with MVA-BN or MVA-HER2-Brachyury-CD40L (MVA-mBN445). After overnight culture, cells were stained with anti-HER2-APC (clone 24D2), anti-Brachyury (rabbit polyclonal)+anti-rabbit IgG-PE and anti-CD40L-APC (clone TRAP1). Shown in FIG. 27A-27D, flow cytometric analysis revealed expression of all three transgenes.

Figure 28:
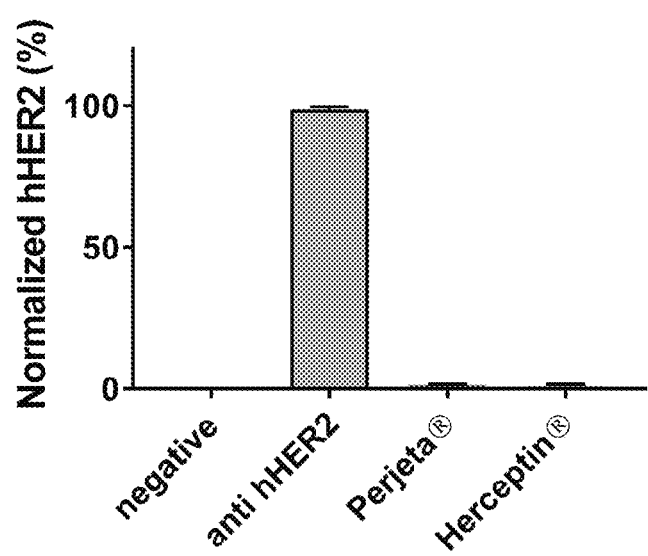
FIG. 28 shows that Herceptin® antibody (also known as trastuzumab) and Perjeta® antibody (also known as pertuzumab) anti-HER2 antibodies do not bind to the modified HER2 sequence described in Example 24. CT26 cells were infected with MVA-HER2-Brachyury-CD40L at an MOI of 1. 24 hours later, cells were incubated with 5 μg/ml of the HER2 antibodies Herceptin® antibody, Perjeta® antibody, or 24D2 and analyzed by flow cytometry.
Figure 29:
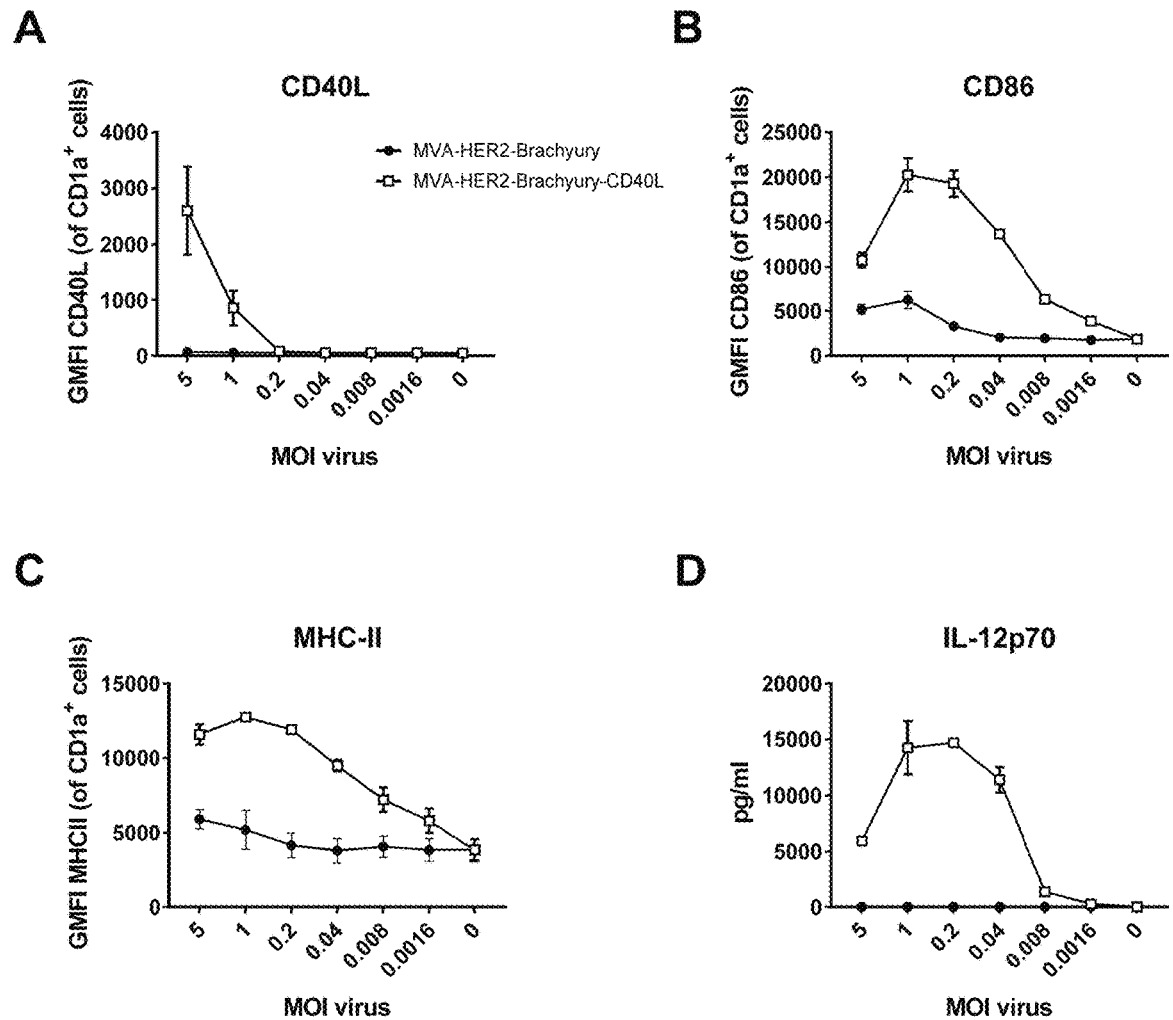
FIGS. 29A-29D show dose dependent and enhanced activation of human DCs by MVA-HER2-brachyury-CD40L as compared to MVA-HER2-brachyury. Monocyte-derived DCs were generated after enrichment of CD14$^+$ monocytes from human PBMCs and cultured for 7 days in the presence of GM-CSF and IL-4 as described in Example 25. DCs were stimulated with MVA-HER2-brachyury or MVA-HER2-brachyury-CD40L. Expression of (FIG. 29A) CD40L.

Example 24: Synthetic HER2 Proteins Prevent Binding of Trastuzumab and Pertuzumab Mouse colon carcinoma CT26 cells were infected with MVA-HER2-Brachyury-CD40L (MVA-mBN484) at an MOI of 1. 24 hours later, cells were incubated with 5 μg/ml of the HER2 antibodies Trastuzumab, Pertuzumab or 24D2. Figure shows expression levels of HER2 normalized to clone 24D2 HER2 staining. Data expressed as Mean±SEM, representative of two independent experiments. The results are shown in FIG. 28.

Example 25: Enhanced Activation of Human DCs by MVA-HER2-Brachyury-CD40L

Monocyte-derived dendritic cells (DCs) were generated after enrichment of $CD14^+$ monocytes from human PBMCs and cultured for 7 days in the presence of GM-CSF and IL-4 according to protocol (Miltenyi, MO-DC generation tool box). DCs were stimulated with MVA-HER2-Brachyury or MVA-HER2-Brachyury-CD40L. Shown in FIG. 29 expression of A) CD40L, B) CD86, and C) and MHC class II was analyzed by flow cytometry. Shown in D), the concentration of IL-12p70 in the supernatant was quantified by luminex after over-night culture.

This experiment demonstrates that rMVA-HER2-Brachyury-CD40L stimulates human DCs, inducing their activation and thus enhancing their capability to present antigens. The production of the Th1 polarizing and NK cell activating cytokine IL-12p70 by stimulated human DCs indicates that MVA-HER2-Brachyury-CD40L activates human DCs towards a pro-inflammatory phenotype.

Example 26: Increase in Overall Survival and Tumor Reduction in Intravenous Administration of mBNbc388 and mBNbc389

Figure 30:
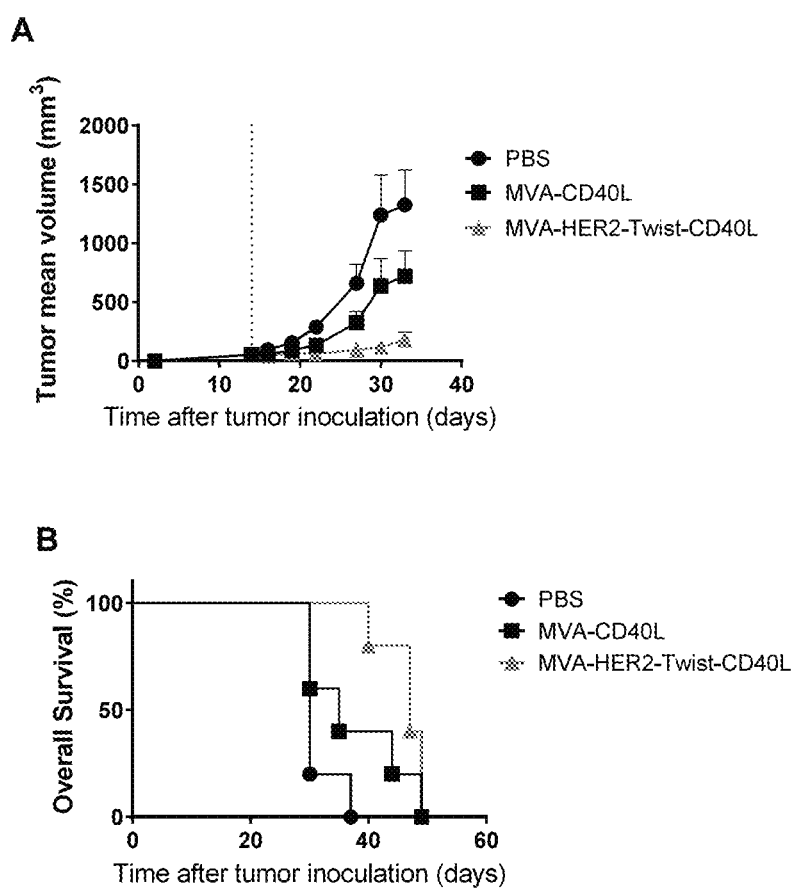
FIGS. 30A and 30B show enhanced anti-tumor effect of IV (intravenous) MVA-HER2-Twist-CD40L immunization over IV (intravenous) MVA-CD40L immunization in a HER2 positive colon carcinoma model. C57BL/6 mice bearing palpable MC38.HER2 tumors were immunized (dotted line) either with PBS, MVA-CD40L or MVA-HER2-Twist-CD40L IV as described in Example 26. Tumor growth was measured at regular intervals. Shown are (FIG. 30A) tumor mean volume and (FIG. 30B) overall survival.

Mouse Colon Carcinoma MC38 cells expressing HER2 (MC38.HER2) were s.c. (subcutaneously) injected into C57BL/6 mice. Mouse Colon Carcinoma CT26 cells expressing HER2 (CT26.HER2) were s.c. injected into Balb/c mice. In both mice groups, when tumors were above 50 $mm^3$ mice bearing MC38.HER2 tumors (FIGS. 30A and 30B) and CT26.HER2 tumors (FIG. 31A and FIG. 31B) were immunized (dotted line) either with PBS, MVA-CD40L or MVA-HER2-Twist-CD40L IV. Tumor growth was measured at regular intervals. In A) tumor mean volume was measure and in B) overall survival of tumor-bearing mice by day 60 after tumor inoculation.

Because the mouse homolog of Brachyury is neither highly expressed in normal mouse tissues nor predominantly expressed in mouse tumor tissues, the efficacy of Brachyury as a target for an active immunotherapy cannot be studied effectively in a mouse model system (see WO 2014/043535, which is incorporated by reference herein). Twist, the mouse homolog of the Human Brachyury is used in mouse models is a predictive model for Brachyury function in humans. This was demonstrated in WO 2014/043535. Like Brachyury, the mouse homolog of the EMT regulator Twist both promotes the EMT during development by down-regulating E-cadherin-mediated cell-cell adhesion and up-regulating mesenchymal markers and is predominantly expressed in mouse tumor tissue (see, e.g., FIG. 5 and Example 8 of WO 2014/043535). Therefore, the study of a Twist-specific cancer vaccine in mice is very likely to have strong predictive value regarding the efficacy of a Brachyury-specific cancer vaccine in humans (Id.).

Example 27: Intravenous Administration of MVA-HER2-Twist-CD40L (mBNbc388) Enhances Infiltration of HER2 Specific CD8+ T Cells into Tumors Balb/c mice bearing CT26.HER2 tumors received intravenously either PBS or $5\times10^7$ $TCID_{50}$ MVA-HER2-Twist-CD40L. Seven days later, mice were sacrificed, spleen and tumor-infiltrating $CD8^+$ T cells isolated by magnetic cell sorting and cultured in the presence of HER2 peptide-loaded dendritic cells for 5 hours. Graph shows percentage of $CD44^+IFN\gamma^+$ cells among $CD8^+$ T cells. Results are shown as Mean±SEM. The results, illustrated in FIG. 32A, demonstrate that the various embodiments of the present invention are tumor specific.

Figure 31:
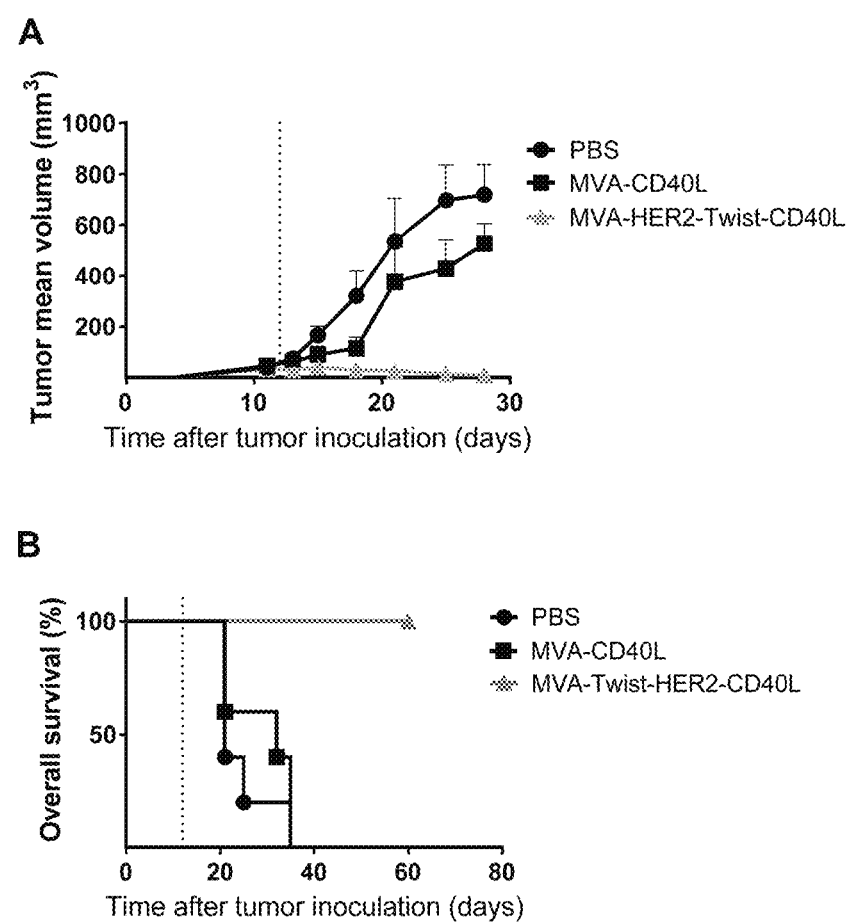
FIGS. 31A and 31B show enhanced anti-tumor effect of IV MVA-HER2-Twist-CD40L immunization over IV MVA-CD40L immunization in a HER2 positive colon carcinoma model. Balb/c mice bearing palpable CT26.HER2 tumors were immunized (dotted line) either with PBS, MVA-CD40L or MVA-HER2-Twist-CD40L IV as described in Example 26. Tumor growth was measured at regular intervals. Shown are (FIG. 31A) tumor mean volume and (FIG. 31B) overall survival.
Figure 32:
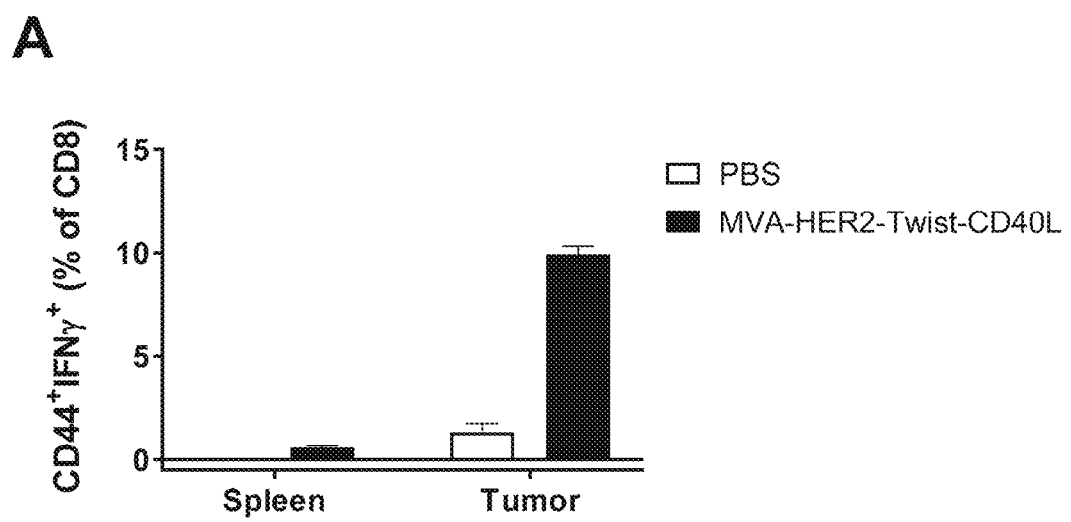
FIG. 32A shows increased infiltration of HER2-specific CD8+ T cells producing IFN-γ in the tumor microenvironment upon IV (intravenous) MVA-HER2-Twist-CD40L immunization. Balb/c mice bearing palpable CT26.HER2 tumors were immunized either with PBS or MVA-HER2-Twist-CD40L IV as described in Example 27. Seven days later, spleen and tumor-infiltrating CD8+ T cells isolated by magnetic cell sorting and cultured in the presence of HER2 peptide-loaded dendritic cells for 5 hours. Graph shows percentage of CD44+IFN-γ+ cells among CD8+ T cells.

Example 28: Increase in Overall Survival and Tumor Reduction in Intravenous Administration of mBNbc388 and mBNbc389 in Combination with Trastuzumab Balb/c mice bearing CT26.HER2 tumors above 100 $mm^3$ mean volume received 5 μg of either human IgG1 or Trastuzumab intraperitoneally on day 15 after tumor inoculation. 2 days after first injection of human IgG1 or Trastuzumab, mice received intravenously PBS or $5\times10^7$ $TCID_5O$ of MVA-HER2-Twist-CD40L as illustrated in FIG. 31. In this example, Human IgG1 is used as an experimental control for Trastuzumab, since IgG1 does not bind HER2 as Trastuzumab does. Tumor growth and overall survival time was measured at regular intervals. (A) Tumor mean volume and (B) mouse survival over time.

Figure 33:
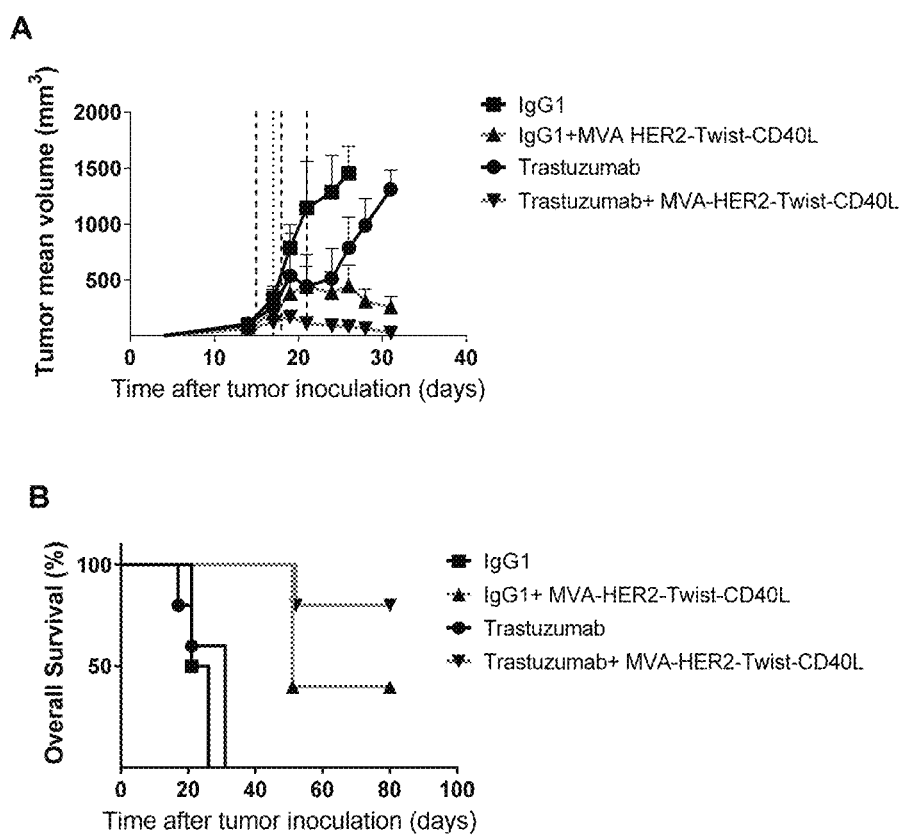
FIGS. 33A and 33B show enhanced anti-tumor effect of MVA-HER2-Twist-CD40L and Trastuzumab (anti-HER2). Balb/c mice bearing large, established 17-day-old CT26.HER2 tumors were immunized IV with MVA-HER2-Twist-CD40L (dotted line) as described in Example 28. Where indicated 5 μg anti-HER2 or huIgG1 were injected IP (dashed line). Shown is the (FIG. 33A) tumor mean volume and (FIG. 33B) overall survival.

Shown in FIGS. 33 (A) and 33(B), the combination of MVA-HER2-Twist-CD40L with Trastuzumab was particularly effective in reducing larger tumors and extending the overall survival rate of mice with those large tumors even at reduced dosage of antibody as compared to Example 21.

Example 29: Overall Survival and Tumor Reduction in IV Administration of MVA-HER2-Twist-CD40L in Orthotopic Breast Cancer Model Balb/c mice bearing orthotopic 4T1.HER2 tumors are primed IV with $5\times10^7$ $TCID_{50}$ MVA-HER2-Twist (mBNbc389) and/or MVA-HER2-Twist-CD40L (mBNbc388). Tumor growth will be measured at regular intervals and overall survival will be recorded.

Example 30: Strong NK Cell Mediated Toxicity from an IV Administration of MVA-HER2-Twist-CD40L+Anti-HER2

C57BL/6 mice are immunized IV with $5\times10^7$ $TCID_{50}$ MVA-HER2-Twist, MVA-HER2-Twist plus anti-Her2, or PBS. 24 hours later mice are sacrificed and splenic NK cells are purified by magnetic cells sorting and will be used as effectors in an effector: target killing assay. Briefly NK cells are cultured with CFSE-labelled MCH class I-deficient YAC-1 cells at the ratios shown in Example 4. Specific killing is assessed by quantifying unviable CFSE+ YAC-1 cells by flow cytometry.

Example 31: IV Administration of MVA-HER2-Twist-CD40L+Anti-HER2 Enhances ADCC C57BL/6 mice are treated IV either with 25 µg anti-CD4, MVA-HER2-TWIST-CD40L+5 µg rat IgG2b, or 1 µg anti-CD4 or MVA-HER2-TWIST-CD40L+1 µg anti-CD4 24 hours later mice are sacrificed and CD4 T cell (CD3$^+$CD4$^+$) depletion in the liver is analyzed by flow cytometry. 25 µg anti-CD4 was defined as 100% specific killing.

To assess ex vivo ADCC activity of NK cells, C57BL/6 (B) or Balb/c (C) mice are immunized IV either with PBS, MVA-HER2-TWIST or MVA-HER2-TWIST-CD40L. 24 hours later mice are sacrificed; splenic NK cells are purified by magnetic cell sorting and used as effectors in antibody-dependent effector: target killing assays. (B) Target MC38-HER2 cells are coated with mouse anti-human/mouse HER2 mAb. Target CT26-HER2 cells are coated with mouse anti-human HER2 mAb. Purified NK cells are added to the antibody-coated target cells at a 5:1 and 4:1 ratio, respectively. Cell death is determined by measuring release of Lactate Dehydrogenase (LDH) into the cell culture medium.

Example 32: Increased Overall Survival and Tumor Reduction in IV Administration of rMVA-CD40+Anti-HER2 at Decreasing Concentrations of HER2 Antibody Balb/c mice bearing palpable CT26-HER2 tumors are immunized IV with MVA-HER2-Twist-CD40L at 5×10$^7$ TCID$_{50}$ on day 8. Mice were intraperitoneally injected with decreasing dosages of anti-HER2 (200 µg, 100 µg, 25 µg) twice/week starting on day 5. Tumor mean volume and overall survival rate are analyzed as compared to mice injected with just 200 µg anti-HER2 antibody and mice injected with just MVA-HER2-TWIST-CD40L.

Example 33: Increased Overall Survival and Tumor Reduction in IV Administration of rMVA-CD40L+Anti-CD52 Antibody Balb/c mice bearing CT26.CD52 tumors receive 5 µg of either human IgG1 or anti-CD52 (alemtuzumab) intraperitoneally after tumor inoculation. After first injection of human IgG1 or alemtuzumab, mice receive intravenously PBS or 5×10$^7$ TCID$_5$O of MVA-CD52-CD40L. Tumor growth and overall survival time are measured at regular intervals. (A) Tumor mean volume and (B) mouse survival over time.

Example 34: Increased Overall Survival and Tumor Reduction in IV Administration of rMVA-CD40 L+Anti-EGFR Antibody Balb/c mice bearing CT26.EGFR tumors receive 5 µg of either human IgG1 or anti-EGFR (cetuximab) intraperitoneally after tumor inoculation. After first injection of human IgG1 or cetuximab, mice receive intravenously PBS or 5×10$^7$ TCID$_{50}$ of MVA-EGFR-CD40L. Tumor growth and overall survival time are measured at regular intervals. (A) Tumor mean volume and (B) mouse survival over time.

It will be apparent that the precise details of the methods or compositions described herein may be varied or modified without departing from the spirit of the described invention. We claim all such modifications and variations that fall within the scope and spirit of the claims below.

---

SEQUENCE LISTING

The nucleic and amino acid sequences listed in the accompanying sequence listing
are shown using standard letter abbreviations for nucleotide bases, and either
one letter code or three letter code for amino acids, as defined in 37 C.F.R.
1.822. Only one strand of each nucleic acid sequence is shown, but the comple-
mentary strand is understood as included by any reference to the displayed strand.

```
SEQ ID NO: 1
Synthetic Her2 v1 amino acid sequence (1,145 amino acids):
MELAALCRWGLLLALLPPGAASTQVCTGTDMKLRLPASPETHLDMLRHLYQGCQ
VVQGNLELTYLPTNASLSFLQDIQEVQGYVLIAHNQVRQVPLQRLRIVRGTQLFED
NYALAVLDNGDPLNNTTPVTGASPGGLRELQLRSLTEILKGGVLIQRNPQLCYQDT
ILWKDIFHKNNQLALTLIDTNRSRACHPCSPMCKGSRCWGESSEDCQSLTRTVCAG
GCARCKGPLPTDCCHEQCAAGCTGPKHSDCLACLHFNHSGICELHCPALVTYNTR
TFKSMPNPEGRYTFGASCVTACPYNYLSTDVGSCTLVCPAANQEVTAEDGTQRCE
KCSKPCARVCYGLGMEHLREVRAVTSANIQEFAGCKKIFGSLAFLPESFDGDPASN
TAPLQPEQLQVFETLEEITGYLYISAWPDSLPDLSVFQNLQVIRGRILHNGAYSLTL
QGLGISWLGLRSLRELGSGLALIHHNTHLCFVHTVPWDQLFRNPHQALLHTANRP
EDECVGEGLACHQLCARGHCWGPGPTQCVNCSQFLRGQECVEECRVLQGLPREY
VNARHCLPCHPECQPQNGSVTCFGPAADQCVACAHYKDPPACVARCPSGVKPDL
SYMPIWAFPDEEGACQPCPINCTHSCVDLDDKGCPAEQRASPLTSIISAVVGILLVV
VLGVVFGILIKRRQQKIRKYTMRRLLQETELVEPLTPSGAMPNQAQMRILKETELR
KVKVLGSGAFGTVYKGIWIPDGENVKIPVAIMVLRENTSPKANKEILDEAYVMAG
VGSPYVSRLLGICLTSTVQLVTQLMPYGCLLDHVRENRGRLGSQDLLNWCMQIAK
GMSYLEDVRLVHRDLAARNVLVKSPNHVKITDFGLARLLDIDETEYHADGGKVPI
KWMALESILRRRFTHQSDVWSYGVTVWELMTFGAKPYDGIPAREIPDLLEKGERL
PQPPICTIDVYMIMVKCWMIDSECRPRFRELVSEFSRMARDPQRFVVIQNEDLGPAS
PLDSTFYRSLLEDDDMGDLVDAEEALVPQQGFFCPDPAPGAGGMVHHRHRSSSTR
SGGGDLTLGLEPSEEEAPRSPLAPSEGAGSDVFDGDLGMGAAKGLQSLPTHDPSPL
QRYSEDPTVPLPSETDGYVAPLTCSPQPELGLDVPV SEQ ID NO: 2
Synthetic Her2 v1 nucleotide sequence (3441 nucleotides):
atggaactggctgctctgtgtagatggggactgctgcttgctctgttgcctcctggagctgcttctacccaagtgtgcacaggcac
cgacatgaagctgagactgcctgcttctcctgagacacacctggacatgctgagacacctgtaccagggatgtcaggtggtgcagg
gaaatctggaactgacctacctgcctaccaacgccagcctgagcttctgcaggacatccaagaggtgcagggatacgtgctgatc
gctcacaatcaagtgagacaggtgccactgcagaggctgagaatcgttagaggcacccagctgttcgaggacaactatgctctggc
tgtgctggacaatggcgaccctctgaacaacaccacacctgtgacaggagcttctcctggtggactgagagaactgcagctgagaa
gcctgaccgagatcctgaaaggaggagtgctgatccagcggaaccctcagctgtgctaccaggacaccatcctgtggaaggaca
```

SEQUENCE LISTING

The nucleic and amino acid sequences listed in the accompanying sequence listing are shown using standard letter abbreviations for nucleotide bases, and either one letter code or three letter code for amino acids, as defined in 37 C.F.R. 1.822. Only one strand of each nucleic acid sequence is shown, but the complementary strand is understood as included by any reference to the displayed strand.

```
tcttccacaagaacaaccagctggctctgacactgatcgacaccaacagaagcagagcctgccatccttgctctcccatgtgcaag
ggctctagatgttggggagagagcagcgaggattgccagagcctgaccagaacagtgtgtgctggaggatgtgccagatgcaaa
ggacctctgcctaccgactgctgccacgagcaatgtgcagctggatgtacaggaccaaagcactctgattgcctggcctgcctgca
cttcaaccactctggaatctgcgagctgcactgtcctgctctggtcacctacaacacacggacctttcaagagcatgcctaatcctg
aaggcagatacacctttggagccagctgtgtgacagcctgtccttacaactacctgagcaccgacgtgggcagtgcacactcgtt
tgtcctgctgccaatcaagaagtgacagccgaggacggcacccagagatgcgagaagtgtagcaagccttgcgctagagtgtgtta
cggactcggcatggaacacctgagagaagtgagagccgtgaccagttgccaacatccaagagtttgctggctgcaagaagatctttg
gcagcctcgccttcctgcctgagagcttcgatggcgatcctgccagcaatactgctcctctgcagcctgaacagctccaggtgttc
gagacactggaagagatcacaggctacctgtacatcagcgcatggccagacagcctgcctgacctgtccgtgttccagaacctgca
agtgatcagaggcagaatcctgcacaacggagcctattctctgaccctgcaaggcctgggaatcagctggctgggactgagatcc
ctgagagagcttggatctgccctggctctgatccaccacaataccacctgtgcttcgtgcacaccgtgccttgggaccagctgtt
tcggaatcctcatcaggctctgctgcacacagccaacagacctgaggatgagtgtgttggcgaaggcctggcttgtcaccagctct
gtgctagaggacactgttggggacctggacctacacagtgtgtgaactgtagccagttcctgagaggccaagaatgcgtggaagag
tgtagagttctgcagggactgcctcgcgagtacgtgaacgctagacactgtctgccttgtcatcccgagtgccagcctcagaatgg
cagcgtgacatgttttggaccagctgccgatcagtgcgtggcctgtgctcactataaggaccctccagcctgcgtggccagatgtc
ctagcggagtgaagcctgacctgagctacatgcccatctgggcatttccagatgaggaaggagcttgccagccttgtcctatcaac
tgcacccacagctgcgtggacctggacgataaggatgtccagccgagcagagacctctccactgacctctatcatctctgccgt
cgtgggcatcctgctggtggtggttctgggagttgtgttcggcatcctgatcaagagacggcagcagaagatccggaagtacacca
tgcggagactgctgcaagagactgagctggtggaacctctgacacccagcggagctatgcctaaccaggctcagatgcggattct
gaaagaaaccgagctgcggaaagtgaaggtgctcggctctggagcctttggcacagtgtacaaaggcatctggatccctgacgg
agagaacgtgaagattcctgtggccatcatggtgctgagagagaacacaagtcccaaggccaacaaagagatcctggacgaggc
ctacgtgatggctggtgttggcagcccttatgtgtctagactgctgggcatctgtctgaccagcaccgtgcagctggtcactcagc
tgatgcctcacggctgcctgctggatcacgtgagagagaatagaggcgaactgggctctcaggacctgctgaactggtgcatgcag
atcgccaagggcatgagctacctcgaggatgtgagactggtccacagagatctggctgccagaaacgtgctcgtgaagtctcctaa
ccacgtgaagatcaccgacttcggactggctaggctgctggatatcgacgagacagagtaccacgctgatgaggcaaggtgcc
catcaagtggatggctctggaatccatcctgagacggagattcacccaccagtccgatgtggtcttacggagtgacagtgtggg
agctgatgaccttcggagccaagccttacgacgggcatccctgccagagagatcccagatctgctggaaaagggagagagactgc
ctcagcctcctatctgcaccatcgacgtgtacatgattatggtcaagtgttggatgatcgacagcgagtgcagacccagattcaga
gaactggtgtccgagttctctcggatggccagagatcctcagagattcgtggtcatccagaacgaggatctgggacctgccagccc
tctggacagcaccttctacagatccctgctggaagatgacgacatgggtgacctggtggacgctgaagaagctctggttcctcagc
agggcttcttctgccctgatcctgctccaggagcaggtggaatggtgcatcacagacacagaagctccagccacagaagcggagg
cggagatctgacactgggactcgagccatctgaggaagaggctcctagatctcctctggcctccttctgaaggagctggaagcgac
gttttcgacggagatcttggaatgggagctgccaaaggactccagtctctgcccacacacgacccatctccactgcagagatacag
cgaggacctaccgtgcctctgccaagcgagacagatggatatgtggcacctctgacctgctctcctcagccagaactgggacttg
atgtgcctgtttgatga
```

SEQ ID NO: 3
Synthetic Brachyury amino acid sequence (427 amino acids nucleotides):
MSSPGTESAGKSLQYRVDHLLSAVENELQAGSEKGDPTERELRVGLEESELWLRF
KELTNEMIVTKNGRRMFPVLKVNVSGLDPNAMYSFLLDFVAADNHRWKYVNGE
WVPGGKPEPQAPSCVYIHPDSPNFGAHWMKAPVSFSKVKLTNKLNGGGQIMLNSL
HKYEPRIHIVRVGGPQRMITSHCFPETQFIAVTAYQNEEITALKIKYNPFAKAFLDA
KERSDHKEMMEEPGDSQQPGYSQWGWLLPGTSTLCPPANPHPQFGGALSLPSTHS
CDRYPTLRSHYAHRNNSPTYSDNSPACLSMLQSHDNWSSLGMPAHPSMLPVSHN
ASPPTSSSQYPSLWSVSNGAVTPGSQAAAVSNGLGAQFFRGSPAHYTPLTHPVSAP
SSSGSPLYEGAAAATDIVDSQYDAAAQGRLIASWTPVSPPSM

SEQ ID NO: 4
Synthetic Brachyury nucleotide sequence (1,287 nucleotides):
```
atgtctagccctggcacagagtctgctggcaagagcctccagtacagagtggaccatctgctgagcgctgtggagaatgaactgc
aggctggaagcgagaagggagatcctacagaaagagagctgagagtcggactggaagagtccgagctgtggctgcggttcaaa
gaactgaccaacgagatgatcgtgaccaagaacggcagacggattgttccctgtgctgaaagtgaacgtgtccggactggaccta
acgccatgtacagctttctgctggatttcgtggcagctgacaaccacagatggaagtacgtgaacggagagtgggtgccaggagg
aaaacctgaacctcaggctcctagctgcgtgtacattcaccctgacagccctaacttcggagcccactggatgaaggctcctgtgt
ccttcagcaaagtgaagctgaccaacaagctgaacggaggaggccagatcatgctgaacagcctgcacaagtatgagcctaggat
ccacatcgtcagagttggaggccctcagcggatgatcaccagccactgtttccctgagcacagttcatcgcagtgaccgcttacc
agaacgaggaaatcacagccctgaagatcaagtacaatcccttcgccaaggccttcctggacgccaaagagcggagcgaccac
aaagaaatgatggaagaacctggcgacagccagcagcctggctattctcaatggggatggctgctgccaggcacctccacattgt
gccctccagccaatcctcatcctcagtttggcggagccctgagcctgcctagcacacacagctgcgacagataccctacactgaga
agccactacgctcacagaaacaacagccctacctacagcgacaatagccctgcctgtctgagcatgctgcagtcccacgacaatt
ggtccagcctgggaatgcctgctcacccttctatgctgcctgtctctcacaagcctctccacctacaagcagctctcagtaccct
agcctttggagcgtgtccaatggagctgtgacacctggatctcaggctgccgctgtgtctaatggactgggagcccagttcttcag
aggcagccctgctcactacacacctctgacacatccagtgtctgctcctagcagcagcggaagccctctctatgaaggagccgctg
cagccaccgacatcgtggattctcagtatgatgctgccgcacagggcagactgatcgcctcttggacacctgtgagcccaccttcc
atgtgatga
```

SEQ ID NO: 5 (435 aa)
Brachyury protein Isoform 1 from GenBank Accession No. O15178.1
MSSPGTESAGKSLQYRVDHLLSAVENELQAGSEKGDPTERELRVGLEESELWLRF
KELTNEMIVTKNGRRMFPVLKVNVSGLDPNAMYSFLLDFVAADNHRWKYVNGE WVPGGKPEPQAPSCVYIHPDSPNFGAHWMKAPVSFSKVKLTNKLNGGGQIMLNSL
HKYEPRIHIVRVGGPQRMITSHCFPETQFIAVTAYQNEEITALKIKYNPFAKAFLDA
KERSDHKEMMEEPGDSQQPGYSQWGWLLPGTSTLCPPANPHPQFGGALSLPSTHS
CDRYPTLRSHRSSPYPSPYAHRNNSPTYSDNSPACLSMLQSHDNWSSLGMPAHPS
MLPVSHNASPPTSSSQYPSLWSVSNGAVTPGSQAAAVSNGLGAQFFRGSPAHYTPL
THPVSAPSSSGSPLYEGAAAATDIVDSQYDAAAQGRLIASWTPVSPPSM SEQ ID NO: 6 (1308 nt)
Coding sequence for Brachyury protein Isoform 1 GenBank Accession No. O15178.1
atgagcagccctggcacagagagcgccggcaagagcctgcagtaccgggtggaccatctgctgagcgccgtggagaatgagct
gcaggccggctccgagaagggcgaccccaccgagagggaactgagagtgggcctggaagagtccgagctgtggctgcggttc
aaagaactgaccaacgagatgatcgtgaccaagaacggcagacggatgttccccgtgctgaaagtgaacgtgtccggcctggac
cccaacgccatgtacagctttctgctggacttcgtggccgccgacaaccacaggtggaaatacgtgaacggcgagtgggtgccag
gcggcaaacctgagcctcaggcccccagctgcgtgtatatccaccccgacagccccaatttcggcgcccactggatgaaggccc
ccgtgtccttcagcaaagtgaagctgaccaacaagctgaacggcggaggccagatcatgctgaacagcctgcacaagtacgagc
cccggatccacattgtgcgcgtgggcggaccccagagaatgatcaccagccactgcttccccgagacagtttatcgccgtgac
cgcctaccagaacgaggaaatcaccgccctgaagatcaagtacaaccccttcgccaaggccttcctggacgccaaagagcgga
gcgaccacaaagaaatgatggaagaacccggcgacagccagcagcctggctacagccagtggggctggctgctgccaggcac
ctccactctgtgcccccctgccaaccctcaccctcagttcggcggagccctgagcctgcctagcacacacagctgcgacagatac
cccaccctgcggagccacagaagcagccctaccccagcccatacgccaccggaacaacagccccacctacagcgacaact
cccccgcctgcctgagcatgctgcagagccacgacaactggtccagcctgggcatgcctgcccaccctagcatgctgcccgtgtc
ccacaatgccagccccctaccagcagctcccagtaccctagcctgtggagcgtgtccaatggcgccgtgacacctggatctcag
gccgctgccgtgagcaatggctgggagcccagttctttagaggcagccctgcccactacacccctctgaccccacctgtgtccg
ccctagctccagcggcagccctctgtatgaaggcgccgctgcagccaccgatatcgtggacagccagtacgatgccgccgctc
agggcagactgatcgccagctggacccccgtgtctcccccacagcatgtga SEQ ID NO: 7 (435 aa)
Brachyury protein Isoform 1 (L254V).
MSSPGTESAGKSLQYRVDHLLSAVENELQAGSEKGDPTERELRVGLEESELWLRF
KELTNEMIVTKNGRRMFPVLKVNVSGLDPNAMYSFLLDFVAADNHRWKYVNGE
WVPGGKPEPQAPSCVYIHPDSPNFGAHWMKAPVSFSKVKLTNKLNGGGQIMLNSL
HKYEPRIHIVRVGGPQRMITSHCFPETQFIAVTAYQNEEITALKIKYNPFAKAFLDA
KERSDHKEMMEEPGDSQQPGYSQWGWLLPGTST*V***CPPANPHPQFGGALSLPSTHS
CDRYPTLRSHRSSPYPSPYAHRNNSPTYSDNSPACLSMLQSHDNWSSLGMPAHPS
MLPVSHNASPPTSSSQYPSLWSVSNGAVTPGSQAAAVSNGLGAQFFRGSPAHYTPL
THPVSAPSSSGSPLYEGAAAATDIVDSQYDAAAQGRLIASWTPVSPPSM SEQ ID NO: 8 (1308 nt)
Coding sequence encoding Brachyury protein Isoform 1 with L254V.
atgagctcccctggcaccgagagcgcgggaaagagcctgcagtaccgagtggaccacctgctgagcgccgtggagaatgagct
gcaggccgggcagcgagaagggcgaccccacagagcgcgaactgcgcgtgggcctggaggagagcgagctgtggctgcgctt
caaggagctcaccaatgagatgatcgtgaccaagaacggcaggaggatgttccggtgctgaaggtgaacgtgtctggcctggac
cccaacgccatgtactccttcctgctggacttcgtggcggcggacaaccaccgctggaagtacgtgaacggggaatgggtgccg
ggggcaagccggagccgcaggcgcccagctgcgtctacatccaccccgactgcccaacttcggggcccactggatgaagg
ctcccgtctccttcagcaaagtcaagctcaccaacaagctcaacggagggggccagatcatgctgaactcctcgcataagtatgag
cctcgaatccacatagtgagagttgggggtccacagcgcatgatcaccagccactgcttccctgagacccagttcatagcggtgac
tgcttatcagaacgaggagatcacagctcttaaaattaagtacaatccatttgcaaaggctttccttgatgcaaaggaaagaagtg
atcacaaagatgatggaggaacccggagacagccagcaacctgggtactcccaatggggggtggcttcttcctggaaccagcacc
gtttgtccacctgcaaatcctcatcctcagtttggaggtgccctctccctccctccacgcacagctgtgacaggtaccaaccct
gaggagccaccggtcctcaccctaccccagccctatgctcatcggaacaattctccaacctattctgacaactcacctgcatgtt
tatccatgctgcaatccatgacaattggtccagcctggaatgctgcccatcccagcatgctccccgtgagccacaatgccagc
ccacctaccagctccagtcagtaccccagcctgtggtctgtgagcaacggcgccgtcaccccgggctcccaggcagcagccgtgtc
caacgggctggggggccagttcttccggggctcccccgcgcactacacaccctcacccatccggtctcggcgccctcttcctcgg
gatccccactgtacgaaggggcggccggccacagacatcgtggacagccagtacgacgccgcagcccaaggccgcctcatagcc
tcatggacacctgtgtcgccaccttccatgtga SEQ ID NO: 9 (449 aa)
Brachyury-I3 fusion protein
MKNNLYEEKMNMSKKSSPGTESAGKSLQYRVDHLLSAVENELQAGSEKGDPTER
ELRVGLEESELWLRFKELTNEMIVTKNGRRMFPVLKVNVSGLDPNAMYSFLLDFV
AADNHRWKYVNGEWVPGGKPEPQAPSCVYIHPDSPNFGAHWMKAPVSFSKVKL
TNKLNGGGQIMLNSLHKYEPRIHIVRVGGPQRMITSHCFPETQFIAVTAYQNEEITA
LKIKYNPFAKAFLDAKERSDHKEMMEEPGDSQQPGYSQWGWLLPGTSTVCPPAN
PHPQFGGALSLPSTHSCDRYPTLRSHRSSPYPSPYAHRNNSPTYSDNSPACLSMLQS
HDNWSSLGMPAHPSMLPVSHNASPPTSSSQYPSLWSVSNGAVTPGSQAAAVSNGL
GAQFFRGSPAHYTPLTHPVSAPSSSGSPLYEGAAAATDIVDSQYDAAAQGRLIASW
TPVSPPSM SEQ ID NO: 10 (1350 nt)
Coding sequence encoding I3 Brachyury fusion protein of SEQ ID NO 9
atgaaaaataacttgtatgaagaaaaaatgaacatgagtaagaaaagctcccctggcaccgagagcgcgggaaagagcctgcag
taccgagtggaccacctgctgagcgccgtggagaatgagctgcaggccgggcagcgagaagggcgaccccacagagcgcgaa

```
ctgcgcgtgggcctggaggagagcgagctgtggctgcgcttcaaggagctcaccaatgagatgatcgtgaccaagaacggcag
gaggatgtttccggtgctgaaggtgaacgtgtctggcctggaccccaacgccatgtactccttcctgctggacttcgtggcggcgg
acaaccaccgctggaagtacgtgaacggggaatgggtgccgggggggcaagccggagccgcaggcgcgcccagctgcgtctacat
ccaccccgactcgcccaacttcggggcccactggatgaaggctcccgtctccttcagcaaagtcaagctcaccaacaagctcaac
ggaggggccagatcatgctgaacctcttgcataagtatgagcctcgaatccacatagtgagagttgggggtccacagcgcatgat
caccagccactgcttccctgagacccagttcatagcggtgactgcttatcagaacgaggagatcacagctcttaaaattaagtaca
atccatttgcaaaggctttccttgatgcaaaggaaagaagtgatcacaaaggatgatggaggaacccggagacagccagcaacct
gggtactcccaatgggggtggcttcttcctggaaccagcaccgtttgtccacctgcaaatcctcatcctcagtttggaggtgccct
ctccctccccctccacgcacagctgtgacaggtacccaaccctgaggagccaccggtcctcacccctacccagcccctatgctcatc
ggaacaattctccaacctattctgacaactcacctgcatgtttatccatgctgcaatcccatgacaattggtccagccttggaatg
cctgcccatcccagcatgctccccgtgagccacaatgccagcccacctaccagctccagtcagtaccccagcctgtggtctgtgag
caacggcgccgtcaccccgggctcccaggcagcagccgtgtccaacgggctgggggcccagttcttccggggctcccccgcgcact
acacaccctcacccatccggtctcggcgcctcttcctcgggatcccactgtacgaaggggcggccgcggccacagacatcgtg
gacagccagtacgacgccgcagcccaaggccgcctcatagcctcatggacacctgtgtcgccaccttccatgtga
```

SEQ ID NO: 11
hCD40L from NCBI RefSeq NP_000065.1. (261 amino acids)
MIETYNQTSPRSAATGLPISMKIFMYLLTVFLITQMIGSALFAVYLHRRLDKIEDER
NLHEDFVFMKTIQRCNTGERSLSLLNCEEIKSQFEGFVKDIMLNKEETKKENSFEM
QKGDQNPQIAAHVISEASSKTTSVLQWAEKGYYTMSNNLVTLENGKQLTVKRQG
LYYIYAQVTFCSNREASSQAPPIASLCLKSPGRFERILLRAANTHSSAKPCGQQSIHL
GGVFELQPGASVFVNVTDPSQVSHGTGFTSFGLLKL SEQ ID NO: 12
hCD40L from NCBI RefSeg NP_000065.1. (789 nucleotides)
atgatcgagacatacaaccagacaagccctagaagcgccgccacaggactgcctatcagcatgaagatcttcatgtacctgctgac
cgtgttcctgatcacccagatgatcggcagcgccctgttgccgtgtacctgcacagacggctggacaagatcgaggacgagaga
aacctgcacgaggacttcgtgttcatgaagaccatccagcggtgcaacaccggcgagagaagtctgagcctgctgaactgcgag
gaaatcaagagccagttcgagggcttcgtgaaggacatcatgctgaacaaagaggaaacgaagaaagagaactccttcgagatg
cagaagggcgaccagaatcctcagatcgccgctcacgtgatcagcgaggccagcagcaagacaacaagcgtgctgcagtgg
ccgagaagggctactacaccatgagcaacaacctggtcaccctggagaacggcaagcagctgacagtgaagcggcagggcct
gtactacatctacgcccaagtgaccttctgcagcaacagagaggccagctctccaggctcctttcatcgccagcctgtgcctgaagt
ctcctggcagattcgagcggattctgctgagagccgccaacacacacagcagcgccaaacctgtggccagcagtctattcacctc
ggcggagtgtttgagctgcagcctggcgcaagcgtgttcgtgaatgtgacagaccctagccaggtgtcccacggcaccggctttac
atcttccggactgctgaagctgtgatga SEQ ID NO: 13
Synthetic Her2 v2 amino acid sequence (1,145 amino acids):
MELAALCRWGLLLALLPPGAASTQVCTGTDMKLRLPASPETHLDMLRHLYQGCQVVQGNLE
LTYLPTNASLSFLQDIQEVQGYVLIAHNQVRQVPLQRLRIVRGTQLFEDNYALAVLDNGDP
LNNTTPVTGASPGGLRELQLRSLTEILKGGVLIQRNPQLCYQDTILWKDIFHKNNQLALTL
IDTNRSRACHPCSPMCKGSRCWGESSEDCQSLTRTVCAGGCARCKGPLPTDCCHEQCAAGC
TGPKHSDCLACLHFNHSGICELACPALVTYNTRTAKSMPNPEGRYTFGASCVTACPYNYLS
TDAGACTLVCPAANQEVTAEDGTQRCEACSKACARVCYGLGMEHLREVRAVTSANIQEFAG
CKKIEGSLAFLPESEDGDPASNTAPLQPEQLQVFETLEEITGYLYISAWPDSLPDLSVFQN
LQVIRGRILHNGAYSLTLQGLGISWLGLRSLRELGSGLALIHHNTHLCFVHTVPWDQLFRN
PHQALLHTANRPEDECVGEGLACHQLCARGHCWGPGPTQCVNCSQFLRGQECVEECRVLQG
LPREYVNARHCLPCHPECQPQNGSVTCFGPAADQCVACAHYKDPPACVARCPSGVKPDLSY
MPIWAFPDEEGACQPCPINCTHSCVDLDDKGCPAEQRASPLTSIISAVVGILLVVVLGVVF
GILIKRRQQKIRKYTMRRLLQETELVEPLTPSGAMPNQAQMRILKETELRKVKVLGSGAFG
TVYKGIWIPDGENVKIPVAIMVLRENTSPKANKEILDEAYVMAGVGSPYVSRLLGICLTST
VQLVTQLMPYGCLLDHVRENRGRLGSQDLLNWCMQIAKGMSYLEDVRLVHRDLAARNVLVK
SPNHVKITDFGLARLLDIDETEYHADGGKVPIKWMALESILRRRFTHQSDVWSYGVTVWEL
MTFGAKPYDGIPAREIPDLLEKGERLPQPPICTIDVYMIMVKCWMIDSECRPRFRELVSEF
SRMARDPQRFVVIQNEDLGPASPLDSTFYRSLLEDDDMGDLVDAEEALVPQQGFECPDPAP
GAGGMVHHRHRSSSTRSGGGDLTLGLEPSEEEAPRSPLAPSEGAGSDVFDGDLGMGAAKGL
QSLPTHDPSPLQRYSEDPTVPLPSETDGYVAPLTCSPQPELGLDVPV SEQ ID NO: 14
Synthetic Her2 v2 nucleotide sequence (3441 nucleotides):
atggaactggctgctctgtgtagatggggactgctgcttgctctgttgcctcctggagctg
cttctacccaagtgtgcacaggcaccgacatgaagctgagactgcctgcttctcctgagac
acacctggacatgctgagacacctgtaccagggatgtcaggtggtgcagggaaatctggaa
ctgacctacctgcctaccaacgccagcctgagctttctgcaggacatccaagaggtgcagg
gatacgtgctgatcgctcacaatcaagtgagacaggtgccactgcagaggctgagaatcgt
tagaggcacccagctgttcgaggacaactatgctctggctgtgctggacaatggcgaccct
ctgaacaacaccacacctgtgacaggagcttctcctggtggctgagagaagctcagctga
gaagcctgaccgagatcctgaaaggaggagtgctgatccagcggaacctcagctgtgcta
ccaggacaccatcctgtggaaggacatcttccacaagaacaaccagctggctctgacactg
atcgacaccaacagaagcagagcctgccatccttgctctcccatgtgcaaggctctagat
gttggggagagagcagcgaggattgccagagcctgaccagaacagtgtgtgctggaggatg
tgccagatgcaaaggacctctgcctaccgactgctgccacgagcaatgtgcagctggatgt
```

SEQUENCE LISTING
The nucleic and amino acid sequences listed in the accompanying sequence listing
are shown using standard letter abbreviations for nucleotide bases, and either
one letter code or three letter code for amino acids, as defined in 37 C.F.R.
1.822. Only one strand of each nucleic acid sequence is shown, but the comple-
mentary strand is understood as included by any reference to the displayed strand.

```
acaggaccaaagcactctgattgcctggcctgcctgcacttcaaccactctggaatctgcg
agctcgcctgtcctgctctggtcacctacaacacacggaccgccaagagcatgcctaatcc
tgaaggcagatacacctttggagccagctgtgtgacagcctgtccttacaactacctgagc
accgacgctggagcctgcacactcgtttgtcctgctgccaatcaagaagtgacggccgagg
acggcacccagagatgcgaggcctgtagcaaggcttgcgctagagtgtgttacggactcgg
catggaacacctgagagaagtgagagccgtgaccagtgccaacatccaagagtttgctggc
tgcaagaagatctttggcagcctcgccttcctgcctgagagcttcgatgcgatcctgcca
gcaatactgctcctctgcagcctgaacagctccaggtgttcgagacactggaagagatcac
aggctacctgtacatcagcgcatggccagacagcctgcctgacctgtccgtgttccagaac
ctgcaagtgatcagaggcagaatcctgcacaacggagcctattctctgacctgcaaggcc
tgggaatcagctggctgggactgagatccctgagagagcttggatctggcctggctctgat
ccaccacaatacccacctgtgcttcgtgcacaccgtgccttgggaccagctgtttcggaat
cctcatcaggctctgctgcacacagccaacagacctgaggatgagtgtgttggcgaaggcc
tggcttgtcaccagctctgtgctagaggacactgttggggacctggacctacacagtgtgt
gaactgtagccagttcctgagaggccaagaatgcgtggaagagtgtagagttctgcaggga
ctgcctcgcgagtacgtgaacgctagacactgtctgccttgtcatcccgagtgccagcctc
agaatggcagcgtgacatgttttggaccagctgccgatcagtgcgtggcctgtgctcacta
taaggaccctccagcctgcgtggccagatgtcctagcggagtgaagcctgacctgagctac
atgcccatctgggcatttccagatgaggaaggagcttgccagccttgtcctatcaactgca
cccacagctgcgtggacctggacgataagggatgtccagccgagcagagagcctctccact
gacctctatcatctctgccgtcgtgggcatcctgctggtggtggttctgggagttgtgttc
ggcatcctgatcaagagacggcagcagaagatccggaagtacaccatgcggagactgctgc
aagagactgagctggtggaacctctgacacccagcggagctatgcctaaccaggctcagat
gcggattctgaaagaaaccgagctgcggaaagtgaaggtgctcggctctggagcctttggc
acagtgtacaaaggcatctggatccctgacggagagaacgtgaagattcctgtggccatca
tggtgctgagagagaacacaagtcccaaggccaacaaagagatcctggacgaggcctacgt
gatggctggtgttggcagcccttatgtgtctagactgctgggcatctgtctgaccagcacc
gtgcagctggtcactcagctgatgcctctacggctgcctgctggatcacgtgagagagaata
gaggcagactgggctctcaggacctgctgaactggtgcatgcagatcgccaagggcatgag
ctacctcgaggatgtgagactggtccacagagatctggctgccagaaacgtgctcgtgaag
tctcctaaccacgtgaagatcaccgacttcggactggctaggctgctggatatcgacgaga
cagagtaccacgctgatggaggcaaggtgcccatcaagtggatggctctggaatccatcct
gagacggagattcacccaccagtccgatgtgtggtcttacggagtgacagtgtgggagctg
atgaccttcggagccaagccttacgacggcatccctgccagagagatcccagatctgctgg
aaaagggagagagactgcctcagcctcctatctgcaccatcgacgtgtacatgattatggt
caagtgttggatgatcgacagcgagtgcagacccagattcgagaactggctctggagttc
tctcggatggccagagatcctcagagattcgtggtcatccagaacgaggatctgggacctg
ccagccctctggacagcaccttctacagatccctgctggaagatgacgacatgggtgacct
ggtggacgctgaagaagctctggttcctcagcagggcttcttctgccctgatcctgctcca
ggagcaggtggaatggtgcatcacagacacagaagctccagcaccagaagcggaggcggag
atctgacactgggactcgagccatctgaggaagaggctcctagatctcctctggctccttc
tgaaggagctggaagcgacgttttcgacggagatcttggaatgggagctgccaaaggactc
cagtctctgcccacacacgacccatctccactgcagagatacagcgaggaccctaccgtgc
ctctgccaagcgagacagatggatatgtggcacctctgacctgctctcctcagccagaact
gggacttgatgtgcctgtttgatga
```

SEQ ID NO: 15
Synthetic Twist amino acid sequence (205 amino acids):
MQDVSSSPVSPADDSLSNSEEEPDRQQPASGKRGARKRRSSRRSAGGSAGPGGAT
GGGIGGGDEPGSPAQGKRGKKSAGGGGGGAGGGGGGGGGSSSGGGSPQSYEEL
QTQRVMANVRERQRTQSLNEAFAALRKIIPTLPSDKLSKIQTLKLAARYIDFLYQV
LQSDELDSKMASCSYVAHERLSYAFSVWRMEGAWSMSASH SEQ ID NO: 16
Synthetic Twist nucleotide sequence (618 nucleotides):
atgcaggacgtgtccagcagccctgtgtctcctgccgacgacagcctgagcaacagcgaggaagaacccgacagacagcagcc
cgcctctggcaagagaggcgccagaaagagaagaagctccagaagaagcgctggcggctctgctggacctggcggagctaca
ggcggaggaattggaggcggagatgagcctggctctccagcccagggcaagagggcaagaaatctgctggcggaggcggc
ggaggaggagctggaggcggaggaggaggcggcggaggatcaagttctggcggaggaagccctcagagctacgaggaact
gcagacccagcgcgtgatggccaacgtgcgcgagagacagagaacccagagcctgaacgaggccttcgccgccctgagaaa
gatcatccccaccctgcccagcgacaagctgagcaagatccagaccctgaagctggccgccagatatatcgacttcctgtatcaag
tgctgcagagcgacgagctggacagcaagatggccagctgctcctacgtggcccacgagagactgagctacgccttcagcgtgt
ggcggatggaaggcgcctggtctatgagcgccagccactga SEQ ID NO: 17
Synthetic murine CD40L amino acid sequence (260 amino acids):
MIETYSQPSPRSVATGLPASMKIFMYLLTVFLITQMIGSVLFAVYLHRRLDKVEEEVNLHE
DFVFIKKLKRCNKGEGSLSLLNCEEMRRQFEDLVKDITLNKEEKKENSFEMQRGDEDPQIA
AHVVSEANSNAASVLQWAKKGYYTMKSNLVMLENGKQLTVKREGLYYVYTQVTFCSNREPS
SQRPFIVGLWLKPSSGSERILLKAANTHSSSQLCEQQSVHLGGVFELQAGASVFVNVTEAS
QVIHRVGFSSFGLLKL

SEQUENCE LISTING

The nucleic and amino acid sequences listed in the accompanying sequence listing are shown using standard letter abbreviations for nucleotide bases, and either one letter code or three letter code for amino acids, as defined in 37 C.F.R. 1.822. Only one strand of each nucleic acid sequence is shown, but the complementary strand is understood as included by any reference to the displayed strand.

SEQ ID NO: 18
Synthetic murine CD40L nucleotide sequence (786 nucleotides):
atgatcgagacatacagccagcccagcccagaagcgtggccacaggactgcctgccagca
tgaagatctttatgtacctgctgaccgtgttcctgatcacccagatgatcggcagcgtgct
gttcgccgtgtacctgcacagacggctggacaaggtggaagaggaagtgaacctgcacgag
gacttcgtgttcatcaagaaactgaagcggtgcaacaagggcgagggcagcctgagcctgc
tgaactgcgaggaaatgaagggcagttcgaggacctcgtgagagacatcaccctgaacaa
agaggaaaagaaagaaaactccttcgagatgcagaggggcgacgaggaccctcagatcgct
gctcacgtggtgtccgaggccaacagcaacgccgcttctgtgctgcagtgggccaagaaag
gctactacaccatgaagtccaacctcgtgatgctggaaaacggcaagcagctgacagtgaa
gcgcgagggcctgtactatgtgtacacccaagtgacattctgcagcaacagagagcccagc
agccagaggccctccatcgtgggactgtggctgaagcctagcagcggcagcgagagaatcc
tgctgaaggccgccaacacccacagcagctctcagctgtgcgagcagcagagcgtgcacct
gggcggagtgttcgagctgcaagctggcgcctccgtgttcgtgaacgtgacagaggccagc
caagtgatccacagagtgggcttcagcagctttggactgctgaaactgtaatga

REFERENCES

The references included as part of the present disclosure, in addition to those listed below, are hereby incorporated by reference in their entirety: World Health Organization, World Health report (2013); Torre, "Global Cancer Statistics" (2012) CA: A Cancer Journal for Clinicians; Ross (2003), "The Her-2/neu gene and protein in breast cancer 2003: biomarker and target of therapy," Oncologist; Palena (2007) Clin. Cancer Res., "The human T-box mesodermal transcription factor Brachyury is a candidate target for T-cell-mediated cancer immunotherapy"; Hynes and Lane (2005) Nat. Rev. Cancer, "ERBB receptors and cancer: the complexity of targeted inhibitors"; Cho (2003) Nature, "Structure of the extracellular region of HER2 alone and in complex with the Herceptin Fab"; Satyanarayanajois (2009) Chem. Biol. Drug Des., "Design, Synthesis, and Docking Studies of Peptidomimetics based on HER2-Herceptin Binding Site with Potential Antiproliferative Activity Against Breast Cancer Cell lines"; Franklin (2004) Cancer Cell, "Insights into ErbB signaling from the structure of the ErbB2-pertuzumab complex"; Yang (2009), Paper 391, "Targeting The Dimerization Of ERBB Receptor," All Theses and Dissertations; Tan (2005) Cancer Res., "ErbB2 promotes Src synthesis and stability: novel mechanisms of Src activation that confer breast cancer metastasis"; Roskoski (2014) Pharmacol. Res. "ErbB/HER protein-tyrosine kinases: Structures and small molecule inhibitors"; Roselli (2012) Clin. Cancer Res., "Brachyury, a driver of the epithelial-mesenchymal transition, is overexpressed in human lung tumors: an opportunity for novel interventions against lung cancer"; Stoller and Epstein (2005) Hum. Mol. Genet., "Identification of a novel nuclear localization signal in Tbx1 that is deleted in DiGeorge syndrome patients harboring the 1223delC mutation"; Lauterbach (2013) Front. Immunol., "Genetic Adjuvantation of Recombinant MVA with CD40L Potentiates CD8 T Cell Mediated Immunity"; Guardino et al. (2009) Cancer Res. 69 (24 Supp): Abstract nr 5089, "Results of Two Phase I Clinical Trials of MVA-BN®-HER2 in HER-2 Overexpressing Metastatic Breast Cancer Patients"; Heery et al. (2015) J. Immunother. Cancer 3 (Suppl. 2): P132, "Phase I, dose-escalation, clinical trial of MVA-Brachyury-TRICOM vaccine demonstrating safety and brachyury-specific T cell responses"; Brodowicz et al. (2001) Br. J Cancer, "Anti-Her-2/neu antibody induces apoptosis in Her-2/neu overexpressing breast cancer cells independently from p53 status"; Stackaruk et al. (2013) Expert Rev. Vaccines 12(8):875-84, "Type I interferon regulation of natural killer cell function in primary and secondary infections"; Muller et al. (2017) Front. Immunol. 8: 304, "Type I Interferons and Natural Killer Cell Regulation in Cancer"; Yamashita et al. (January 2016) Scientific Reports 6 (Article number 19772), "A novel method for evalulating antibody dependent cell-mediated cytotoxicity by flow cytometry using human peripheral blood mononuclear cells"; Broussas et al. (2013) Methods Mol. Biol. 988: 305-17, "Evaluation of antibody-dependent cell cytotoxicity using lactate dehydrogenase (LDH) measurement"; Tay et al. (2016) Hum. Vaccines and Immunother. 12: 2790-96, "TriKEs and BiKEs join CARs on the cancer immunotherapy highway"; and Kono et al. (2004) Clin. Cancer Res.10: 2538-44, "Trastuzumab (Herceptin) Enhances Class I-Restricted Antigen Presentation Recognized by Her2/neu Specific T Cytotoxic Lymphocytes."

SEQUENCE LISTING

<160> NUMBER OF SEQ ID NOS: 18

<210> SEQ ID NO 1
<211> LENGTH: 1145
<212> TYPE: PRT
<213> ORGANISM: Artificial sequence
<220> FEATURE:
<223> OTHER INFORMATION: Synthetic Her2 v1 amino acid sequence

<400> SEQUENCE: 1

```
Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Arg Thr Phe Lys Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Ala Ala Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
        340                 345                 350

Val Arg Ala Val Thr Ser Ala Asn Ile Gln Glu Phe Ala Gly Cys Lys
    355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415
```

```
Asp Ser Leu Pro Asp Leu Ser Val Phe Gln Asn Leu Gln Val Ile Arg
            420             425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Ala Ala Asp Gln Cys Val Ala Cys Ala His Tyr Lys Asp
            580                 585                 590

Pro Pro Ala Cys Val Ala Arg Cys Pro Ser Gly Val Lys Pro Asp Leu
            595                 600                 605

Ser Tyr Met Pro Ile Trp Ala Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
            660                 665                 670

Ile Leu Ile Lys Arg Arg Gln Gln Lys Ile Arg Lys Tyr Thr Met Arg
        675                 680                 685

Arg Leu Leu Gln Glu Thr Glu Leu Val Glu Pro Leu Thr Pro Ser Gly
        690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Met Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
        770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
```

```
                  835                 840                 845
Arg Asn Val Leu Val Lys Ser Pro Asn His Val Lys Ile Thr Asp Phe
    850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
            915                 920                 925
Arg Glu Ile Pro Asp Leu Leu Glu Lys Gly Glu Arg Leu Pro Gln Pro
930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                965                 970                 975
Ser Arg Met Ala Arg Asp Pro Gln Arg Phe Val Val Ile Gln Asn Glu
            980                 985                 990
Asp Leu Gly Pro Ala Ser Pro Leu Asp Ser Thr Phe Tyr Arg Ser Leu
        995                 1000                1005
Leu Glu Asp Asp Asp Met Gly Asp Leu Val Asp Ala Glu Glu Ala
    1010                1015                1020
Leu Val Pro Gln Gln Gly Phe Phe Cys Pro Asp Pro Ala Pro Gly
    1025                1030                1035
Ala Gly Gly Met Val His His Arg His Arg Ser Ser Ser Thr Arg
    1040                1045                1050
Ser Gly Gly Gly Asp Leu Thr Leu Gly Leu Glu Pro Ser Glu Glu
    1055                1060                1065
Glu Ala Pro Arg Ser Pro Leu Ala Pro Ser Glu Gly Ala Gly Ser
    1070                1075                1080
Asp Val Phe Asp Gly Asp Leu Gly Met Gly Ala Ala Lys Gly Leu
    1085                1090                1095
Gln Ser Leu Pro Thr His Asp Pro Ser Pro Leu Gln Arg Tyr Ser
    1100                1105                1110
Glu Asp Pro Thr Val Pro Leu Pro Ser Glu Thr Asp Gly Tyr Val
    1115                1120                1125
Ala Pro Leu Thr Cys Ser Pro Gln Pro Glu Leu Gly Leu Asp Val
    1130                1135                1140
Pro Val
1145

<210> SEQ ID NO 2
<211> LENGTH: 3441
<212> TYPE: DNA
<213> ORGANISM: Artificial sequence
<220> FEATURE:
<223> OTHER INFORMATION: Synthetic Her2 v1 nucleotide sequence

<400> SEQUENCE: 2
atggaactgg ctgctctgtg tagatgggga ctgctgcttg ctctgttgcc tcctggagct      60
gcttctaccc aagtgtgcac aggcaccgac atgaagctga gactgcctgc ttctcctgag     120
acacacctgg acatgctgag acacctgtac caggatgtca ggtggtgcag ggaaatctg      180 gaactgacct acctgcctac caacgccagc ctgagctttc tgcaggacat ccaagaggtg     240
```

```
cagggatacg tgctgatcgc tcacaatcaa gtgagacagg tgccactgca gaggctgaga    300
atcgttagag gcacccagct gttcgaggac aactatgctc tggctgtgct ggacaatggc    360
gaccctctga caacaccac acctgtgaca ggagcttctc ctggtggact gagagaactg     420
cagctgagaa gcctgaccga gatcctgaaa ggaggagtgc tgatccagcg gaaccctcag    480
ctgtgctacc aggacaccat cctgtggaag gacatcttcc acaagaacaa ccagctggct    540
ctgacactga tcgacaccaa cagaagcaga gcctgccatc cttgctctcc catgtgcaag    600
ggctctagat gttggggaga gagcagcgag gattgccaga gcctgaccag aacagtgtgt    660 gctgaggat gtgccagatg caaaggacct ctgcctaccg actgctgcca cgagcaatgt     720
gcagctggat gtacaggacc aaagcactct gattgcctgg cctgcctgca cttcaaccac    780
tctggaatct gcgagctgca ctgtcctgct ctggtcacct acaacacacg gaccttcaag    840
agcatgccta atcctgaagg cagatacacc tttggagcca gctgtgtgac agcctgtcct    900
tacaactacc tgagcaccga cgtgggcagc tgcacactcg tttgtcctgc tgccaatcaa    960
gaagtgacag ccgaggacgg cacccagaga tgcgagaagt gtagcaagcc ttgcgctaga    1020
gtgtgttacg gactcggcat ggaacacctg agagaagtga gagccgtgac cagtgccaac    1080
atccaagagt ttgctggctg caagaagatc tttggcagcc tcgccttcct gcctgagagc    1140
ttcgatggcg atcctgccag caatactgct cctctgcagc ctgaacagct ccaggtgttc    1200
gagacactgg aagagatcac aggctacctg tacatcagcg catggccaga cagcctgcct    1260
gacctgtccg tgttccagaa cctgcaagtg atcagaggca gaatcctgca caacggagcc    1320
tattctctga ccctgcaagg cctgggaatc agctggctgg gactgagatc cctgagagag    1380
cttggatctg gcctggctct gatccaccac aatacccacc tgtgcttcgt gcacaccgtg    1440
ccttgggacc agctgtttcg gaatcctcat caggctctgc tgcacacagc caacagacct    1500
gaggatgagt gtgttggcga aggcctggct tgtcaccagc tctgtgctag aggacactgt    1560
tggggacctg gacctacaca gtgtgtgaac tgtagccagt tcctgagagg ccaagaatgc    1620
gtggaagagt gtagagttct gcagggactg cctcgcgagt acgtgaacgc tagacactgt    1680
ctgccttgtc atcccgagtg ccagcctcag aatggcagcg tgacatgttt tggaccagct    1740
gccgatcagt gcgtggcctg tgctcactat aaggaccctc cagcctgcgt ggccagatgt    1800
cctagcggag tgaagcctga cctgagctac atgcccatct gggcatttcc agatgaggaa    1860
ggagcttgcc agcccttgtcc tatcaactgc acccacagct gcgtggacct ggacgataag    1920
ggatgtccag ccgagcagag agcctctcca ctgacctcta tcatctctgc cgtcgtgggc    1980
atcctgctgg tggtggttct gggagttgtg ttcggcatcc tgatcaagag acggcagcag    2040
aagatccgga agtacaccat gcggagactg ctgcaagaga ctgagctggt ggaacctctg    2100
acacccagcg gagctatgcc taaccaggct cagatgcgga ttctgaaaga aaccgagctg    2160
cggaaagtga aggtgctcgg ctctggagcc tttggcacag tgtacaaagg catctggatc    2220
cctgacggag agaacgtgaa gattcctgtg gccatcatgg tgctgagaga gaacacaagt    2280
cccaaggcca acaaagagat cctggacgag gcctacgtga tggctggtgt tggcagccct    2340
tatgtgtcta actgctgggg catctgtctg accagcaccg tgcagctggt cactcagctg    2400
atgccttacg gctgcctgct ggatcacgtg agagagaata gaggcagact gggctctcag    2460
gacctgctga actggtgcat gcagatcgcc aagggcatga gctacctcga ggatgtgaga    2520
ctggtccaca gagatctggc tgccagaaac gtgctcgtga agtctcctaa ccacgtgaag    2580
```

| | |
|---|---|
| atcaccgact tcggactggc taggctgctg gatatcgacg agacagagta ccacgctgat | 2640 |
| ggaggcaagg tgcccatcaa gtggatggct ctggaatcca tcctgagacg gagattcacc | 2700 |
| caccagtccg atgtgtggtc ttacggagtg acagtgtggg agctgatgac cttcggagcc | 2760 |
| aagccttacg acggcatccc tgccagagag atcccagatc tgctggaaaa gggagagaga | 2820 |
| ctgcctcagc ctcctatctg caccatcgac gtgtacatga ttatggtcaa gtgttggatg | 2880 |
| atcgacagcg agtgcagacc cagattcaga gaactggtgt ccgagttctc tcggatggcc | 2940 |
| agagatcctc agagattcgt ggtcatccag aacgaggatc tgggacctgc cagccctctg | 3000 |
| gacagcacct tctacagatc cctgctggaa gatgacgaca tgggtgacct ggtggacgct | 3060 |
| gaagaagctc tggttcctca gcagggcttc ttctgccctg atcctgctcc aggagcaggt | 3120 |
| ggaatggtgc atcacagaca cagaagctcc agcaccagaa gcggaggcgg agatctgaca | 3180 |
| ctgggactcg agccatctga ggaagaggct cctagatctc tctggctcc ttctgaagga | 3240 |
| gctggaagcg acgttttcga cggagatctt ggaatgggag ctgccaaagg actccagtct | 3300 |
| ctgcccacac acgaccccatc tccactgcag agatacagcg aggaccctac cgtgcctctg | 3360 |
| ccaagcgaga cagatggata tgtggcacct ctgacctgct ctcctcagcc agaactggga | 3420 |
| cttgatgtgc ctgtttgatg a | 3441 |

<210> SEQ ID NO 3
<211> LENGTH: 427
<212> TYPE: PRT
<213> ORGANISM: Artificial sequence
<220> FEATURE:
<223> OTHER INFORMATION: Synthetic Brachyury amino acid sequence

<400> SEQUENCE: 3

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
            85                  90                  95

Ala Asp Asn His Arg Trp Lys Tyr Val Asn Gly Glu Trp Val Pro Gly
        100                 105                 110

Gly Lys Pro Glu Pro Gln Ala Pro Ser Cys Val Tyr Ile His Pro Asp
    115                 120                 125

Ser Pro Asn Phe Gly Ala His Trp Met Lys Ala Pro Val Ser Phe Ser
130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
            165                 170                 175

Gly Pro Gln Arg Met Ile Thr Ser His Cys Phe Pro Glu Thr Gln Phe
        180                 185                 190

Ile Ala Val Thr Ala Tyr Gln Asn Glu Glu Ile Thr Ala Leu Lys Ile
    195                 200                 205
```

```
Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
                260                 265                 270

Thr His Ser Cys Asp Arg Tyr Pro Thr Leu Arg Ser His Tyr Ala His
            275                 280                 285

Arg Asn Asn Ser Pro Thr Tyr Ser Asp Asn Ser Pro Ala Cys Leu Ser
    290                 295                 300

Met Leu Gln Ser His Asp Asn Trp Ser Ser Leu Gly Met Pro Ala His
305                 310                 315                 320

Pro Ser Met Leu Pro Val Ser His Asn Ala Ser Pro Pro Thr Ser Ser
                325                 330                 335

Ser Gln Tyr Pro Ser Leu Trp Ser Val Ser Asn Gly Ala Val Thr Pro
                340                 345                 350

Gly Ser Gln Ala Ala Ala Val Ser Asn Gly Leu Gly Ala Gln Phe Phe
                355                 360                 365

Arg Gly Ser Pro Ala His Tyr Thr Pro Leu Thr His Pro Val Ser Ala
    370                 375                 380

Pro Ser Ser Ser Gly Ser Pro Leu Tyr Glu Gly Ala Ala Ala Ala Thr
385                 390                 395                 400

Asp Ile Val Asp Ser Gln Tyr Asp Ala Ala Gln Gly Arg Leu Ile
                405                 410                 415

Ala Ser Trp Thr Pro Val Ser Pro Pro Ser Met
                420                 425

<210> SEQ ID NO 4
<211> LENGTH: 1287
<212> TYPE: DNA
<213> ORGANISM: Artificial sequence
<220> FEATURE:
<223> OTHER INFORMATION: Synthetic Brachyury nucleotide sequence

<400> SEQUENCE: 4
atgtctagcc ctggcacaga gtctgctggc aagagcctcc agtacagagt ggaccatctg      60
ctgagcgctg tggagaatga actgcaggct ggaagcgaga agggagatcc tacagaaaga     120
gagctgagag tcggactgga agagtccgag ctgtggctgc ggttcaaaga actgaccaac     180
gagatgatcg tgaccaagaa cggcagacgg atgttccctg tgctgaaagt gaacgtgtcc     240
ggactggacc ctaacgccat gtacagcttt ctgctggatt tcgtggcagc tgacaaccac     300
agatggaagt acgtgaacgg agagtgggtg ccaggaggaa aacctgaacc tcaggctcct     360
agctgcgtgt acattcaccc tgacagccct aacttcggag cccactggat gaaggctcct     420
gtgtccttca gcaaagtgaa gctgaccaac aagctgaacg gagaggcca gatcatgctg     480 aacagcctgc acaagtatga gcctaggatc acatcgtca gagttggagg ccctcagcgg     540
atgatcacca gccactgttt ccctgagaca cagttcatcg cagtgaccgc ttaccagaac     600
gaggaaatca gccctgaa gatcaagtac aatcccttcg ccaaggcctt cctggacgcc     660
aaagagcgga gcgaccacaa agaaatgatg aagaacctg gcgacagcca gcagcctggc     720
tattctcaat ggggatggct gctgccaggc acctccacat gtgccctcc agccaatcct     780 catcctcagt ttggcggagc cctgagcctg cctagcacac acagctgcga cagatacct     840
```

-continued

```
acactgagaa gccactacgc tcacagaaac aacagccta cctacagcga caatagccct        900
gcctgtctga gcatgctgca gtcccacgac aattggtcca gctgggaat gcctgctcac        960 ccttctatgc tgcctgtctc tcacaacgcc tctccaccta caagcagctc tcagtaccct      1020
agcctttgga gcgtgtccaa tggagctgtg acacctggat ctcaggctgc cgctgtgtct      1080
aatggactgg gagcccagtt cttcagaggc agccctgctc actacacacc tctgacacat      1140
ccagtgtctg ctcctagcag cagcggaagc cctctctatg aaggagccgc tgcagccacc      1200
gacatcgtgg attctcagta tgatgctgcc gcacagggca gactgatcgc ctcttggaca      1260
cctgtgagcc caccttccat gtgatga                                          1287
```

<210> SEQ ID NO 5
<211> LENGTH: 435
<212> TYPE: PRT
<213> ORGANISM: Homo sapiens
<220> FEATURE:
<223> OTHER INFORMATION: Brachyury protein Isoform 1 from GenBank
      Accession No. O15178.1

<400> SEQUENCE: 5

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Leu Cys Pro
                245                 250                 255

Pro Ala Asn Pro His Pro Gln Phe Gly Gly Ala Leu Ser Leu Pro Ser
            260                 265                 270
```

```
Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
        290                 295                 300

Asp Asn Ser Pro Ala Cys Leu Ser Met Leu Gln Ser His Asp Asn Trp
305                 310                 315                 320

Ser Ser Leu Gly Met Pro Ala His Pro Ser Met Leu Pro Val Ser His
                325                 330                 335

Asn Ala Ser Pro Pro Thr Ser Ser Ser Gln Tyr Pro Ser Leu Trp Ser
                340                 345                 350

Val Ser Asn Gly Ala Val Thr Pro Gly Ser Gln Ala Ala Ala Val Ser
        355                 360                 365

Asn Gly Leu Gly Ala Gln Phe Phe Arg Gly Ser Pro Ala His Tyr Thr
370                 375                 380

Pro Leu Thr His Pro Val Ser Ala Pro Ser Ser Ser Gly Ser Pro Leu
385                 390                 395                 400

Tyr Glu Gly Ala Ala Ala Ala Thr Asp Ile Val Asp Ser Gln Tyr Asp
                405                 410                 415

Ala Ala Ala Gln Gly Arg Leu Ile Ala Ser Trp Thr Pro Val Ser Pro
        420                 425                 430

Pro Ser Met
        435

<210> SEQ ID NO 6
<211> LENGTH: 1308
<212> TYPE: DNA
<213> ORGANISM: Homo sapiens
<220> FEATURE:
<223> OTHER INFORMATION: Coding sequence for Brachyury protein Isoform 1
      GenBank Accession No. 015178.1

<400> SEQUENCE: 6
atgagcagcc ctggcacaga gagcgccggc aagagcctgc agtaccgggt ggaccatctg      60
ctgagcgccg tggagaatga gctgcaggcc ggctccgaga agggcgaccc caccgagagg     120
gaactgagag tgggcctgga agagtccgag ctgtggctgc ggttcaaaga actgaccaac     180
gagatgatcg tgaccaagaa cggcagacgg atgttccccg tgctgaaagt gaacgtgtcc     240
ggcctggacc ccaacgccat gtacagcttt ctgctggact cgtggccgc cgacaaccac     300 aggtggaaat acgtgaacgg cgagtgggtg ccaggcggca acctgagcc tcaggccccc     360 agctgcgtgt acatccaccc cgacagcccc aatttcggcg cccactggat gaaggccccc     420
gtgtccttca gcaaagtgaa gctgaccaac aagctgaacg gcggaggcca gatcatgctg     480
aacagcctgc acaagtacga gccccggatc cacattgtgc gcgtgggcgg accccagaga     540
atgatcacca gccactgctt ccccgagaca cagtttatcg ccgtgaccgc ctaccagaac     600
gaggaaatca ccgccctgaa gatcaagtac aaccccttcg ccaaggcctt cctggacgcc     660
aaagagcgga gcgaccacaa agaaatgatg gaagaacccg gcgacagcca gcagcctggc     720
tacagccagt ggggctggct gctgccaggc acctccactc tgtgcccccc tgccaaccct     780
cacccctcag tcggcggagc cctgagcctg cctagcacac acagctgcga cagatacccc     840
accctgcgga gccacagaag cagcccctac cccagcccat acgccaccg gaacaacagc     900 cccacctaca gcgacaactc ccccgcctgc ctgagcatgc tgcagagcca cgacaactgg     960
tccagcctgg gcatgcctgc ccaccctagc atgctgcccg tgtccacaa tgccagcccc    1020 cctaccagca gctcccagta ccctagcctg tggagcgtgt ccaatggcgc cgtgacacct    1080
```

```
ggatctcagg ccgctgccgt gagcaatggc ctgggagccc agttctttag aggcagccct  1140
gcccactaca cccctctgac ccaccctgtg tccgcccta gctccagcgg cagccctctg   1200
tatgaaggcg ccgctgcagc caccgatatc gtggacagcc agtacgatgc cgccgctcag  1260
ggcagactga tcgccagctg gacccccgtg tctccccca gcatgtga              1308
```

```
<210> SEQ ID NO 7
<211> LENGTH: 435
<212> TYPE: PRT
<213> ORGANISM: Artificial sequence
<220> FEATURE:
<223> OTHER INFORMATION: Brachyury protein Isoform 1 (L254V)

<400> SEQUENCE: 7
```

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
                20                  25                  30

Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
    50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Tyr Gln Asn Glu Glu Ile Thr Ala Leu Lys Ile
        195                 200                 205

Lys Tyr Asn Pro Phe Ala Lys Ala Phe Leu Asp Ala Lys Glu Arg Ser
    210                 215                 220

Asp His Lys Glu Met Met Glu Glu Pro Gly Asp Ser Gln Gln Pro Gly
225                 230                 235                 240

Tyr Ser Gln Trp Gly Trp Leu Leu Pro Gly Thr Ser Thr Val Cys Pro
                245                 250                 255

Pro Ala Asn Pro His Pro Gln Phe Gly Gly Ala Leu Ser Leu Pro Ser
            260                 265                 270

Thr His Ser Cys Asp Arg Tyr Pro Thr Leu Arg Ser His Arg Ser Ser
        275                 280                 285

Pro Tyr Pro Ser Pro Tyr Ala His Arg Asn Asn Ser Pro Thr Tyr Ser
    290                 295                 300

Asp Asn Ser Pro Ala Cys Leu Ser Met Leu Gln Ser His Asp Asn Trp
305                 310                 315                 320
```

```
Ser Ser Leu Gly Met Pro Ala His Pro Ser Met Leu Pro Val Ser His
            325                 330                 335
Asn Ala Ser Pro Pro Thr Ser Ser Gln Tyr Pro Ser Leu Trp Ser
        340                 345                 350
Val Ser Asn Gly Ala Val Thr Pro Gly Ser Gln Ala Ala Val Ser
        355                 360                 365
Asn Gly Leu Gly Ala Gln Phe Phe Arg Gly Ser Pro Ala His Tyr Thr
370                 375                 380
Pro Leu Thr His Pro Val Ser Ala Pro Ser Ser Ser Gly Ser Pro Leu
385                 390                 395                 400
Tyr Glu Gly Ala Ala Ala Thr Asp Ile Val Asp Ser Gln Tyr Asp
            405                 410                 415
Ala Ala Ala Gln Gly Arg Leu Ile Ala Ser Trp Thr Pro Val Ser Pro
            420                 425                 430
Pro Ser Met
    435
```

<210> SEQ ID NO 8
<211> LENGTH: 1308
<212> TYPE: DNA
<213> ORGANISM: Artificial sequence
<220> FEATURE:
<223> OTHER INFORMATION: Coding sequence encoding Brachyury protein Isoform 1 with L254V

<400> SEQUENCE: 8

```
atgagctccc ctggcaccga gagcgcggga aagagcctgc agtaccgagt ggaccacctg      60
ctgagcgccg tggagaatga gctgcaggcg ggcagcgaga agggcgaccc cacagagcgc     120
gaactgcgcg tgggcctgga ggagagcgag ctgtggctgc gcttcaagga gctcaccaat     180
gagatgatcg tgaccaagaa cggcaggagg atgtttccgg tgctgaaggt gaacgtgtct     240
ggcctggacc ccaacgccat gtactccttc ctgctggact cgtggcggc ggacaaccac     300
cgctggaagt acgtgaacgg ggaatgggtg ccggggggca gccggagcc gcaggcgccc     360
agctgcgtct acatccaccc cgactcgccc aacttcgggg cccactggat gaaggctccc     420
gtctccttca gcaaagtcaa gctcaccaac aagctcaacg gaggggggcca gatcatgctg     480
aactccttgc ataagtatga gcctcgaatc cacatagtga gagttggggg tccacagcgc     540
atgatcacca gccactgctt ccctgagacc cagttcatag cggtgactgc ttatcagaac     600
gaggagatca gctcttaa aattaagtac aatccatttg caaaggcttt ccttgatgca     660
aaggaaagaa gtgatcacaa agagatgatg gaggaacccg gagacagcca gcaacctggg     720
tactcccaat gggggtggct tcttcctgga accagcaccg tttgtccacc tgcaaatcct     780
catcctcagt ttggaggtgc cctctcccct ccctccacgc acagctgtga caggtaccca     840
accctgagga gccaccggtc ctcacccta cccagcccct atgctcatcg gaacaattct     900
ccaacctatt ctgacaactc acctgcatgt ttatccatgc tgcaatccca tgacaattgg     960
tccagccttg gaatgcctgc ccatcccagc atgctccccg tgagccacaa tgccagccca    1020
cctaccagct ccagtcagta ccccagcctg tggtctgtga caacggcgc cgtcaccccg    1080
ggctcccagg cagcagccgt gtccaacggg ctggggcc agttcttccg gggctccccc    1140
gcgcactaca caccctcac ccatccggtc tcggcgccct cttcctcggg atccccactg    1200
tacgaagggg cggccgcggc cacagacatc gtggacagcc agtacgacgc cgcagcccaa    1260
ggccgcctca tagcctcatg gacacctgtg tcgccacctt ccatgtga                 1308
```

<210> SEQ ID NO 9
<211> LENGTH: 449
<212> TYPE: PRT
<213> ORGANISM: Artificial sequence
<220> FEATURE:
<223> OTHER INFORMATION: Brachyury-I3 fusion protein

<400> SEQUENCE: 9

| | | | | | | | | | | | | | | | |
|---|---|---|---|---|---|---|---|---|---|---|---|---|---|---|---|
| Met | Lys | Asn | Asn | Leu | Tyr | Glu | Glu | Lys | Met | Asn | Met | Ser | Lys | Lys | Ser |
| 1 | | | | 5 | | | | | 10 | | | | | 15 | |
| Ser | Pro | Gly | Thr | Glu | Ser | Ala | Gly | Lys | Ser | Leu | Gln | Tyr | Arg | Val | Asp |
| | | | 20 | | | | | 25 | | | | | 30 | | |
| His | Leu | Leu | Ser | Ala | Val | Glu | Asn | Glu | Leu | Gln | Ala | Gly | Ser | Glu | Lys |
| | | 35 | | | | | 40 | | | | | 45 | | | |
| Gly | Asp | Pro | Thr | Glu | Arg | Glu | Leu | Arg | Val | Gly | Leu | Glu | Glu | Ser | Glu |
| | 50 | | | | | 55 | | | | | 60 | | | | |
| Leu | Trp | Leu | Arg | Phe | Lys | Glu | Leu | Thr | Asn | Glu | Met | Ile | Val | Thr | Lys |
| 65 | | | | | 70 | | | | | 75 | | | | | 80 |
| Asn | Gly | Arg | Arg | Met | Phe | Pro | Val | Leu | Lys | Val | Asn | Val | Ser | Gly | Leu |
| | | | | 85 | | | | | 90 | | | | | 95 | |
| Asp | Pro | Asn | Ala | Met | Tyr | Ser | Phe | Leu | Leu | Asp | Phe | Val | Ala | Ala | Asp |
| | | | 100 | | | | | 105 | | | | | 110 | | |
| Asn | His | Arg | Trp | Lys | Tyr | Val | Asn | Gly | Glu | Trp | Val | Pro | Gly | Gly | Lys |
| | | 115 | | | | | 120 | | | | | 125 | | | |
| Pro | Glu | Pro | Gln | Ala | Pro | Ser | Cys | Val | Tyr | Ile | His | Pro | Asp | Ser | Pro |
| | 130 | | | | | 135 | | | | | 140 | | | | |
| Asn | Phe | Gly | Ala | His | Trp | Met | Lys | Ala | Pro | Val | Ser | Phe | Ser | Lys | Val |
| 145 | | | | | 150 | | | | | 155 | | | | | 160 |
| Lys | Leu | Thr | Asn | Lys | Leu | Asn | Gly | Gly | Gly | Gln | Ile | Met | Leu | Asn | Ser |
| | | | | 165 | | | | | 170 | | | | | 175 | |
| Leu | His | Lys | Tyr | Glu | Pro | Arg | Ile | His | Ile | Val | Arg | Val | Gly | Gly | Pro |
| | | | 180 | | | | | 185 | | | | | 190 | | |
| Gln | Arg | Met | Ile | Thr | Ser | His | Cys | Phe | Pro | Glu | Thr | Gln | Phe | Ile | Ala |
| | | 195 | | | | | 200 | | | | | 205 | | | |
| Val | Thr | Ala | Tyr | Gln | Asn | Glu | Glu | Ile | Thr | Ala | Leu | Lys | Ile | Lys | Tyr |
| | 210 | | | | | 215 | | | | | 220 | | | | |
| Asn | Pro | Phe | Ala | Lys | Ala | Phe | Leu | Asp | Ala | Lys | Glu | Arg | Ser | Asp | His |
| 225 | | | | | 230 | | | | | 235 | | | | | 240 |
| Lys | Glu | Met | Met | Glu | Glu | Pro | Gly | Asp | Ser | Gln | Gln | Pro | Gly | Tyr | Ser |
| | | | | 245 | | | | | 250 | | | | | 255 | |
| Gln | Trp | Gly | Trp | Leu | Leu | Pro | Gly | Thr | Ser | Thr | Val | Cys | Pro | Pro | Ala |
| | | | 260 | | | | | 265 | | | | | 270 | | |
| Asn | Pro | His | Pro | Gln | Phe | Gly | Gly | Ala | Leu | Ser | Leu | Pro | Ser | Thr | His |
| | | 275 | | | | | 280 | | | | | 285 | | | |
| Ser | Cys | Asp | Arg | Tyr | Pro | Thr | Leu | Arg | Ser | His | Arg | Ser | Ser | Pro | Tyr |
| | 290 | | | | | 295 | | | | | 300 | | | | |
| Pro | Ser | Pro | Tyr | Ala | His | Arg | Asn | Asn | Ser | Pro | Thr | Tyr | Ser | Asp | Asn |
| 305 | | | | | 310 | | | | | 315 | | | | | 320 |
| Ser | Pro | Ala | Cys | Leu | Ser | Met | Leu | Gln | Ser | His | Asp | Asn | Trp | Ser | Ser |
| | | | | 325 | | | | | 330 | | | | | 335 | |
| Leu | Gly | Met | Pro | Ala | His | Pro | Ser | Met | Leu | Pro | Val | Ser | His | Asn | Ala |
| | | | 340 | | | | | 345 | | | | | 350 | | |
| Ser | Pro | Pro | Thr | Ser | Ser | Ser | Gln | Tyr | Pro | Ser | Leu | Trp | Ser | Val | Ser |
| | | 355 | | | | | 360 | | | | | 365 | | | |

```
Asn Gly Ala Val Thr Pro Gly Ser Gln Ala Ala Val Ser Asn Gly
        370                 375                 380

Leu Gly Ala Gln Phe Phe Arg Gly Ser Pro Ala His Tyr Thr Pro Leu
385                 390                 395                 400

Thr His Pro Val Ser Ala Pro Ser Ser Gly Ser Pro Leu Tyr Glu
                405                 410                 415

Gly Ala Ala Ala Ala Thr Asp Ile Val Asp Ser Gln Tyr Asp Ala Ala
                    420                 425                 430

Ala Gln Gly Arg Leu Ile Ala Ser Trp Thr Pro Val Ser Pro Pro Ser
            435                 440                 445

Met
```

<210> SEQ ID NO 10
<211> LENGTH: 1350
<212> TYPE: DNA
<213> ORGANISM: Artificial sequence
<220> FEATURE:
<223> OTHER INFORMATION: Coding sequence encoding I3 Brachyury fusion
      protein of SEQ ID NO 9

<400> SEQUENCE: 10

```
atgaaaaata acttgtatga agaaaaaatg aacatgagta agaaaagctc ccctggcacc      60
gagagcgcgg gaaagagcct gcagtaccga gtggaccacc tgctgagcgc cgtggagaat     120
gagctgcagg cgggcagcga gaagggcgac cccacagagc gcgaactgcg cgtgggcctg     180
gaggagagcg agctgtggct gcgcttcaag gagctcacca atgagatgat cgtgaccaag     240
aacggcagga ggatgtttcc ggtgctgaag gtgaacgtgt ctggcctgga ccccaacgcc     300
atgtactcct tcctgctgga cttcgtggcg gcggacaacc accgctggaa gtacgtgaac     360
ggggaatggg tgccgggggg caagccgaga ccgcaggcgc ccagctgcgt ctacatccac     420
cccgactcgc ccaacttcgg ggcccactgg atgaaggctc ccgtctcctt cagcaaagtc     480
aagctcacca acaagctcaa cggagggggc cagatcatgc tgaactcctt gcataagtat     540
gagcctcgaa tccacatagt gagagttggg ggtccacagc gcatgatcac cagccactgc     600
ttccctgaga cccagttcat agcggtgact gcttatcaga acgaggagat cacagctctt     660
aaaattaagt acaatccatt tgcaaaggct ttccttgatg caaaggaaag aagtgatcac     720
aaagagatga tggaggaacc cggagacagc cagcaacctg gtactcccca tggggtggt     780
cttcttcctg gaaccagcac cgtttgtcca cctgcaaatc ctcatcctca gtttggaggt     840
gccctctccc tccctccac gcacagctgt gacaggtacc caaccctgag gagccaccgg     900
tcctcaccct accccagccc ctatgctcat cggaacaatt ctccaaccta ttctgacaac     960
tcacctgcat gtttatccat gctgcaatcc atgacaatt ggtccagcct tggaatgcct    1020
gcccatccca gcatgctccc cgtgagccac aatgccagcc acctaccag ctccagtcag    1080
taccccagcc tgtggtctgt gagcaacggc ccgtcaccc cgggctccca ggcagcagcc    1140
gtgtccaacg gctgggggc ccagttcttc cggggctccc ccgcgcacta cacccctc     1200
acccatccgg tctcggcgcc ctcttcctcg ggatcccac tgtacgaagg ggcggccgcg    1260
gccacagaca tcgtggacag ccagtacgac gccgcagccc aaggccgcct catagcctca    1320
tggacacctg tgtcgccacc ttccatgtga                                    1350
```

<210> SEQ ID NO 11
<211> LENGTH: 261
<212> TYPE: PRT
<213> ORGANISM: Homo sapiens
<220> FEATURE:
<223> OTHER INFORMATION: hCD40L from NCBI RefSeq NP_000065.1.

<400> SEQUENCE: 11

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
            20                  25                  30

Ile Thr Gln Met Ile Gly Ser Ala Leu Phe Ala Val Tyr Leu His Arg
        35                  40                  45

Arg Leu Asp Lys Ile Glu Asp Glu Arg Asn Leu His Glu Asp Phe Val
    50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
    130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
    210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260
```

<210> SEQ ID NO 12
<211> LENGTH: 789
<212> TYPE: DNA
<213> ORGANISM: Homo sapiens
<220> FEATURE:
<223> OTHER INFORMATION: hCD40L from NCBI RefSeq NP_000065.1.

<400> SEQUENCE: 12

```
atgatcgaga catacaacca gacaagccct agaagcgccg ccacaggact gcctatcagc    60
atgaagatct tcatgtacct gctgaccgtg ttcctgatca cccagatgat cggcagcgcc   120
ctgtttgccg tgtacctgca cagacggctg acaagatcg aggacgagag aaacctgcac   180
gaggacttcg tgttcatgaa gaccatccag cggtgcaaca ccggcgagag aagtctgagc   240
ctgctgaact gcgaggaaat caagagccag ttcgagggct tcgtgaagga catcatgctg   300
aacaaagagg aaacgaagaa agagaactcc ttcgagatgc agaagggcga ccagaatcct   360
cagatcgccg ctcacgtgat cagcgaggcc agcagcaaga acaacaagcgt gctgcagtgg   420
```

```
gccgagaagg gctactacac catgagcaac aacctggtca ccctggagaa cggcaagcag    480
ctgacagtga agcggcaggg cctgtactac atctacgccc aagtgacctt ctgcagcaac    540
agagaggcca gctctcaggc tcctttcatc gccagcctgt gcctgaagtc tcctggcaga    600
ttcgagcgga ttctgctgag agccgccaac acacacagca gcgccaaacc ttgtggccag    660
cagtctattc acctcggcgg agtgtttgag ctgcagcctg gcgcaagcgt gttcgtgaat    720
gtgacagacc ctagccaggt gtcccacggc accggcttta catctttcgg actgctgaag    780
ctgtgatga                                                             789

<210> SEQ ID NO 13
<211> LENGTH: 1145
<212> TYPE: PRT
<213> ORGANISM: Artificial sequence
<220> FEATURE:
<223> OTHER INFORMATION: Synthetic Her2 v2 amino acid sequence

<400> SEQUENCE: 13

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu Ala Cys Pro Ala Leu Val
            260                 265                 270

Thr Tyr Asn Thr Arg Thr Ala Lys Ser Met Pro Asn Pro Glu Gly Arg
        275                 280                 285
```

```
Tyr Thr Phe Gly Ala Ser Cys Val Thr Ala Cys Pro Tyr Asn Tyr Leu
290                 295                 300

Ser Thr Asp Ala Gly Ala Cys Thr Leu Val Cys Pro Ala Ala Asn Gln
305                 310                 315                 320

Glu Val Thr Ala Glu Asp Gly Thr Gln Arg Cys Glu Ala Cys Ser Lys
                325                 330                 335

Ala Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Ala Ala Asp Gln Cys Val Ala Cys Ala His Tyr Lys Asp
                580                 585                 590

Pro Pro Ala Cys Val Ala Arg Cys Pro Ser Gly Val Lys Pro Asp Leu
                595                 600                 605

Ser Tyr Met Pro Ile Trp Ala Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Ile Ser
                645                 650                 655

Ala Val Val Gly Ile Leu Leu Val Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
```

```
            705                 710                 715                 720
Arg Lys Val Lys Val Leu Gly Ser Gly Ala Phe Gly Thr Val Tyr Lys
                    725                 730                 735
Gly Ile Trp Ile Pro Asp Gly Glu Asn Val Lys Ile Pro Val Ala Ile
                    740                 745                 750
Met Val Leu Arg Glu Asn Thr Ser Pro Lys Ala Asn Lys Glu Ile Leu
                    755                 760                 765
Asp Glu Ala Tyr Val Met Ala Gly Val Gly Ser Pro Tyr Val Ser Arg
                    770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
                    805                 810                 815
Leu Gly Ser Gln Asp Leu Leu Asn Trp Cys Met Gln Ile Ala Lys Gly
                    820                 825                 830
Met Ser Tyr Leu Glu Asp Val Arg Leu Val His Arg Asp Leu Ala Ala
                    835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
                    885                 890                 895
Arg Arg Phe Thr His Gln Ser Asp Val Trp Ser Tyr Gly Val Thr Val
                    900                 905                 910
Trp Glu Leu Met Thr Phe Gly Ala Lys Pro Tyr Asp Gly Ile Pro Ala
                    915                 920                 925
Arg Glu Ile Pro Asp Leu Leu Glu Lys Gly Glu Arg Leu Pro Gln Pro
                    930                 935                 940
Pro Ile Cys Thr Ile Asp Val Tyr Met Ile Met Val Lys Cys Trp Met
945                 950                 955                 960
Ile Asp Ser Glu Cys Arg Pro Arg Phe Arg Glu Leu Val Ser Glu Phe
                    965                 970                 975
Ser Arg Met Ala Arg Asp Pro Gln Arg Phe Val Val Ile Gln Asn Glu
                    980                 985                 990
Asp Leu Gly Pro Ala Ser Pro Leu Asp Ser Thr Phe Tyr Arg Ser Leu
                    995                 1000                1005
Leu Glu Asp Asp Asp Met Gly Asp Leu Val Asp Ala Glu Glu Ala
                    1010                1015                1020
Leu Val Pro Gln Gln Gly Phe Phe Cys Pro Asp Pro Ala Pro Gly
                    1025                1030                1035
Ala Gly Gly Met Val His His Arg His Arg Ser Ser Ser Thr Arg
                    1040                1045                1050
Ser Gly Gly Gly Asp Leu Thr Leu Gly Leu Glu Pro Ser Glu Glu
                    1055                1060                1065
Glu Ala Pro Arg Ser Pro Leu Ala Pro Ser Glu Gly Ala Gly Ser
                    1070                1075                1080
Asp Val Phe Asp Gly Asp Leu Gly Met Gly Ala Ala Lys Gly Leu
                    1085                1090                1095
Gln Ser Leu Pro Thr His Asp Pro Ser Pro Leu Gln Arg Tyr Ser
                    1100                1105                1110
Glu Asp Pro Thr Val Pro Leu Pro Ser Glu Thr Asp Gly Tyr Val
                    1115                1120                1125
```

Ala Pro Leu Thr Cys Ser Pro Gln Pro Glu Leu Gly Leu Asp Val
    1130                1135                1140
Pro Val
    1145

<210> SEQ ID NO 14
<211> LENGTH: 3441
<212> TYPE: DNA
<213> ORGANISM: Artificial sequence
<220> FEATURE:
<223> OTHER INFORMATION: Synthetic Her2 v2 nucleotide sequence

<400> SEQUENCE: 14

| | | | | | | |
|---|---|---|---|---|---|---|
| atggaactgg | ctgctctgtg | tagatgggga | ctgctgcttg | ctctgttgcc | tcctggagct | 60 |
| gcttctaccc | aagtgtgcac | aggcaccgac | atgaagctga | actgcctgc | ttctcctgag | 120 |
| acacacctgg | acatgctgag | acacctgtac | cagggatgtc | aggtggtgca | gggaaatctg | 180 |
| gaactgacct | acctgcctac | caacgccagc | ctgagctttc | tgcaggacat | ccaagaggtg | 240 |
| cagggatacg | tgctgatcgc | tcacaatcaa | gtgagacagg | tgccactgca | gaggctgaga | 300 |
| atcgttagag | caccagct | gttcgaggac | aactatgctc | tggctgtgct | ggacaatggc | 360 |
| gaccctctga | caacaccac | acctgtgaca | ggagcttctc | ctggtggact | gagagaactg | 420 |
| cagctgagaa | gcctgaccga | gatcctgaaa | ggaggagtgc | tgatccagcg | gaaccctcag | 480 |
| ctgtgctacc | aggacaccat | cctgtggaag | gacatcttcc | acaagaacaa | ccagctggct | 540 |
| ctgacactga | tcgacaccaa | cagaagcaga | gcctgccatc | cttgctctcc | catgtgcaag | 600 |
| ggctctagat | gttggggaga | gagcagcgag | gattgccaga | gcctgaccag | aacagtgtgt | 660 |
| gctggaggat | gtgccagatg | caaaggacct | ctgcctaccg | actgctgcca | cgagcaatgt | 720 |
| gcagctggat | gtacaggacc | aaagcactct | gattgcctgg | cctgcctgca | cttcaaccac | 780 |
| tctggaatct | gcgagctcgc | ctgtcctgct | ctggtcacct | acaacacacg | gaccgccaag | 840 |
| agcatgccta | tcctgaagg | cagatacacc | tttggagcca | gctgtgtgac | agcctgtcct | 900 |
| tacaactacc | tgagcaccga | cgctggagcc | tgcacactcg | tttgtcctgc | tgccaatcaa | 960 |
| gaagtgacgg | ccgaggacgg | cacccagaga | tgcgaggcct | gtagcaaggc | ttgcgctaga | 1020 |
| gtgtgttacg | gactcggcat | ggaacacctg | agagaagtga | gagccgtgac | cagtgccaac | 1080 |
| atccaagagt | ttgctggctg | caagaagatc | tttggcagcc | tcgccttcct | gcctgagagc | 1140 |
| ttcgatggcg | atcctgccag | caatactgct | cctctgcagc | ctgaacagct | ccaggtgttc | 1200 |
| gagacactgg | aagagatcac | aggctacctg | tacatcagcg | catggccaga | cagcctgcct | 1260 |
| gacctgtccg | tgttccagaa | cctgcaagtg | atcagaggca | gaatcctgca | caacggagcc | 1320 |
| tattctctga | ccctgcaagg | cctgggaatc | agctggctgg | gactgagatc | cctgagagag | 1380 |
| cttggatctg | gcctggctct | gatccaccac | aatacccacc | tgtgcttcgt | gcacaccgtg | 1440 |
| ccttgggacc | agctgtttcg | gaatcctcat | caggctctgc | tgcacacagc | caacagacct | 1500 |
| gaggatgagt | gtgttggcga | aggcctggct | tgtcaccagc | tctgtgctag | aggacactgt | 1560 |
| tgggacctg | gacctacaca | gtgtgtgaac | tgtagccagt | tcctgagagg | ccaagaatgc | 1620 |
| gtggaagagt | gtagagttct | gcagggactg | cctcgcgagt | acgtgaacgc | tagacactgt | 1680 |
| ctgccttgtc | atcccgagtg | ccagcctcag | aatggcagcg | tgacatgttt | tggaccagct | 1740 |
| gccgatcagt | gcgtggcctg | tgctcactat | aaggaccctc | cagcctgcgt | ggccagatgt | 1800 |
| cctagcggag | tgaagcctga | cctgagctac | atgcccatct | gggcatttcc | agatgaggaa | 1860 |

| | |
|---|---|
| ggagcttgcc agccttgtcc tatcaactgc acccacagct gcgtggacct ggacgataag | 1920 |
| ggatgtccag ccgagcagag agcctctcca ctgacctcta tcatctctgc cgtcgtgggc | 1980 |
| atcctgctgg tggtggttct gggagttgtg ttcggcatcc tgatcaagag acggcagcag | 2040 |
| aagatccgga agtacaccat gcggagactg ctgcaagaga ctgagctggt ggaacctctg | 2100 |
| acacccagcg gagctatgcc taaccaggct cagatgcgga ttctgaaaga aaccgagctg | 2160 |
| cggaaagtga aggtgctcgg ctctggagcc tttggcacag tgtacaaagg catctggatc | 2220 |
| cctgacggag agaacgtgaa gattcctgtg gccatcatgg tgctgagaga aaacacaagt | 2280 |
| cccaaggcca acaaagagat cctggacgag gcctacgtga tggctggtgt tggcagccct | 2340 |
| tatgtgtcta gactgctggg catctgtctg accagcaccg tgcagctggt cactcagctg | 2400 |
| atgccttacg gctgcctgct ggatcacgtg agagagaata gaggcagact gggctctcag | 2460 |
| gacctgctga actggtgcat gcagatcgcc aagggcatga gctacctcga ggatgtgaga | 2520 |
| ctggtccaca gagatctggc tgccagaaac gtgctcgtga agtctcctaa ccacgtgaag | 2580 |
| atcaccgact tcggactggc taggctgctg gatatcgacg agacagagta ccacgctgat | 2640 |
| ggaggcaagg tgcccatcaa gtggatggct ctggaatcca tcctgagacg gagattcacc | 2700 |
| caccagtccg atgtgtggtc ttacggagtg acagtgtggg agctgatgac cttcggagcc | 2760 |
| aagccttacg acggcatccc tgccagagag atcccagatc tgctggaaaa gggagagaga | 2820 |
| ctgcctcagc ctcctatctg caccatcgac gtgtacatga ttatggtcaa gtgttggatg | 2880 |
| atcgacagcg agtgcagacc cagattcaga gaactggtgt ccgagttctc tcggatggcc | 2940 |
| agagatcctc agagattcgt ggtcatccag aacgaggatc tgggacctgc agccctctg | 3000 |
| gacagcacct tctacagatc cctgctggaa gatgacgaca tgggtgacct ggtggacgct | 3060 |
| gaagaagctc tggttcctca gcagggcttc ttctgccctg atcctgctcc aggagcaggt | 3120 |
| ggaatggtgc atcacagaca cagaagctcc agcaccagaa gcggaggcgg agatctgaca | 3180 |
| ctgggactcg agccatctga ggaagaggct cctagatctc ctctggctcc ttctgaagga | 3240 |
| gctggaagcg acgttttcga cggagatctt ggaatgggag ctgccaaagg actccagtct | 3300 |
| ctgcccacac acgaccccat tccactgcag agatacagcg aggaccctac cgtgcctctg | 3360 |
| ccaagcgaga cagatggata tgtggcacct ctgacctgct ctcctcagcc agaactggga | 3420 |
| cttgatgtgc ctgtttgatg a | 3441 |

<210> SEQ ID NO 15
<211> LENGTH: 205
<212> TYPE: PRT
<213> ORGANISM: Artificial sequence
<220> FEATURE:
<223> OTHER INFORMATION: Synthetic Twist amino acid sequence

<400> SEQUENCE: 15

Met Gln Asp Val Ser Ser Ser Pro Val Ser Pro Ala Asp Asp Ser Leu
1               5                   10                  15

Ser Asn Ser Glu Glu Glu Pro Asp Arg Gln Gln Pro Ala Ser Gly Lys
            20                  25                  30

Arg Gly Ala Arg Lys Arg Arg Ser Ser Arg Arg Ser Ala Gly Gly Ser
        35                  40                  45

Ala Gly Pro Gly Gly Ala Thr Gly Gly Gly Ile Gly Gly Gly Asp Glu
    50                  55                  60

Pro Gly Ser Pro Ala Gln Gly Lys Arg Gly Lys Lys Ser Ala Gly Gly
65                  70                  75                  80

Gly Gly Gly Gly Gly Ala Gly Gly Gly Gly Gly Gly Ser
                85                  90                  95

Ser Ser Gly Gly Gly Ser Pro Gln Ser Tyr Glu Glu Leu Gln Thr Gln
            100                 105                 110

Arg Val Met Ala Asn Val Arg Glu Arg Gln Arg Thr Gln Ser Leu Asn
            115                 120                 125

Glu Ala Phe Ala Ala Leu Arg Lys Ile Ile Pro Thr Leu Pro Ser Asp
130                 135                 140

Lys Leu Ser Lys Ile Gln Thr Leu Lys Leu Ala Ala Arg Tyr Ile Asp
145                 150                 155                 160

Phe Leu Tyr Gln Val Leu Gln Ser Asp Glu Leu Asp Ser Lys Met Ala
                165                 170                 175

Ser Cys Ser Tyr Val Ala His Glu Arg Leu Ser Tyr Ala Phe Ser Val
            180                 185                 190

Trp Arg Met Glu Gly Ala Trp Ser Met Ser Ala Ser His
            195                 200                 205

<210> SEQ ID NO 16
<211> LENGTH: 618
<212> TYPE: DNA
<213> ORGANISM: Artificial sequence
<220> FEATURE:
<223> OTHER INFORMATION: Synthetic Twist nucleotide sequence

<400> SEQUENCE: 16
atgcaggacg tgtccagcag ccctgtgtct cctgccgacg acagcctgag caacagcgag      60
gaagaacccg acagacagca gcccgcctct ggcaagagag cgccagaaa gagaagaagc      120 tccagaagaa gcgctggcgg ctctgctgga cctggcggag ctacaggcgg aggaattgga    180
ggcggagatg agcctggctc tccagcccag ggcaagaggg caagaaatc tgctggcgga    240 ggcggcggag gaggagctgg aggcggagga ggaggcggcg gaggatcaag ttctggcgga    300
ggaagccctc agagctacga ggaactgcag acccagcgcg tgatggccaa cgtgcgcgag    360
agacagagaa cccagagcct gaacgaggcc ttcgccgccc tgagaaagat catccccacc    420
ctgcccagcg acaagctgag caagatccag accctgaagc tggccgccag atatatcgac    480
ttcctgtatc aagtgctgca gagcgacgag ctggacagca agatggccag ctgctcctac    540
gtggcccacg agagactgag ctacgccttc agcgtgtggc ggatggaagg cgcctggtct    600
atgagcgcca gccactga                                                   618

<210> SEQ ID NO 17
<211> LENGTH: 260
<212> TYPE: PRT
<213> ORGANISM: Artificial Sequence
<220> FEATURE:
<223> OTHER INFORMATION: Synthetic murine CD40L amino acid sequence

<400> SEQUENCE: 17

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
                20                  25                  30

Ile Thr Gln Met Ile Gly Ser Val Leu Phe Ala Val Tyr Leu His Arg
            35                  40                  45

Arg Leu Asp Lys Val Glu Glu Glu Val Asn Leu His Glu Asp Phe Val
50                  55                  60

Phe Ile Lys Lys Leu Lys Arg Cys Asn Lys Gly Glu Gly Ser Leu Ser

```
                65                  70                  75                  80
Leu Leu Asn Cys Glu Glu Met Arg Arg Gln Phe Glu Asp Leu Val Lys
                    85                  90                  95

Asp Ile Thr Leu Asn Lys Glu Glu Lys Lys Glu Asn Ser Phe Glu Met
                100                 105                 110

Gln Arg Gly Asp Glu Asp Pro Gln Ile Ala Ala His Val Val Ser Glu
                115                 120                 125

Ala Asn Ser Asn Ala Ala Ser Val Leu Gln Trp Ala Lys Lys Gly Tyr
            130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
                180                 185                 190

Trp Leu Lys Pro Ser Ser Gly Ser Glu Arg Ile Leu Leu Lys Ala Ala
            195                 200                 205

Asn Thr His Ser Ser Ser Gln Leu Cys Glu Gln Gln Ser Val His Leu
        210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 18
<211> LENGTH: 786
<212> TYPE: DNA
<213> ORGANISM: Artificial sequence
<220> FEATURE:
<223> OTHER INFORMATION: Synthetic murine CD40L nucleotide sequence

<400> SEQUENCE: 18
atgatcgaga catacagcca gcccagcccc agaagcgtgg ccacaggact gcctgccagc      60
atgaagatct ttatgtacct gctgaccgtg ttcctgatca cccagatgat cggcagcgtg     120
ctgttcgccg tgtacctgca cagacggctg acaaggtgg aagaggaagt gaacctgcac      180
gaggacttcg tgttcatcaa gaaactgaag cggtgcaaca agggcgaggg cagcctgagc     240
ctgctgaact gcgaggaaat gagaaggcag ttcgaggacc tcgtgaagga catcaccctg     300
aacaaagagg aaaagaaaga aaactccttc gagatgcaga ggggcgacga ggaccctcag     360
atcgctgctc acgtggtgtc cgaggccaac agcaacgccg cttctgtgct gcagtgggcc     420
aagaaaggct actacaccat gaagtccaac ctcgtgatgc tggaaaacgg caagcagctg     480
acagtgaagc gcgagggcct gtactatgtg tacacccaag tgacattctg cagcaacaga     540
gagcccagca gccagaggcc cttcatcgtg ggactgtggc tgaagcctag cagcggcagc     600
gagagaatcc tgctgaaggc cgccaacacc cacagcagct tcagctgtg cgagcagcag      660 agcgtgcacc tgggcggagt gttcgagctg caagctggcg cctccgtgtt cgtgaacgtg     720
acagaggcca gccaagtgat ccacagagtg ggcttcagca gctttggact gctgaaactg     780
taatga                                                                786
```

We claim:

1. A pharmaceutical composition comprising:
   (a) a recombinant modified vaccinia virus Ankara (MVA) comprising:
      (i) a first nucleic acid encoding a first heterologous tumor-associated antigen (TAA); and
      (ii) a second nucleic acid encoding CD40L; and
   (b) an antibody that comprises an Fc domain and is specific to an antigen expressed on the cell membrane of a tumor cell;
   wherein administration of (b) and intravenous administration of (a) to a cancer patient induces an enhanced Natural Killer (NK) cell response and an enhanced T cell response in comparison to an NK cell response and a T cell response of a cancer patient treated with an administration of (b) alone or a non-intravenous administration of (a) alone.

2. The pharmaceutical composition of claim 1, wherein said first nucleic acid encodes a tumor-associated antigen that is HER2.

3. The pharmaceutical composition of claim 2, wherein (b) comprises trastuzumab and the HER2 antigen comprises at least one mutation in the trastuzumab binding domain and selected from the group consisting of: E580, D582, P594, F595, K615, and Q624 corresponding to the amino acid sequence set forth in SEQ ID NO:13.

4. The pharmaceutical composition of claim 2, wherein (b) comprises pertuzumab and the HER2 antigen comprises at least one mutation in the pertuzumab binding domain and selected from the group consisting of: H267, Y274, F279, V308, S310, L317, H318, K333, and P337 corresponding to the amino acid sequence set forth in SEQ ID NO:13.

5. The pharmaceutical composition of claim 2, wherein the HER2 antigen comprises at least one mutation selected from the group consisting of:
   (a) a mutation that prevents extracellular dimerization of HER2 that is D277R or E280K;
   (b) a mutation that prevents tyrosine kinase activity of HER2 that is K753M; and
   (c) a mutation that interferes with phosphorylation of HER2 that is Y1023A or is the deletion of residues 1139-1248.

6. The pharmaceutical combination of claim 2, wherein said first nucleic acid encodes a HER2 antigen having the amino acid sequence set forth in SEQ ID NO:1 or SEQ ID NO: 13.

7. The pharmaceutical combination of claim 2, wherein said recombinant modified vaccinia virus Ankara (MVA) further comprises a third nucleic acid encoding a heterologous tumor-associated antigen (TAA) which is a Brachyury antigen.

8. The pharmaceutical combination of claim 7, wherein said Brachyury antigen comprises one or more mutations to the nuclear localization signal (NLS) domain or in which the NLS domain is deleted.

9. The pharmaceutical combination of claim 7, wherein said Brachyury antigen has an amino acid sequence that comprises the sequence set forth in SEQ ID NO:3.

* * * * *